(12) United States Patent
Lub et al.

(10) Patent No.: US 9,463,256 B2
(45) Date of Patent: Oct. 11, 2016

(54) PRETARGETING KIT, METHOD AND AGENTS USED THEREIN

(75) Inventors: Johan Lub, Valkenswaard (NL); Wolter Ten Hoeve, Assen (NL); Raffaella Rossin, Eindhoven (NL); Sandra Martina Van Den Bosch, Weert (NL); Marc Stefan Robillard, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 13/877,725

(22) PCT Filed: Oct. 11, 2011

(86) PCT No.: PCT/IB2011/054481
§ 371 (c)(1),
(2), (4) Date: Apr. 4, 2013

(87) PCT Pub. No.: WO2012/049624
PCT Pub. Date: Apr. 19, 2012

(65) Prior Publication Data
US 2013/0189184 A1    Jul. 25, 2013

(30) Foreign Application Priority Data
Oct. 14, 2010  (EP) .................... 10187619

(51) Int. Cl.
| | | |
|---|---|---|
| *A61K 51/04* | (2006.01) | |
| *A61K 51/10* | (2006.01) | |
| *A61K 47/48* | (2006.01) | |
| *A61K 49/16* | (2006.01) | |
| *B82Y 5/00* | (2011.01) | |

(52) U.S. Cl.
CPC ....... *A61K 51/1093* (2013.01); *A61K 47/4813* (2013.01); *A61K 47/48215* (2013.01); *A61K 47/48723* (2013.01); *A61K 49/16* (2013.01); *A61K 51/0495* (2013.01); *A61K 51/10* (2013.01); *B82Y 5/00* (2013.01)

(58) Field of Classification Search
CPC ........................... A61K 49/00; A61K 51/00
USPC ............ 424/1.11, 1.49, 1.53, 1.65, 1.69, 9.1
See application file for complete search history.

(56) References Cited

FOREIGN PATENT DOCUMENTS

| WO | WO2007039858 | * | 4/2007 |
|---|---|---|---|
| WO | 2010051530 | A2 | 5/2010 |
| WO | 2010119389 | A2 | 10/2010 |

OTHER PUBLICATIONS

Devaraj et al. Tetrazine-based cycloadditions: application to pretargeted live cell imaging. 2008 Bioconjug. Chem. 19: 2297-2299.*
Sauer et al. 1,2,4,5-tetrazine: synthesis and reactivity in [4+2] cycloadditions. 1998 Eur. J. Org. Chem. 12: 2885-2896.*
Melissa L. Blackman et al. Tetrazine Ligation: Fast Bioconjugation Based on Inverse-Electron-Demand Diels-Alder Reactivity, J. Am. Chem. Soc. 130, 13518-13519, 2008.*
Goldenberg, D.M. et al. "Antibody Pretargeting Advances Cancer Radioimmunodetection and Radioimmunotherapy", J Clin Oncol 2006, 24(5), 823-834.
Boerman, O.C. et al., "Pretargeted Radioimmunotherapy of Cancer: Progress Step by Step", J Nucl Med 2003, 44, 400-411.
Goldenberg, D.M. et al., "Radioimmunotherapy: is Avidin-Biotin Pretargeting Teh Preferred Choice Among Pretargeting Methods?" Eur J Nucl Med Mol Imaging 2003, 30, 777.
Rossin, R. et al., "In vivo Chemistry for Pretargeted Tumor Imaging in Live Mice", Angew Chem Int Ed 2010, 49, 3375-3378.
Blackman, M.L. et al, "ORGN 646", J Am Chem Soc 2008, 130, 13518.
Devaraj, N.K. et al. "Bioorthogonal Turn on Probes for Imaging Small Molecules Inside Living Cells", Angew Chem Int Ed 2010, 49, 2869.
Devaraj, N.K. et al., "Fast and Sensitive Pretargeted Labeling of Cancer Cells Through a Tetrazine/Trans-Cyclooctene Cycloaddtion", Angew Chem Int Ed 2009, 48, 7013.
Thalhammer, F. et al. "RKAKTIVISXX XIHFACHXB OFVKHXKTCIOEB UHD CTCZ.ISCHXB DIXVOPHILX BSI DXBS8-A1VDKB-HKAKXI0HXH HZC XOTKR8XH XLK-KXBOHXHBXDABF", Tetrahedron Lett 1990, 31, 6851.
Leong, M.K. et al. "Structure and Conformations of Cyclopentene, Cycloheptene and Trans Cyclooctene" J Mol Str 1998, 445, 149.
King, M.D. et al. "Frontier Molecular Orbital Correlations for Predicting Rate Constants Between Alkenes and the Tropospheric Oxidants NO 3, OH and O)3", Phys Chem Chem Phys 1999, 1, 2231.
Boger, D.L., "Diels-Alder Reactions of Heterocyclic Aza Dienes, Scope and applications"., Chem Rev 1986, 86, 781.
Royzen, M. et al., "A Photochemical Synthesis of Functionalized Trans-Cyclooctenes Driven by Metal Comlexation", J Am Chem Soc 2008, 130, 3760-3761.
Li, Zibo et al. "Tetrazine-Trans-Cyclooctene Litigation for Rapid Construction of F Labeled Probes" , The Royal Society of Chemistry 2010, Chem. Comm., 46, 8043-8045.
Blackman, M.L. et al. "Tetrazine Litigation: Fast Bioconjugation Based on Inverse Electron Demand Diels Alder Reactivity", JACS Communications, 2009, 130, 13518-13519.
Brecht, R. et al., "Positional and Facial Selectivity in Diels-Alder Reactions of (-)-(aS,7S)-Colchicine: Synthesis of Novel Analogues of the Alkaloid", Liebigs Ann IRecueil 1997, 851-857.
Garcia, J.G. et al. "Reverse Electron Demand Diels Alder Dienophile Tt-FACE Selectivity via Conformation Dependent Transmission of n-o-ir Electronic Interactions", Tetrahedron Letters, vol. 32, No. 28, pp. 3293-3296, 1991, Great Britain.
Braun, K. et al. "Treatment of Glioblastoma Multiforme Cells with Temozolomide-Bioshuttle Ligated by the Inverse Diels-Alder Ligation Chemistry", Drug Design, Development and Therapy 2008 2 289-301.

* cited by examiner

*Primary Examiner* — Michael G Hartley
*Assistant Examiner* — Jagadishwar Samala

(57) ABSTRACT

Described is a pretargeting method, and related kits, for targeted medical imaging and/or therapeutics, wherein use is made of abiotic reactive chemical groups that exhibit bioorthogonal reactivity towards each other. The invention involves the use of [4+2] inverse electron demand (retro) Diels-Alder chemistry in providing the coupling between a Pre-targeting Probe and an Effector Probe. To this end one of these probes comprises an electron-deficient tetrazine or other suitable diene, and the other an E-cyclooctene which has one or more axial substituents.

11 Claims, 16 Drawing Sheets

PRETARGETING KIT, METHOD AND AGENTS USED THEREIN

FIELD OF THE INVENTION

The invention relates to a pretargeting method, for targeted medical imaging and/or therapeutics, wherein use is made of abiotic reactive chemical groups that exhibit bio-orthogonal reactivity towards each other. The invention also relates to a pretargeting kit comprising at least one Pre-targeting Probe and at least one Effector Probe, wherein the Pre-targeting Probe comprises a primary targeting moiety and a first Bio-orthogonal Reactive Group, and wherein the Effector Probe comprises an Effector Moiety, such as a label or a pharmaceutically active compound, and a second Bio-orthogonal Reactive Group. The invention also relates to pre-targeting agents used in the above-mentioned method and kit. The invention particularly pertains to nuclear imaging and radiotherapy.

BACKGROUND OF THE INVENTION

In many areas of medical diagnosis and therapy, it is desired to selectively deliver an agent, such as a therapeutic agent (a drug) or a diagnostic (e.g. imaging) agent, to a specific site, or a confined region, in the body of a subject such as a patient.

Active targeting of an organ or a tissue is achieved by the direct or indirect conjugation of the desired active moieties (e.g. a contrast enhancing agent or a cytotoxic compound) to a targeting construct, which binds to cell surfaces or promotes cellular uptake at or near the target site of interest. The targeting moieties used to target such agents are typically constructs that have affinity for cell surface targets (e.g., membrane receptors), structural proteins (e.g., amyloid plaques), or intracellular targets (e.g., RNA, DNA, enzymes, cell signaling pathways). These moieties can be antibodies (fragments), proteins, aptamers, oligopeptides, oligonucleotides, oligosaccharides, as well as peptides, peptoids and organic drug compounds known to accumulate at a particular disease or malfunction. Alternatively, a contrast/therapeutic agent may target a metabolic pathway, which is upregulated during a disease (like infection or cancer) such as DNA, protein, and membrane synthesis and carbohydrate uptake. In diseased tissues, abovementioned markers can discriminate diseased cells from healthy tissue and offer unique possibilities for early detection, specific diagnosis and (targeted) therapy.

An important criterion for successful molecular imaging/therapy agents in general and nuclear imaging/therapy agents in particular is that they exhibit a high target uptake while showing a rapid clearance (through renal and/or hepatobiliary systems) from non-target tissue and from the blood. However, this is often problematic: for example, imaging studies in humans have shown that the maximum concentration of a radio labeled antibody at the tumor site is attainable within 24 h but several more days are required before the concentration of the labeled antibody in circulation decreases to levels low enough for successful imaging to take place.

These problems (especially for nuclear imaging and therapy) with slow or insufficient accumulation in target tissue and slow clearance from non-target areas have lead to the application of pre-targeting approaches.

Pretargeting refers to a step in a targeting method, wherein a primary target (e.g. a cell surface) is provided with a Pre-targeting Probe. The latter comprises a secondary target, which will eventually be targeted by a further probe (the Effector Probe) equipped with a secondary targeting moiety.

Thus, in pre-targeting, a Pre-targeting Probe is bound to a primary target. The Pre-targeting Probe also carries secondary targets, which facilitate specific conjugation to a diagnostic (imaging) and/or therapeutic agent, the Effector Probe. After the construct forming the Pre-targeting Probe has localized at the target site (taking time, e.g. 24 h), a clearing agent can be used to remove excess from the blood, if natural clearance is not sufficient. In a second incubation step (preferably taking a shorter time, e.g., 1-6 hours), the Effector Probe binds to the (pre)bound Pre-targeting Probe via its secondary targeting moiety. The secondary target (present on the Pre-targeting Probe) and the secondary targeting moiety (present on the Effector Probe) should bind rapidly, with high specificity and high affinity and should be stable within the body.

The general concept of pre-targeting is outlined for imaging in FIG. 1. Herein the Effector Probe is an imaging probe comprising a detectable label for an imaging modality. The Effector Probe binds to the (pre)-bound Pre-targeting Probe via its secondary targeting groups.

Common examples for secondary target/secondary targeting moiety pairs are biotin/streptavidin or antibody/antigen systems. To be effective, the Effector Probe must be rapidly excreted from the body (e.g., through the kidneys) to provide the desired high tumor accumulation with relatively low non-target accumulation. Therefore, these probes are usually small.

In nuclear imaging and radiotherapy the concept of pre-targeting is of further advantage, as the time consuming pre-targeting step can be carried out without using radionuclides, while the secondary targeting step using a radionuclide can be carried out faster. The latter allows the use of shorter lived radionuclides with the advantage of minimizing the radiation dose to the patient and, for instance, the usage of PET agents instead of SPECT agents. Using a pre-targeting approach in MRI in combination with multidentate ligand systems (streptavidin, dendrimers) can afford signal amplification at target sites. Furthermore, in general, this approach facilitates the usage of a universal contrast agent.

The entities that carry out highly selective interactions in biology in general (like antibody-antigen), and in pre-targeting in particular (biotin-streptavidin, antibody/haptens, antisense oligonucleotides), are very large. As a result, pre-targeting with peptides and small organic moieties as primary targeting groups, as well as metabolic imaging and intracellular target imaging, have remained out of reach as the size of the secondary targets makes the use of small primary groups pointless.

Moreover, the current pretargeting systems are hampered by factors associated with their biological nature. Biotin is an endogenous molecule and its conjugates can be cleaved by the serum enzyme biotinidase. When antisense pre-targeting is used, the oligonucleotides can be subject to attack by RNAse and DNAse. Proteins and peptides are also subject to natural decomposition pathways. These interactions can be further impaired by their non-covalent and dynamic nature and limited on-target residence time. Also, endogenous biotin competes with biotin conjugates for streptavidin binding. Finally, streptavidin is highly immunogenic.

A recent development is to avoid the drawbacks associated with pretargeting solely on the basis of natural/biological targeting constructs (i.e., biotin/streptavidin, antibody/hapten, antisense oligonucleotides).

A reference in this respect is WO 2010/051530, wherein pretargeting is discussed on the basis of the reactivity between certain dienes, such as tetrazines and dienophiles such as a trans-cyclooctenol (TCO).

A further reference in this respect is Li et al., Chemical Communications, 2010, 46(42), p. 8043-8045, which describes a radiolabeling method for bioconjugation based on the Diels-Alder reaction between 3,-diaryl-s-tetrazines and an $^{18}$F-labeled trans-cyclooctene.

Rossin et al., Angew. Chem. Int., Ed 2010, 49, p. 3375-3378 relates to tumor pretargeting by using the inverse-electron-demand Diels-Alder reaction.

Blackman et al., J. Am. Chem. Soc., 2008, 130, p. 13518-13519 describe fast bioconjugation based on inverse-electron-demand Diels-Alder reactivity.

Royzen et al., J. Am. Chem. Soc., 2008, 130, p. 3760-3761 refers to photochemical synthesis of functionalized trans-cyclooctenes driven by metal complexation.

Although on the basis of such systems a relatively fast reaction can be obtained, this does not come near the reactivity of the above-mentioned biotin-streptavidin system. Hence, avoiding the drawbacks of the latter, goes at cost of the primary requirement of the reaction, viz. speed. It is thus desired to provide a system that is not based on biomolecules as discussed above, and yet has a desirably fast reaction rate.

SUMMARY OF THE INVENTION

In order to better address the foregoing desires, the invention, in one aspect, provides a kit for targeted medical imaging and/or therapeutics, comprising at least one Pre-targeting Probe and at least one Effector Probe, wherein the Pre-targeting Probe comprises a Primary Targeting Moiety and a first Bio-orthogonal Reactive Group, and wherein the Effector Probe comprises an Effector Moiety, such as a label or a pharmaceutically active compound, and a second Bio-orthogonal Reactive Group, wherein either of the first and second Bio-orthogonal Reactive Groups is a dienophile and the other of the first and second Bio-orthogonal Reactive Groups is a diene, wherein the dienophile is an 8-member ring dienophile satisfying formula (1):

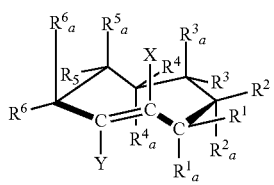

(1)

wherein the position of R is equatorial and the position of $R_a$ is axial, wherein each of X, Y, R, and $R_a$ independently denotes H, or, in at most six instances, a substituent selected from the group consisting of alkyl, aryl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, N$_3$, SO$_2$H, SO$_3$H, SO$_4$H, PO$_4$H, OH, SH, NO$_2$, NO, CN, OCN, SCN, NCO, NCS, CF$_3$, NR'R'' with R' and R'' each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R'' with R' and R'' each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR''-alkyl with R' and R'' each independently being H, alkyl or aryl, NR'CONR''-aryl with R' and R'' each independently being H, alkyl or aryl, NR'CSNR''-alkyl with R' and R'' each independently being H, alkyl or aryl, and NR'CSNR''-aryl with R' and R'' each independently being H, alkyl or aryl, CR'NR'' with R' and R'' each independently being H, alkyl or aryl; with one of R or $R_a$ comprised in a Linker Moiety, optionally via a spacer, to the Pre-targeting Probe or the Effector Probe; wherein two R or $R_a$ moieties together may form a ring; and wherein at least one and maximally four of $R_a$ is not hydrogen.

In another aspect, the invention provides a pre-targeting method, as well as pre-targeting agents used therein, and targeted medical imaging or therapy wherein this kit is used.

In a still further aspect, the invention is a compound satisfying the above formula (1), for use in a pre-targeting method in an animal or a human being.

In yet another aspect, the invention resides in the use of a trans cyclooctene having one or more axial substituents as a dienophile reactant in a pre-targeting method based on the retro Diels-Alder reaction.

DETAILED DESCRIPTION OF THE INVENTION

Figure 1:
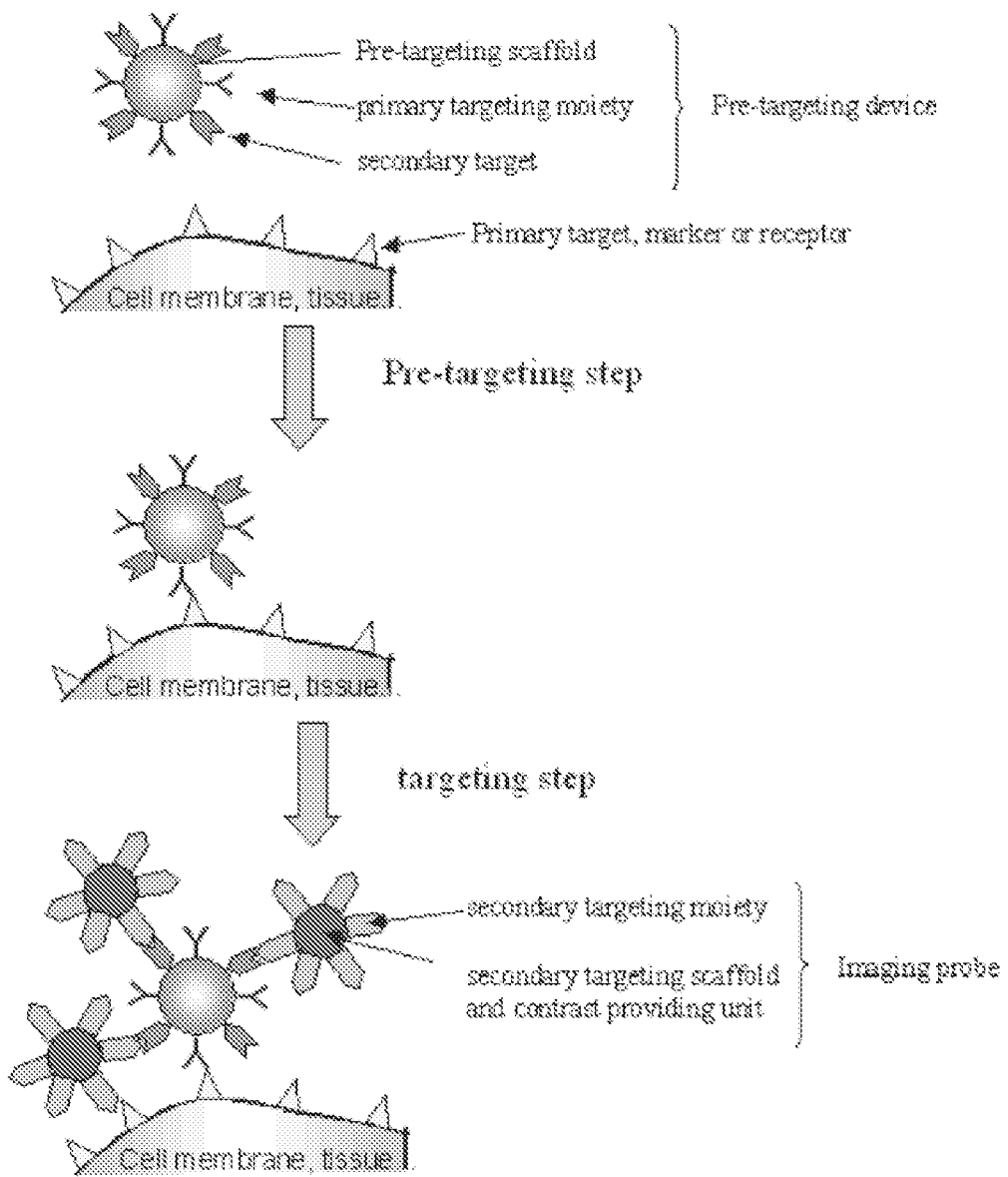
FIG. 1 depicts a general scheme of a pretargeting concept, as discussed above.

The strained cyclooctene dienophile used in the present invention is hereinafter denoted E-cyclooctene. With reference to the conventional nomenclature, it will be understood that, as a result of substitution X or Y, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dienophiles according to the present invention, also in the event that substituents would formally require the opposite nomenclature. I.e., the invention relates to cyclooctene in which carbon atoms 1 and 6 as numbered below are in the E (entgegen) or trans position.

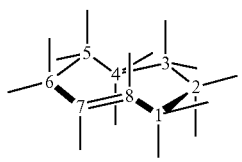

In a general sense, the invention is based on the recognition that in the system using derivatized trans-cyclooctene, e.g. in the form of trans-cyclooctenol, as a dienophile, the isomer is selected in which the hydroxyl group used for derivatization into a linker structure, is in the axial position. E-cyclooctenol, which is in a so-called crown conformation, has two isomers, the one having OH in the equatorial position being the major isomer and the one having OH in the axial position being the minor isomer. The latter isomer is selected according to the invention, and is hereinafter denoted "E-minor."

Without wishing to be bound by theory, the present inventors believe, based on this finding, that the presence of one or more axial substituents on TCO provides a key to addressing the need for higher reactivities in pre-targeting on the basis of the retro-Diels-Alder reaction.

In a broad sense, the invention therefore extends beyond the definition of substituents given with reference to formula (1) as given above. The fact that one or more axial substituents are present is believed to result in a higher HOMO energy. HOMO, as known to the skilled person, stands for the highest occupied molecular orbital. According to the invention, MOPAC simulations are used to determine the HOMO energy of the TCO. MOPAC (Molecular Orbital Package) is well-known software in the field of computational chemistry. The MOPAC software package incorporates several well-known semi-empirical molecular orbital methods, including AM1 and PM3. The terms AM1 and PM3 refer to different Hamiltonians, namely the Austin Model 1 and the parameterized model 3 Hamiltonian (for AM1 see also M. J. S. Dewar, et al., J. Am. Chem. Soc., 107, 3902 (1985); for PM3 see also J. J. P. Stewart, J. Comput. Chem., 10, 209 (1989) and J. Comput. Chem., 10, 221 (1989)).

In the invention, a method is used comprising, in a computer environment, providing a molecular structure of derivatives of cyclooctene, optimizing each molecular structure by determining the lowest energy of formation, determining the AM1 and PM3 Hamiltonians and so determining the highest occupied molecular orbital (HOMO).

The MOPAC data in Table 6 show that the presence of axial substituents serves the purpose of providing an increased HOMO energy in the trans-cyclooctene ring.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

It is furthermore to be noticed that the term "comprising", used in the description and in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In several chemical formulae reference is made to "alkyl" and "aryl." In this respect "alkyl", each independently, indicates an aliphatic, straight, branched or cyclic alkyl group of up to ten carbon atoms, possibly including 1-3 heteroatoms such as O, N, or S, preferably of 1-6 carbon atoms and "aryl," each independently, indicates an aromatic or heteroaromatic group of up to ten carbon atoms, possibly including 1-3 heteroatoms such as N or S. In several formulae, groups or substituents are indicated with reference to letters such as "A", "B", "X", "Y", and various numbered "R" groups. The definitions of these letters are to be read with reference to each formula, i.e. in different formulae, these letters, each independently, can have different meanings unless indicated otherwise.

In further preferred embodiments of the present invention, in several chemical formulae below reference is made to "alkyl" and "aryl." In this respect "alkyl", each independently, indicates an aliphatic, straight, branched, saturated, unsaturated and/or or cyclic hydrocarbyl group of up to ten carbon atoms, possibly including 1-10 heteroatoms such as O, N, or S, and "aryl", each independently, indicates an aromatic or heteroaromatic group of up to twenty carbon atoms, that possibly is substituted, and that possibly includes 1-10 heteroatoms such as O, N, P or S. "Aryl" groups also include "alkylaryl" or "arylalkyl" groups (simple example: benzyl groups). The number of carbon atoms that an "alkyl", "aryl", "alkylaryl" and "arylalkyl" contains can be indicated by a designation preceding such terms (i.e. $C_{1-10}$ alkyl means that said alkyl may contain from 1 to 10 carbon atoms). Certain compounds of the invention possess chiral centers and/or tautomers, and all enantiomers, diasteriomers and tautomers, as well as mixtures thereof are within the scope of the invention.

Retro Diels-Alder Reaction

The Retro Diels-Alder coupling chemistry generally involves a pair of reactants that couple to form an unstable intermediate, which intermediate eliminates a small molecule (depending on the starting compounds this may be e.g. $N_2$, $CO_2$, RCN, as the sole by-product through a retro Diels-Alder reaction to form a stable product. The paired reactants comprise, as one reactant (i.e. one Bio-orthogonal Reactive Group), a suitable diene, such as a derivative of tetrazine, e.g. an electron-deficient tetrazine and, as the other reactant (i.e. the other Bio-orthogonal Reactive Group), a strained cyclooctene according to formula (1).

Figure 2:
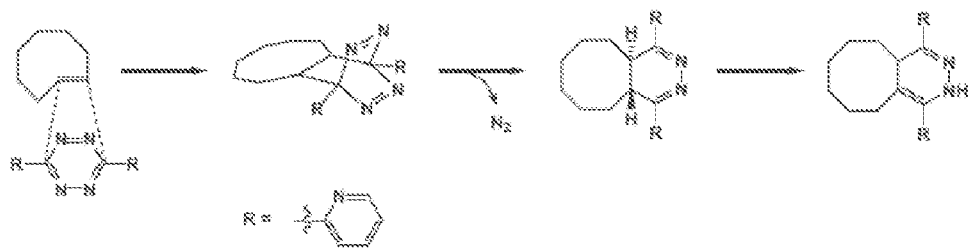
FIG. 2. provides the reaction scheme for a [4+2] Diels-Alder reaction; between (3,6)-di-(2-pyridyl)-s-tetrazine and E-cyclooctene followed by a retro Diels Alder reaction in which the product and dinitrogen is formed. Because the trans cyclooctene derivative does not contain electron withdrawing groups as in the classical Diels Alder reaction, this type of Diels Alder reaction is distinguished from the classical one, and frequently referred to as an "inverse electron demand Diels Alder reaction". In the following text the sequence of both reaction steps, i.e. the initial Diels-Alder cyclo-addition (typically an inverse electron demand Diels Alder cyclo-addition) and the subsequent retro Diels Alder reaction will be referred to in shorthand as "retro Diels Alder reaction" or "retro-DA".

The exceptionally fast reaction of, e.g., electron-deficient (substituted) tetrazines with the strained E-cyclooctene of the invention results in a ligation intermediate that rearranges to a stable dihydropyridazine by eliminating $N_2$ as the sole by-product in a [4+2] Retro Diels-Alder cycloaddition. This is shown in FIG. 2.

The two reactive species are abiotic and thus do not undergo a fast metabolism in vivo. They are bio-orthogonal, e.g. they selectively react with each other in physiologic media. An advantage hereof is that both the diene and the cyclooctene are essentially unreactive toward biomolecules inside or on the surfaces of cells and all other regions like serum etc. Thus, the compounds and the method of the invention can be used in a living cell, tissue or organism. Moreover, the reactive groups are relatively small and can be introduced in biological samples or living organisms without altering the biological size significantly. Using the [4+2] retro Diels-Alder reaction it is possible to bind primary targeting moieties which are large in size, e.g. antibodies, with labels or other molecules using small reaction partners, e.g. tetrazine or cyclooctene. Even more advantageously, primary targeting moieties can be bound which are relatively small, e.g. peptides, with labels or other molecules using (matched) relatively small reaction partners, e.g. tetrazine and cyclooctene. The size and properties of the Pre-targeting Probe and Effector Probe are not greatly affected by the secondary target and secondary targeting moiety, allowing (pre)targeting schemes to be used for small targeting moieties. Because of this, other tissues can be targeted, i.e. the destination of the probes is not limited to the vascular system and interstitial space, as is the case for current pretargeting with antibody-streptavidin.

References on the Inverse electron demand Diels Alder reaction, and the behavior of the pair of reactive species include: Thalhammer, F; Wallfahrer, U; Sauer, J, Tetrahedron Letters, 1990, 31 (47), 6851-6854; Wijnen, J W; Zavarise, S; Engberts, J B F N, Journal Of Organic Chemistry, 1996, 61, 2001-2005; Blackman, M L; Royzen, M; Fox, J M, Journal Of The American Chemical Society, 2008, 130 (41), 13518-19), R. Rossin, P. Renart Verkerk, Sandra M. van den Bosch, R. C. M. Vulders, 1. Verel, J. Lub, M. S. Robillard, Angew Chem Int Ed 2010, 49, 3375, N. K. Devaraj, R. Upadhyay, J. B. Haun, S. A. Hilderbrand, R. Weissleder, Angew Chem Int Ed 2009, 48, 7013, and Devaraj et al., Angew. Chem. Int. Ed., 2009, 48, 1-5.

It will be understood that, in a broad sense, according to the invention the aforementioned coupling chemistry can be applied to basically any pair of molecules, groups, or moieties that are capable of being used in pretargeting. I.e. one of such a pair will comprise a primary targeting moiety, that is capable of binding to a primary target, and further comprises at least one secondary target. The other one will be a secondary targeting moiety suitable for use in binding to said secondary target, and further comprises a moiety suitable for exerting therapeutic action (typically a pharmaceutically active compound), or for being addressed by an imaging technique (i.e. a label), or both.

Figure 3A:
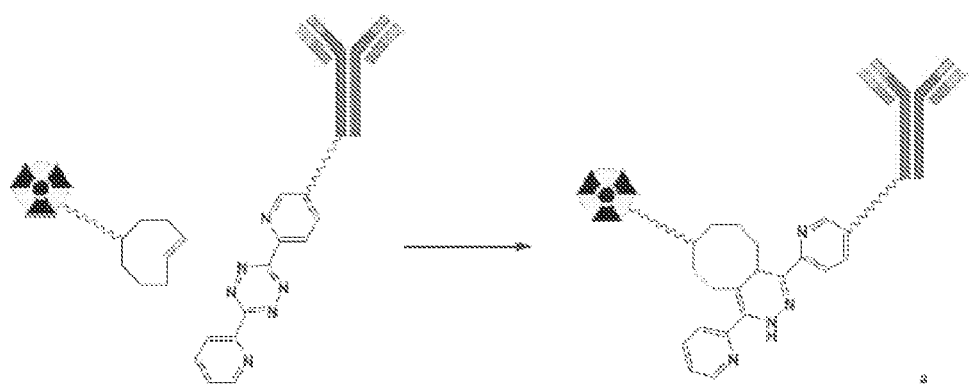
FIGS. 3 (a and b) depicts general schemes for pre-targeting using retro Diels-Alder chemistry.
Figure 3B:
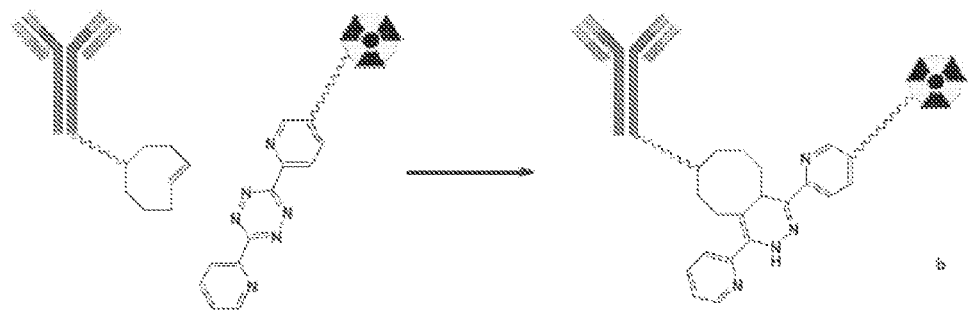
Figure 4:
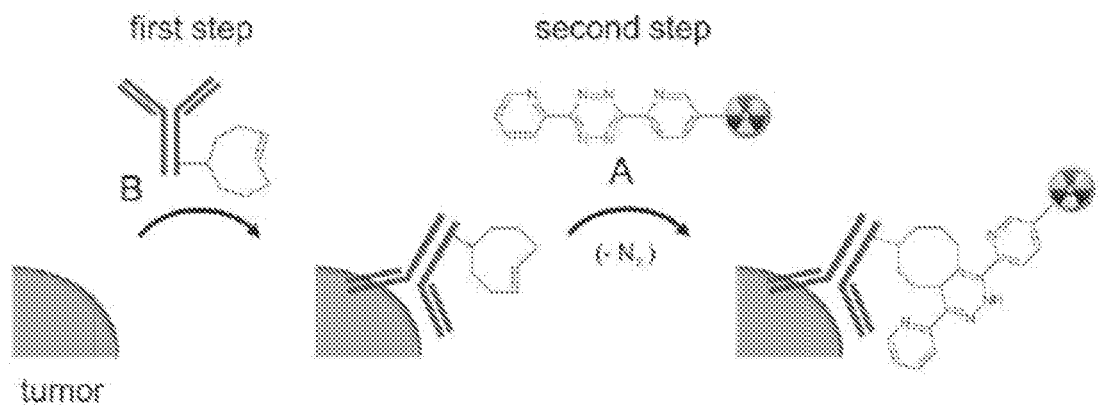
FIG. 4 presents a scheme of tumor pretargeting with retro-DA involving a TCO-modified mAb (B) and a radio labeled tetrazine (A)

Thus, according to the invention, either of the Pre-targeting Probe and the Effector Probe is functionalized with an axially substituted cyclooctene as defined above, and the other is functionalized with a tetrazine, or other suitable diene. This is illustrated in FIG. 3. The scheme on top (FIG. 3a) indicates a Pre-targeting Probe comprising di-pyridyl tetrazine linked, via a linker moiety (optionally comprising a flexible spacer) to an antibody as the primary targeting moiety, and an Effector Probe comprising cyclooctene (as the secondary targeting moiety) attached, via a linker (a flexible spacer), to a detectable label. The scheme below (FIG. 3b) shows exactly the opposite, viz. a Pre-targeting Probe comprising the cyclooctene and an Effector Probe comprising the tetrazine.

Although the stereochemistry is not expressly shown in the figures, it will be understood that in the present invention the cyclooctene is an Axially substituted cyclooctene in accordance with formula (1) as defined above.

Dienophiles

A fundamental achievement of the present invention, is that a dienophile is selected, viz. Axially substituted TCO according to formula (1) as defined above, that allows achieving increased reaction rates for the bio-orthogonal coupling reaction up to ten times or more. Or, put otherwise, a reaction time that is only 10% of the time originally required. Or, put still otherwise, the concentration of one reactant can be 10 times lower.

The dienophile, in a broad sense, is a trans-cyclooctene having at least one axial substituent, i.e. wherein at least one axial position of at least one saturated carbon atom is not hydrogen.

As explained above, at least one and maximally four of $R_a$ is not hydrogen, meaning that such $R_a$ is a substituent or is part of a linker structure. Preferably, the number of non-hydrogen $R_a$ is one or two.

More preferably. the at least one, and maximally four of the non-hydrogen $R_a$ are in the position selected from the group consisting of $R^2_a$, $R^3_a$, $R^4_a$, and $R^5_a$. Still more preferably, one or two of $R^2_a$, $R^3_a$, $R^4_a$, and $R^5_a$ are non-hydrogen. Most preferably, a substituent or linker structure is present as one or both of $R^3_a$ and $R^4_a$.

Preferably the substituent is selected from the group defined above with reference to formula (1) as defined above. More preferably, the aforementioned $R_a$ is alkyl or O-alkyl, more preferably methyl or O-t-butyl.

It should be noted that the options and preferences for $R_a$ are irrespective of whether or not any substituents are present in the equatorial position (i.e. the R groups in formula (1) as defined above), on another carbon atom or on the same carbon atom. Preferably, in addition to one or two axial substituents, also one or two equatorial substituents are present, said substituents preferably including the R or $R_a$ that is part of a linker structure. However, in another preference, with a view to striking a balance between synthesis efforts and reactivity, it is preferred that one or two $R_a$ are not hydrogen, and all other R and $R_a$ are hydrogen.

In a further preference, X and/or Y are O-alkyl or alkyl, more preferably methyl.

Dienes

The person skilled in the art is aware of the wealth of dienes that are reactive in the Retro Diels-Alder reaction. Preferred dienes are given below, with reference to formulae (2)-(5).

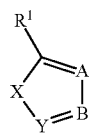

(2)

wherein $R^1$ is selected from the group consisting of H, alkyl, aryl, CF$_3$, CF$_2$—R', OR', SR', C(=O)R', C(=S)R', C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", NR'C(=O)NR'"R"', NR'C(=S)N'R'R"' with R', R", and R"' each independently being H, aryl or alkyl; A and B each independently are selected from the group consisting of alkyl-substituted carbon, aryl substituted carbon, nitrogen, N$^+$O$^-$, N$^+$R with R being alkyl, with the proviso that A and B are not both carbon; X is selected from the group consisting of O, N-alkyl, and C=O, and Y is CR with R being selected from the group consisting of H, alkyl, aryl, C(=O)OR', C(=O)SR', C(=S)OR', C(=S)SR', C(=O)NR'R" with R' and R" each independently being H, aryl or alkyl;

A diene particularly suitable as a reaction partner for cyclooctene is:

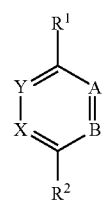

(3)

wherein $R^1$ and $R^2$ each independently are selected from the group consisting of H, alkyl, aryl, CF$_3$, CF$_2$—R', NO$_2$, OR', SR', C(=O)R', C(=S)R', OC(=O)R"', SC(=O)R"', OC(=S)R"', SC(=S)R"', S(=O)R', S(=O)$_2$R"', S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R'R" with R' and R" each independently being H, aryl or alkyl, and R"' independently being aryl or alkyl; A is selected from the group consisting of N-alkyl, N-aryl, C=O, and CN-alkyl; B is O or S; X is selected from the group consisting of N, CH, C-alkyl, C-aryl, CC(=O)R', CC(=S)R', CS(=O)R', CS(=O)$_2$R"', CC(=O)O—R', CC(=O)S—R', CC(=S)O—R', CC(=S)S—R', CC(=O)NR'R", CC(=S)NR'R", R' and R" each independently being H, aryl or alkyl and R"' independently being aryl or alkyl; Y is selected from the group consisting of CH, C-alkyl, C-aryl, N, and N$^+$O$^-$;

Another diene particularly suitable as a reaction partner for cyclooctene is:

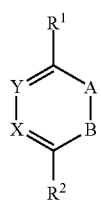

(4)

wherein $R^1$ and $R^2$ each independently are selected from the group consisting of H, alkyl, aryl, CF$_3$, CF$_2$—R', NO$_2$, OR', SR', C(=O)R', C(=S)R', OC(=O)R"', SC(=O)R"', OC(=S)R"', SC(=S)R"', S(=O)R', S(=O)$_2$R"', S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R'R" with R' and R" each independently being H, aryl or alkyl, and R"' independently being aryl or alkyl; A is selected from the group consisting of N, C-alkyl, C-aryl, and N$^+$O$^-$; B is N; X is selected from the group consisting of N, CH, C-alkyl, C-aryl, CC(=O)R', CC(=S)R', CS(=O)R', CS(=O)$_2$R"', CC(=O)O—R', CC(=O)S—R', CC(=S)O—R', CC(=S)S—R', CC(=O)NR'R", CC(=S)NR'R", R' and R" each independently being H, aryl or alkyl and R"' independently being aryl or alkyl; Y is selected from the group consisting of CH, C-alkyl, C-aryl, N, and N$^+$O$^-$;

Particularly useful tetrazine derivatives are electron-deficient tetrazines, i.e. tetrazines substituted with groups or moieties that do not generally hold as electron-donating, and preferably carrying electron-withdrawing substituents.

These electron-deficient tetrazines generally satisfy the following structural formula:

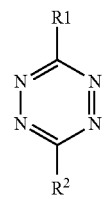

(5)

Herein $R^1$ and $R^2$ each independently denote a substituent selected from the group consisting of H, 2-pyridyl, 3, pyridyl, 4-pyridyl, 2,6-pyrimidyl, 2,5-pyrimidyl, 3,5-pyrimidyl, 2,4-pyrimidyl, or phenyl, optionally substituted with one or more electron-withdrawing groups such as NO$_2$, F, Cl, CF3, CN, COOH, COOR, CONH$_2$, CONHR, CONR$_2$, CHO, COR, SO$_2$R, SO$_2$OR, NO, Ar, wherein R is C$_1$-C$_6$ alkyl and Ar stands for an aromatic group, particularly phenyl, pyridyl, or naphthyl.

In the compounds according to each of the formulae (2)-(5), the R$^1$ and R$^2$ groups (including those on X or Y), can further be provided with suitable linker or spacer moieties as discussed below. Analogously, and independently thereof, also the dienophile of formula (1) as defined above can further be provided with suitable linker or spacer moieties as discussed below.

According to one embodiment, the invention is used for targeted imaging.

According to this embodiment, imaging of a specific primary target is achieved by specific binding of the primary targeting moiety of the Pre-targeting Probe and detection of this binding using detectable labels comprised in the Effector Probe.

Primary Target

A "primary target" as used in the present invention relates to a target to be detected in a diagnostic and/or imaging method, and/or to be modulated, bound, or otherwise addressed by a pharmaceutically active compound, or other therapeutic modality.

The primary target can be selected from any suitable targets within the human or animal body or on a pathogen or parasite, e.g. a group comprising cells such as cell membranes and cell walls, receptors such as cell membrane receptors, intracellular structures such as Golgi bodies or mitochondria, enzymes, receptors, DNA, RNA, viruses or viral particles, antibodies, proteins, carbohydrates, monosaccharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-) angiogenesis marker, gastrin receptor, dopaminergic system, serotonergic system, GABAergic system, adrenergic system, cholinergic system, opoid receptors, GPIIb/IIIa receptor and other thrombus related receptors, fibrin, calcitonin receptor, tuftsin receptor, integrin receptor, VEGF/EGF receptors, EGF, matrix metalloproteinase (MMP), P/E/L-selectin receptor, LDL receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase.

According to a particular embodiment of the present invention, the primary target is a protein such as a receptor. Alternatively, the primary target may be a metabolic pathway, which is upregulated during a disease, e.g. infection or cancer, such as DNA synthesis, protein synthesis, membrane synthesis and carbohydrate uptake. In diseased tissues, above-mentioned markers can differ from healthy tissue and offer unique possibilities for early detection, specific diagnosis and therapy, especially targeted therapy.

Pre-Targeting Probe

A Pre-targeting Probe comprises a moiety that is capable of binding to the primary target of interest.

Targeting moieties are typically constructs that have affinity for cell surface targets (e.g., membrane receptors), structural proteins (e.g., amyloid plaques), or intracellular targets (e.g., RNA, DNA, enzymes, cell signaling pathways). These moieties can be antibodies (fragments), proteins, aptamers, oligopeptides, oligonucleotides, oligosaccharides, as well as peptides, peptoids and organic drug compounds known to accumulate at a particular disease or malfunction.

Particular embodiments of suitable primary targeting moieties for use in the kits of the present invention are described herein and include receptor binding peptides and antibodies. A particular embodiment of the present invention relates to the use of small targeting moieties, such as peptides, so as to obtain a cell-permeable targeting probe.

A "primary targeting moiety" as used in the present invention relates to the part of the targeting probe which binds to a primary target. Particular examples of primary targeting moieties are peptides or proteins which bind to a receptor. Other examples of primary targeting moieties are antibodies or fragments thereof which bind to a cellular compound. Antibodies can be raised to non-proteinaceous compounds as well as to proteins or peptides. Other primary targeting moieties can be made up of aptamers, oligopeptides, oligonucleotides, oligosaccharides, as well as peptoids and organic drug compounds. A primary targeting moiety preferably binds with high specificity, with a high affinity, optionally even covalently, and the bond with the primary target is preferably stable within the body.

In order to allow specific targeting of the above-listed primary targets, the primary targeting moiety of the targeting probe can comprise compounds including but not limited to antibodies, antibody fragments, e.g. Fab2, Fab, scFV, diabodies, polymers (tumor targeting by virtue of EPR effect), proteins, peptides, e.g. octreotide and derivatives, VIP, MSH, LHRH, chemotactic peptides, bombesin, elastin, peptide mimetics, carbohydrates, monosaccharides, polysaccharides, viruses, whole cells, phage, drugs, chemotherapeutic agents, receptor agonists and antagonists, cytokines, hormones, steroids. Examples of organic compounds envisaged within the context of the present invention are, or are derived from, estrogens, e.g. estradiol, androgens, progestins, corticosteroids, paclitaxel, etoposide, doxorubricin, methotrexate, folic acid, and cholesterol.

According to a particular embodiment of the present invention, the primary target is a receptor and suitable primary targeting moieties include but are not limited to, the ligand of such a receptor or a part thereof which still binds to the receptor, e.g. a receptor binding peptide in the case of receptor binding protein ligands.

Other examples of primary targeting moieties of protein nature include interferons, e.g. alpha, beta, and gamma interferon, interleukins, and protein growth factor, such as tumor growth factor, e.g. alpha, beta tumor growth factor, platelet-derived growth factor (PDGF), uPAR targeting protein, apolipoprotein, LDL, annexin V, endostatin, and angiostatin.

Alternative examples of primary targeting moieties include DNA, RNA, PNA and LNA which are e.g. complementary to the primary target.

According to a particular embodiment of the invention, small lipophilic primary targeting moieties are used which can bind to an intracellular primary target.

According to a further particular embodiment of the invention, the primary target and primary targeting moiety are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting primary targets with tissue-, cell- or disease-specific expression. For example, membrane folic acid receptors mediate intracellular accumulation of folate and its analogs, such as methotrexate. Expression is limited in normal tissues, but receptors are overexpressed in various tumor cell types.

According to one embodiment, the Pre-targeting Probe and the Effector Probe can be multimeric compounds, comprising a plurality of primary and/or secondary targets and/or targeting moieties. These multimeric compounds can be polymers, dendrimers, liposomes, polymer particles, or other polymeric constructs. Of particular interest for amplifying the signal of detection are targeting probes with more than one secondary target, which allow the binding of several Effector Probes.

The Pre-targeting Probe further comprises the above-mentioned first Bio-orthogonal Reactive group. This group serves as a "secondary target", i.e. as the part of the targeting probe that provides the first reaction partner for the retro Diels-Alder coupling chemistry.

Said secondary target—can be either partner of the coupling reaction, as described above. I.e. in one embodiment it is an electron-deficient tetrazine. In another embodiment it is an axially substituted TCO of the above formula (1).

In the Pre-targeting Probe, the primary targeting moiety and the first Bio-orthogonal Reactive Group can be directly linked to each other. They can also be bound to each other via a linker, and furthermore they can both be linked to a primary targeting scaffold, e.g. a biopolymer such as a polypeptide. I.e. in the most simple sense, the Linker Moiety is a bond. Suitable Linker Moieties further include, but are not limited to polyethylene glycol (PEG) chains varying from 2 to 200, particularly 3 to 113 and preferably 5-50 repeating units. By adjusting the PEG chain length, one can influence the circulation time of the probes in the physiological system. This is of particular relevance for the Pre-targeting Probe (as the initial targeting step of linking the primary targeting moiety to the primary target may involve a relatively slow process, requiring a relatively lengthy circulation time). Linker moieties optionally include biopolymer fragments, such as oligo- or polypeptides or polylactides.

It will be understood that the invention encompasses any conceivable manner in which the diene and the dienophile are attached to either of the pre-targeting or effector probes. Methods of affecting conjugation to these probes, e.g. through reactive amino acids such as lysine or cysteine, are known to the skilled person.

Effector Probe

An Effector Probe comprises an Effector Moiety that is capable of providing the desired diagnostic, imaging, and/or therapeutic effect. The Effector Probe further comprises a secondary targeting moiety.

The secondary targeting moiety relates to the part of the Effector Probe that forms the reaction partner for the available secondary target, i.e. the Bio-orthogonal Reactive Group (or groups) comprised in the Pre-targeting Probe. It will be understood that, to the extent that the secondary target is an Axially substituted TCO of formula (1) as defined above, the secondary targeting moiety will be a diene such as a tetrazine, and vice versa.

The Effector Moiety can, e.g., be a detectable label. A "detectable label" as used herein relates to the part of the Effector Probe which allows detection of the probe, e.g. when present in a cell, tissue or organism. One type of detectable label envisaged within the context of the present invention is a contrast providing agent. Different types of detectable labels are envisaged within the context of the present invention and are described hereinbelow.

Thus, according to a particular embodiment of the present invention, the pretargeting kits and methods of the present invention are used in imaging, especially medical imaging. In order to identify the primary target, use is made, as the Effector Probe, of an imaging probe comprising one or more detectable labels. Particular examples of detectable labels of the imaging probe are contrast-providing moieties used in traditional imaging systems such as MRI-imageable constructs, spin labels, optical labels, ultrasound-responsive constructs, X-ray-responsive moieties, radionuclides, (bio) luminescent and FRET-type dyes. Exemplary detectable labels envisaged within the context of the present invention include, and are not necessarily limited to, fluorescent molecules, e.g. autofluorescent molecules, molecules that fluoresce upon contact with a reagent, etc., radioactive labels; biotin, e.g., to be detected through binding of biotin by avidin; fluorescent tags, imaging constructs for MRI comprising paramagnetic metal, imaging reagents, e.g., those described in U.S. Pat. Nos. 4,741,900 and 5,326,856) and the like. The radionuclide used for imaging can be, for example, an isotope selected from the group consisting of $^{3}H$, $^{11}C$, $^{13}N$, $^{15}O$, $^{18}F$, $^{19}F$, $^{51}Cr$, $^{52}Fe$, $^{52}Mn$, $^{55}Co$, $^{60}Cu$, $^{61}Cu$, $^{62}Zn$, $^{62}Cu$, $^{63}Zn$, $^{64}Cu$, $^{66}Ga$, $^{67}Ga$, $^{68}Ga$, $^{70}As$, $^{71}As$, $^{72}As$, $^{74}As$, $^{75}Se$, $^{75}Br$, $^{76}Br$, $^{77}Br$, $^{80}Br$, $^{82}Br$, $^{82}Rb$, $^{86}Y$, $^{88}Y$, $^{89}Sr$, $^{89}Zr$, $^{97}Ru$, $^{99}Tc$, $^{110}In$, $^{111}In$, $^{113}In$, $^{114}In$, $^{117}Sn$, $^{120}I$, $^{122}Xe$, $^{123}I$, $^{124}I$, $^{125}I$, $^{166}Ho$, $^{167}Tm$, $^{169}Yb$, $^{193}Pt$, $^{195}Pt$, $^{201}Tl$, and $^{203}Pb$.

Other elements and isotopes, such as being used for therapy may also be applied for imaging in certain applications.

The MRI-imageable moiety can be, for example, a paramagnetic ion or a superparamagnetic particle. The paramagnetic ion can be an element selected from the group consisting of Gd, Fe, Mn, Cr, Co, Ni, Cu, Pr, Nd, Yb, Tb, Dy, Ho, Er, Sm, Eu, Ti, Pa, La, Sc, V, Mo, Ru, Ce, Dy, Tl. The ultrasound responsive moiety can comprise a microbubble, the shell of which consisting of a phospholipid, and/or (biodegradable) polymer, and/or human serum albumin. The microbubble can be filled with fluorinated gasses or liquids.

The X-ray-responsive moieties include but are not limited to iodine, barium, barium sulfate, gastrografin or can comprise a vesicle, liposome or polymer capsule filled with iodine compounds and/or barium sulfate.

Moreover, detectable labels envisaged within the context of the present invention also include peptides or polypeptides that can be detected by antibody binding, e.g., by binding of a detectable labeled antibody or by detection of bound antibody through a sandwich-type assay. In one embodiment the detectable labels are small size organic PET and SPECT labels, such as $^{18}F$, $^{11}C$ or $^{123}I$. Due to their small size, organic PET or SPECT labels are ideally suited for monitoring intracellular events as they do not greatly affect the properties of the targeting device in general and its membrane transport in particular. An imaging probe comprising a PET label and either of the retro Diels-Alder active moieties as a secondary targeting moiety is lipophilic and able to passively diffuse in and out of cells until it finds its binding partner. Moreover, both components do not preclude crossing of the blood brain barrier and thus allow imaging of regions in the brain.

When the Effector Probe is intended to comprise a detectable label based on a metal, such as a lanthanide (e.g. Gd) for MRI contrast enhancement, such is preferably provided in the form of a chelate. In such a case the Effector Probe preferably comprises a structural moiety capable of forming a coordination complex with such a metal. A good example hereof are macrocyclic lanthanide(III) chelates derived from 1,4,7,10-tetraazacyclododecane-1,4,7,10-tetraacetic acid (H$_4$ dota), and 1,4,7,10-tetraazacyclododecane-α,α',α,"α'"-tetramethyl-1,4,7,10-tetraacetic acid (H$_4$ dotma).

The Effector Moiety can also be a therapeutic moiety such as a pharmaceutically active compound. Examples of pharmaceutically active compounds are provided herein. A therapeutic probe can optionally also comprise a detectable label.

Thus, according to another embodiment, the pretargeting kits and methods of the invention are used for targeted therapy. This is achieved by making use of an Effector Probe comprising a secondary targeting moiety and one or more pharmaceutically active agents (i.e. a drug or a radioactive isotope for radiation therapy). Suitable drugs for use in the context of targeted drug delivery are known in the art. Optionally, the therapeutic probe can also comprise a detectable label, such as one or more imaging agents. A radionuclide used for therapy can be, for example, an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{111}$In, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac.

Alternatively, the drug in the therapeutic probe is selected from sensitizers for photodynamic therapy.

Alternatively the therapeutic probe comprises a recognition moiety that binds to therapeutic entities in vivo, such as T cells, natural killer cells, or other endogenous constructs such as proteins.

In the Effector Probe, the secondary targeting moiety, i.e. the second Bio-orthogonal Reactive Group and the effector moiety can be directly linked to each other. They can also be bound to each other via a linker, and furthermore they can both be linked to a secondary targeting scaffold. The linker can, independently, be selected from the same moieties, e.g. poly ethylene glycols, as discussed above. The secondary targeting scaffold can be e.g. a biopolymer such as a polypeptide.

The invention also relates to a pre-targeting method, using the retro Diels-Alder reaction. Herein a Pre-targeting Probe comprising a primary targeting moiety (e.g., an antibody, and antibody fragment, or a receptor binding peptide), functionalized with a suitable diene, preferably a compound according to any one of the formulae (2)-(5) mentioned above, or with a cyclooctene according to formula (1) above, respectively, is injected into a subject. After binding to the target (e.g. a primary or metastatic tumor lesion, an atherosclerotic plaque, an infracted area, an inflammation or infection site, etc.) and clearance from the circulation and from non-target tissues (e.g. blood, liver, spleen, kidney, etc.) an Effector Probe comprising a secondary targeting moiety, e.g. carrying an E-cyclooctene or tetrazine derivative, respectively (i.e. the reactive counterpart of the Bio-orthogonal Reactive Group present in the Pre-targeting Probe), and a drug or an imageable label, is injected. The Effector Probe binds to the primary targeting moiety and provides high contrast or selectively treats the disease site.

The invention also relates to the targeting of a general metabolic pathway, which is upregulated during a disease (like infection or cancer) such as DNA, protein, and membrane synthesis and carbohydrate uptake. Suitable probes comprise diene or dienophile labeled amino acids, sugars, nucleic acids and choline, analogous to the metabolic tracers currently used in the art, [$^{11}$C]-methionine, [$^{18}$F]-fluorodeoxyglucose (FDG), deoxy-[$^{18}$F]-fluorothymidine (FLT) and [$^{11}$C]-choline. Cells with a high metabolism or proliferation have a higher uptake of these building blocks. In this method, e.g. tetrazine- or E-cyclooctene derivatives enter these or other pathways and accumulate in and/or on cells. After sufficient build-up and clearance of free probe a detectably labeled or drug-carrying (cell permeable) tetrazine probe or E-cyclooctene probe (or probes carrying other dienes/dienophiles according to the invention) is sent in to bind the accumulated E-cyclooctene, respectively tetrazine metabolite. As an advantage over normal FDG (fluorine 18 fluorodeoxyglucose)-type imaging, ample time is available to allow high build up of the targeting moiety before radioactivity is sent in, thus increasing the target to non-target ratio. Alternatively, a metabolic pathway and/or metabolite that is specific for a disease can be targeted.

The invention also relates to the pre-targeting of intracellular targets. Due to their small size, organic PET labels ($^{18}$F, $^{11}$C) are ideally suited for monitoring intracellular events as they do not greatly affect the properties of the targeting device in general and its membrane transport in particular (contrary to the large and polar radiometal-chelate construct conjugates). Although the substituted tetrazine moiety and the E-cyclooctene used in the invention are not necessarily small, they are relatively nonpolar and can be used for intracellular imaging of proteins, mRNA, signaling pathways etc. The secondary (e.g. PET labeled) substituted tetrazine moiety or E-cyclooctene probe (i.e. the Effector Probe) is capable of passively diffusing in and out of cells until it finds its binding partner or is subject to an active uptake mechanism. These properties also allow the use of retro Diels-Alder reaction for pre-targeting in the brain, as both components do not preclude crossing of the blood brain barrier.

The invention also pertains to pretargeted signal amplification and/or polyvalency installation. At least one primary targeting device is conjugated to a dendrimer, polymer, or nanoparticle containing multiple tetrazine moieties. After receptor binding, a (one or more) cyclooctene conjugated to one or more contrast moieties for nuclear imaging (e.g., a radiometal chelate, a radiohalogen, etc.) or MRI (e.g., Gd chelates) is injected. The subsequent retro Diels-Alder reaction results in a high concentration of MRI contrast agent at the target tissue. Furthermore, the polyvalency at the target site will increase the reaction kinetics with the Axially substituted TCO effector conjugate, affording an efficient target accumulation of for example MRI contrast agents. Naturally, the Axially substituted TCO can also be used in the targeting device conjugate and the tetrazine (or other diene of the invention) conjugated to the reporter.

Conjugation Route and Kits

The invention further pertains to the use of the retro Diels-Alder reaction as a route for the conjugation of imaging agents and drugs to targeting constructs such as peptides. The effector can contain organic PET or SPECT nuclide labeled prosthetic groups, metal complexes for PET/SPECT/MRI and microbubbles for ultrasound imaging, fluorophores for optical imaging, but also α and β$^-$ emitters for radiotherapy and, in general, a cytotoxic anticancer agent. The imaging/therapy agents can be functionalized with a pendant tetrazine or other suitable diene moiety and the targeting group with an Axially substituted TCO derivative, or vice versa.

The present route is especially advantageous for agents for nuclear imaging and radiotherapy: in view of the decay of the radionuclide it is beneficial to conduct the most time-consuming step (the actual targeting in the body of a subject) as a pre-targeting step. The selection, according to the invention, of Axially substituted TCO, to attain the above-described very rapid retro Diels-Alder chemistry for the secondary targeting, allows for using a broad range of radionuclides, including shorter lived ones than with existing methods. Axially substituted TCO functionalized Effector Probes and suitable dienes, e.g., tetrazine carrying Pre-targeting Probes can be coupled at extremely low concentrations in vivo without the need for sustained blood circulation of the effector moiety (such as the radionuclide). It will be understood that this equally holds for Axially substituted TCO carrying Pre-targeting Probes combined with diene, particularly tetrazine, functionalized Effector Probes. Moreover, the reactive groups are advantageously stable, and thus present a longer lived reactivity, without being too easily prone to side reactions.

It will be understood that the foregoing provides advantages such as minimizing the radiation dose to the patient. Also, it leads to allowing the usage of PET i.e. Positron Emission Tomography agents instead of SPECT i.e. Single Photon Emission Computerized Tomography agents. Furthermore, the increased reactivity allows applications at lower concentrations in vivo.

The present invention is particularly suitable for use in multimodal imaging, optionally using different imaging agents to visualize the same target. Alternatively the imaging probe comprises at least 2 different labels to enable multimodal imaging.

The application of the improved [4+2] retro Diels-Alder chemistry of the invention in molecular imaging opens up pre-targeting to all types and sizes of targeting constructs. This allows intracellular and metabolic imaging to profit from the high target accumulation and low background, attainable through pre-targeting build-up. Likewise, pretargeted signal amplification schemes, e.g. polytetrazine and/or polyalkene dendrimers or liposomes, become available for smaller and more diverse targeting devices.

As the reaction partners are abiotic and bio-orthogonal, pre-targeting using the [4+2] retro Diels-Alder reaction using Axially substituted TCO as the dienophile as described above, is not hampered by endogenous competition and metabolism/decomposition, and affords a stable covalent bond. Choosing a target metabolic pathway, and the corresponding tetrazine-metabolite derivative by virtue of its high flux in, for example, tumor cells compared to normal cells, affords the installation of a high density of artificial tetrazine receptors or other chemical handles in cells or on the surfaces of target cells, circumventing the use of endogenous cell surface receptors which can sometimes be at low levels.

Further particular embodiments of the present invention relate to kits comprising a metabolic precursor and an imaging probe, more particularly an imaging probe comprising a detectable label, which is a contrast agent used in traditional imaging systems. Such a detectable label can be but is not limited to a label selected from the group consisting of MRI-imageable constructs, spin labels, optical labels, ultrasound-responsive agents, X-ray-responsive agents, radionuclides, and FRET-type dyes. In a particular embodiment of the present invention, use is made of reporter probes. Such a reporter probe can be the substrate of an enzyme, more particularly an enzyme which is not endogenous to the cell, but has been introduced by way of gene therapy or infection with a foreign agent. Non-endogenous as referring to a gene in a cell or tissue herein is used to indicate that the gene is not naturally present and/or expressed in that cell or tissue. Alternatively, such a reporter probe is a molecule which is introduced into the cell by way of a receptor or a pump, which can be endogenous or introduced into the cell by way of gene therapy or infection with a foreign agent. Alternatively, the reporter probe is a molecule which reacts to certain (changing) conditions within a cell or tissue environment.

The invention also includes agents for use in the kits described above. One such agent is a pretargeting agent comprising a primary targeting moiety and a bio-orthogonal reactive group, wherein the bio-orthogonal reactive group is a reaction partner for a [4+2] retro Diels-Alder reaction. Particular reaction partners are described hereinbefore, i.e. generally either an electron-deficient tetrazine or other suitable diene as discussed above, or an axially substituted cyclooctene in accordance with the invention. The invention also relates to the use of these agents in targeted medical imaging or targeted therapy, and to said agents for use in such a method. Particularly, the invention relates to these use of these agents in a pretargeting method, and to these agents for use in such a method. Another such agent is an imaging probe comprising a detectable label and a bio-orthogonal reactive group, wherein the bio-orthogonal reactive group is a reaction partner for a [4+2] retro Diels-Alder reaction.

The invention also relates to an imaging probe comprising a detectable label and a bio-orthogonal reactive group, wherein the bio-orthogonal reactive group is a reaction partner for a [4+2] retro Diels-Alder reaction. The invention further relates to a therapeutic probe comprising a pharmaceutically active compound and a bio-orthogonal reactive group, wherein the bio-orthogonal reactive group is a reaction partner for a [4+2] retro Diels-Alder reaction.

Part of the invention is also a pretargeting method comprising administering a pretargeting agent as described above to a subject and allowing the agent to circulate in the subject's system for a period of time effective to achieve binding of the primary targeting moiety to a primary target, followed by clearing non-bound agent from the body. A typical time period for this is 12 to 96 hours, particularly around 48 hours.

Further, the invention provides an imaging method comprising conducting a pretargeting method as described above, followed by the administration of an imaging probe also according to the invention, wherein the bio-orthogonal reactive groups in the pretargeting agent and in the imaging probe together form the reactive partners for the [4+2] retro Diels-Alder reaction. Similarly, the invention provides a method of targeted medical treatment in a subject, comprising conducting a pretargeting method as described above, followed by the administration of a therapeutic probe also according to the invention, wherein the bio-orthogonal reactive groups in the pretargeting agent and in the imaging probe together form the reactive partners for the [4+2] retro Diels-Alder reaction.

The invention also pertains to the aforementioned pretargeting agents for use in an imaging or therapeutic method as described above.

In summary, on the basis of retro Diels-Alder chemistry, bio-orthogonal pretargeted molecular imaging and therapy serves to bring great advantages to patients. On one side, it serves to afford the acquisition of superior images of target tissues such as cancer and cardiovascular lesions. On the other hand, the intrinsic side effects deriving from the administration of radioactive compounds and, in general, potentially toxic drugs can be greatly diminished while increasing the effective dose that reaches a diseased tissue. Furthermore, it will greatly expand the collection of traceable molecular events that underlie disease. In particular, this technology can give access to target tissues far from blood vessels and will facilitate imaging of the information-rich intracellular environment.

The invention will be illustrated with reference to the following, non-limiting Examples and the accompanying non-limiting Figures.

EXAMPLES

Materials

All reagents and solvents were obtained from commercial sources (Sigma-Aldrich, Acros, ABCR, Invitrogen, and Merck for reagents, Biosolve, Merck and Cambridge Isotope Laboratories for normal and deuterated solvents) and used without further purification unless stated otherwise. 1-Amino-3,6,9,12,15,18,21,24,27,30,33,36-dodecaoxanon-atriacontan-39-oic acid (21) was obtained from Polypure. [$^{111}$In]Indium chloride and sodium [$^{125}$I]iodide solutions were purchased from PerkinElmer. Water was distilled and deionized (18 MΩcm) by means of a milli-Q water filtration system (Millipore). The labeling buffers were treated with Chelex-100 resin (BioRad Laboratories) overnight, then filtered through 0.22 µm and stored at 4° C. Iodogen iodination tubes, kits for bicinchoninic acid (BCA) assay, gelcode blue protein staining solutions and Zeba desalt spin columns (40 kDa MW cut-off, 0.5-2 mL) were purchased from Pierce Protein Research (Thermo Fisher Scientific). Tablets to prepare phosphate buffered saline (PBS) pH 7.4 were acquired from Calbiochem (Merck). Amicon Ultra-4 and Ultra-15 centrifugal filter units (50 kDa MW cut-off) were purchased from Millipore. Mouse serum was purchased from Innovative Research. Synthesis and radio labeling of tetrazine 28 was performed as described in Rossin et al., Angew Chem Int Ed 2010, 49, 3375.

Methods

NMR spectra were recorded in CDCl$_3$ or [D$_6$]DMSO, using a Bruker DPX300 spectrometer or a Bruker Avance600 spectrometer. $^{13}$C NMR multiplicities (q=quaternary, t=tertiary, s=secondary and p=primary) were distinguished using a DEPT pulse sequence. High-resolution ESI mass spectra (HRMS) were recorded on an Agilent ESI-TOF mass spectrometer, measuring in the positive ion mode.

Preparative column chromatography was performed on a Combiflash Companion apparatus (Teledyne Isco) using SiliCycle silica columns. Preparative HPLC was performed using an Agilent 1200 apparatus, equipped with a C18 Zorbax column (21.2×150 mm, 5 µm particles) applying a gradient of water and MeCN containing 0.1% TFA. Analytical radio-HPLC was carried out on an Agilent 1100 system equipped with a Gabi radioactive detector (Raytest). The samples were loaded on an Agilent Eclipse XDB-C18 column (4.6×150 mm, 5 µm particles), which was eluted at 1 mL/min with a linear gradient of MeCN in water containing 0.1% TFA (2 min at 10% MeCN followed by an increase to 45% MeCN in 11 min). The UV wavelength was preset at 254 nm. Size exclusion (SEC) HPLC was carried out on an Agilent 1200 system equipped with a Gabi radioactive detector. The samples were loaded on a BioSep-SEC-S 2000 column (300×7.8 mm, 5 µm particles, Phenomenex) and eluted with 20 mM phosphate, 150 mM NaCl, pH 6.8, at 1 mL/min. The UV wavelength was preset at 260 and 280 nm.

The $^{111}$In- and $^{177}$Lu-labeling yields were determined by radio-TLC, using ITLC-SG strips (Pall) eluted with 200 mM EDTA in 0.9% aq. NaCl and imaged on a phosphor imager (FLA-7000, Fujifilm). In these conditions, free $^{111}$In and $^{177}$Lu migrate with R$_f$=0.9, while $^{111}$In/$^{177}$Lu-tetrazine remains at the origin. The $^{125}$I-labeling yields were also determined with radio-TLC, using ITLC-SG strips eluted with a 1:1 MeOH/ethyl acetate mixture and imaged on a phosphor imager. In these conditions, free $^{125}$I and $^{125}$I-SHPP migrate with R$_f$=0.9, while $^{125}$I-mAbs remain at the origin.

Isoelectric focusing (IEF) analysis and SDS-PAGE were performed on a Phastgel system using IEF-3-9 gels and 7.5% PAGE homogeneous gels (GE Healthcare Life Sciences), respectively. The IEF calibration solution (broad PI, pH 3-10) was purchased from GE Healthcare and the protein MW standard solution (Precision Plus dual color standard) was purchased from BioRad. Upon electrophoresis, the gels were stained for 2 h with gelcode blue, destained overnight in water and then digitized with a conventional flat bed scanner.

The concentration of CC49 solutions was determined with a NanoDrop 1000 spectrophotometer (absorbance at 280 nm; Thermo Fisher Scientific) or with a BCA test.

LS174T tumor model. The human colon cancer cell line LS174T was obtained from the ATCC and maintained in Eagle's minimal essential medium (Sigma) supplemented with 10% heat inactivated fetal calf serum (Gibco), penicillin (100 U/mL), streptomycin (100 µg/mL) and 2 mM Glutamax. Nude female Balb/C mice (20-25 g body weight, Charles River Laboratories) were inoculated subcutaneously with 5×10$^6$ cells in 100 µL sterile PBS.

Example 1

As an example to link the tetrazine derived moiety to an antibody as outlined in FIG. 3a, a molecule 1 (see FIG. 5) is prepared. An example of a corresponding probe 2, derived from E-cyclooctene, is presented in FIG. 6. Both molecules contain PEG chains. Molecule 1 comprises an N-hydroxysuccimidyl moiety, that is used to couple the molecule with amino groups present in the antibody. The DOTA derived moiety in 2 can be used to carry a rare earth metal ion such as Gd for MR imaging or Lu-177 for nuclear imaging and therapy (SPECT).

Figure 5:
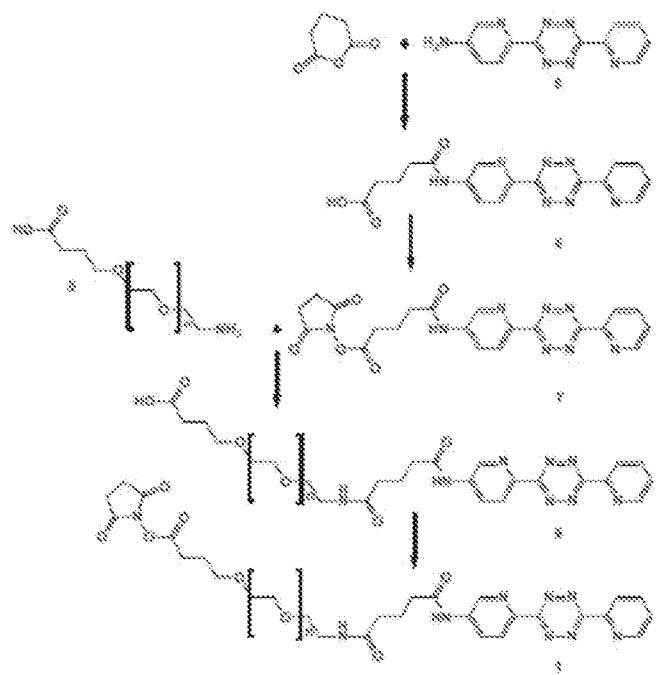
FIG. 5 to FIG. 10 illustrate synthesis schemes for compounds referred to in the Examples.

The synthesis of 1 is outlined in FIG. 5. The starting tetrazine derived molecule 5 is made according to Blackman et al. (Blackman, M L; Royzen, M; Fox, J M, Journal of The American Chemical Society, 2008, 130 (41), 13518-19). It is converted to the acid 6 by reaction with glutaric anhydride followed by formation of its N-hydroxysuccimidyl ester 7. This N-hydroxysuccimidyl ester is used to form acid 9 by reaction with the commercially available (IRIS biochem) PEG derivative 8 that in its turn is converted into its N-hydroxysuccimidyl ester 1.

Figure 6:
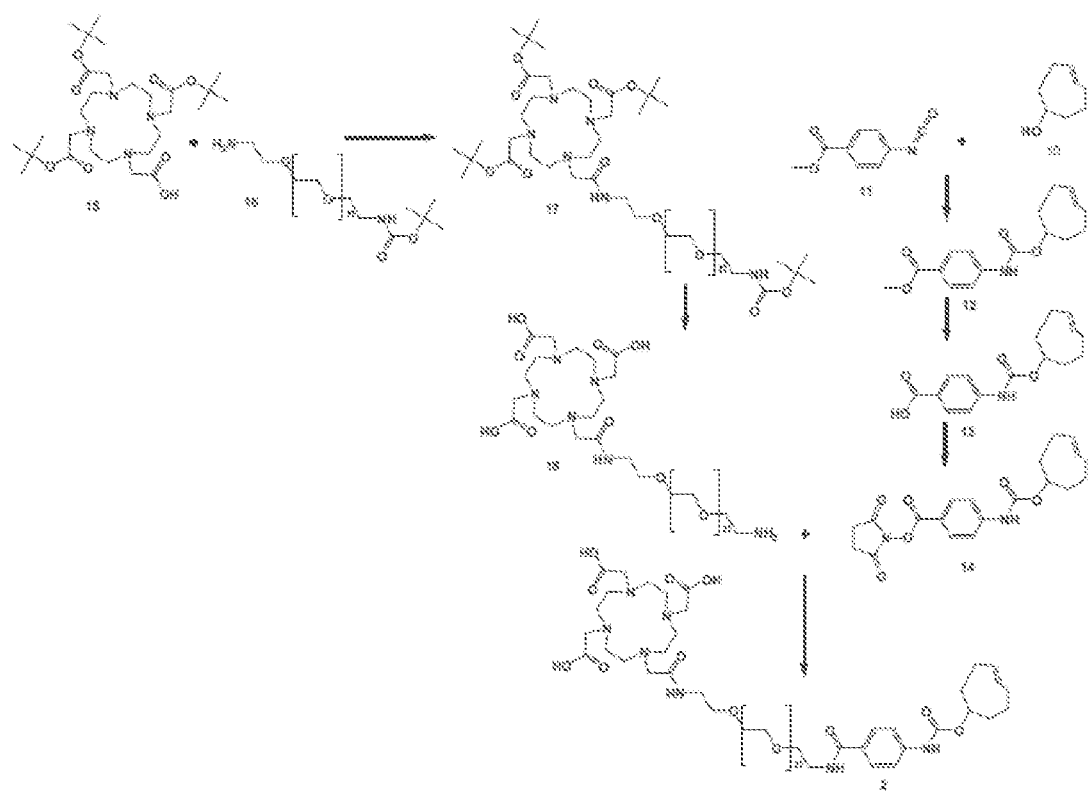

The synthesis of 2 is outlined in FIG. 6. (E)-cyclooct-4-enol (10) is prepared according to Yap et al. (Yap, G P A; Royzen, M; Fox, J M, Journal of The American Chemical Society, 2008, 130 (12), 3760-61). With the aid of the commercially available (Aldrich) isocyanate derivative 11 it is converted into ester 12, followed by saponification to acid 13. N-hydroxysuccimidyl ester 14 formed out of 13 is made to react with the DOTA and PEG derived amine 18 to form the final product 2. DOTA derivative 18 is prepared after deprotection of the 17 that in turn is prepared from the DOTA derivative 15 and PEG derivative 16, both available commercially (from Macrocyclics and IRIS Biotech, respectively).

Example 2

Figure 7:
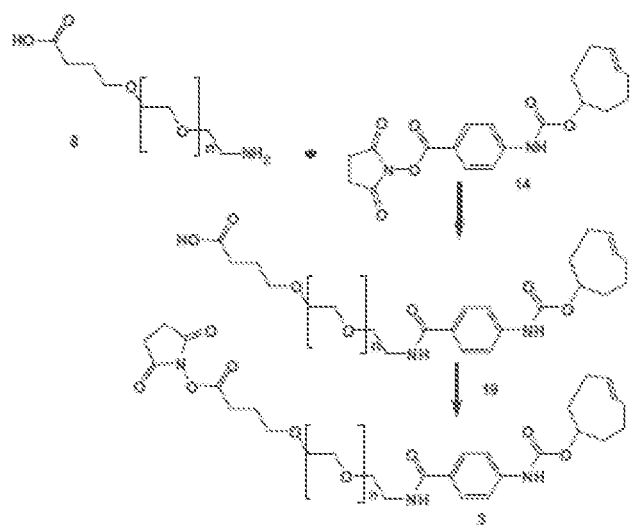

This example illustrates the inverse pair of molecules of Example 1, The E-cyclooctene derivative 3 meant to form the pretargeting moiety after conjugating to the antibody is shown in FIG. 7. The tetrazine/DOTA derived probe 4 that can serve as the Effector Probe as outlined in FIG. 3b, is shown in FIG. 8.

E-cyclooctene derivative 3 is formed by reaction of the commercially available (IRIS biochem) PEG derivative 8 (see also FIG. 5) with N-hydroxysuccimidyl ester 14 to form acid 19, followed by formation of the N-hydroxysuccimidyl derivative out of this acid (FIG. 7).

Figure 8:
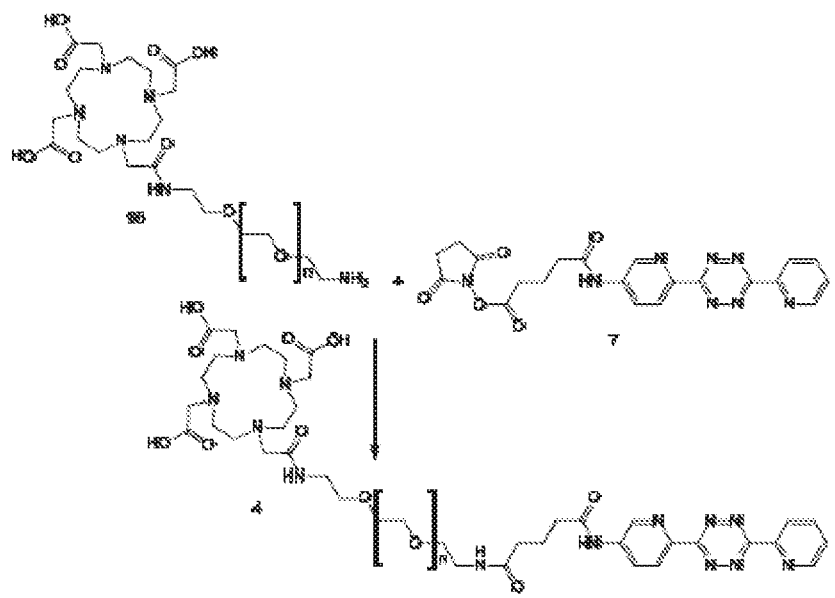

The synthesis of the tetrazine/DOTA derived probe 4 is outlined in FIG. 8. This probe is made by reaction of the DOTA and PEG derived amine 18 (see FIG. 6) with N-hydroxysuccimidyl ester 7 (see FIG. 5).

Example 3

Figure 9:
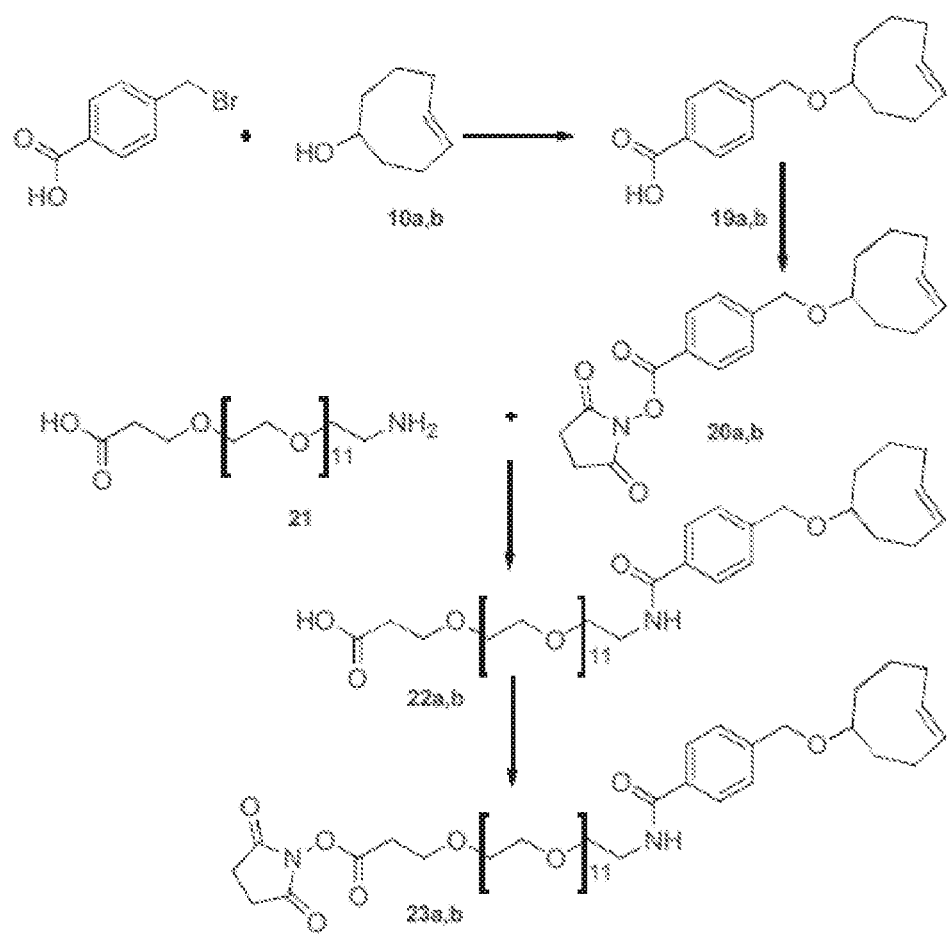

This example is illustrated in FIG. 9, which presents a scheme for the synthesis of (E)-2,5-dioxopyrrolidin-1-yl 1-(4-((cyclooct-4-en-1-yloxy)methyl)phenyl)-1-oxo-5,8,11,14,17,20,23,26,29,32,35,38-dodecaoxa-2-azahentetracontan-41-oate (TCO-O-PEG10-N-hydroxy succinimide (NHS), major and minor isomer, 23a and 23b, respectively).

The compounds denoted (number)a represent E-major and the compounds denoted (number)b represent E-minor.

(E-major)-2,5-Dioxopyrrolidin-1-yl 4-((cyclooct-4-enyloxy)methyl)benzoate (20a)

(E)-Cyclooct-4-enol (10a, major isomer containing approximately 13% of the Z-isomer) was synthesized according to a literature procedure (M. Royzen, G. P. A. Yap, J. M. Fox, J Am Chem Soc 2008, 130, 3760).

A 60% sodium hydride dispersion (1.8 g, 45 mmol) was added to an ice-bath-cooled solution of 10a (1.70 g, 13.5 mmol) in 60 mL DMF. After stirring for 4 h at room temperature, 4-bromomethylbenzoic acid (3.85 g, 17.9 mmol) was added in portions and the suspension was stirred overnight at room temperature. The mixture was poured into water (100 mL), tert-butyl methyl ether (100 mL) was added followed by 37% hydrochloric acid (5 mL). After separation, the aqueous layer was extracted with tert-butyl methyl ether (2×100 mL). The combined organic layers were washed with water (25 mL), dried over $MgSO_4$ and evaporated. The residue was passed through a thin silica layer with 4:1 hexane/ethyl acetate. The residue obtained after evaporation was dissolved in heptane (50 mL) at 70° C. and then cooled, affording 19a. The product was dissolved in dichloromethane (40 mL), N-hydroxysuccinimide (0.57 g, 4.9 mmol) was added, the mixture was cooled in an ice-bath, followed by addition of N,N'-dicyclohexylcarbodiimide (1.03 g, 4.99 mmol). After 30 min the ice-bath was removed and the reaction mixture was stirred at room temperature for 18 h. After filtration and evaporation, the residue was purified by column chromatography on silica using a gradient of ethyl acetate in heptane (0-15%). Next, the residue was dissolved in tert-butyl methyl ether (20 mL) and poured into heptane (50 mL), yielding 20a (1.42 g, 29%) as a white solid.

$^1$H NMR (300 MHz, $CDCl_3$): δ=8.10 (d, J=8.5 Hz, 2H), 7.45 (d, J=8.5 Hz, 2H), 5.60 (m, 1H), 5.34 (m, 1H), 4.54 (d, J=13.4 Hz, 1H), 4.47 (d, J=13.4 Hz, 1H), 3.09 (m, 1H), 2.91 (s, 4H), 2.43-1.40 (m, 10H); $^{13}$C NMR (75 MHz, $CDCl_3$): δ=169.0 (q), 161.5 (q), 146.7 (q), 135.1 (t), 132.1 (t), 130.4 (t), 127.0 (t), 123.7 (q), 85.3 (t), 68.0 (s), 40.5 (s), 37.7 (s), 34.2 (s), 32.7 (s), 31.4 (s), 25.4 (s); HRMS (ESI, m/z): Calculated for $C_{20}H_{23}NO_5Na^+$ ([M−Na]$^+$): 380.1474. Found: 380.1472.

(E-major)-2,5-Dioxopyrrolidin-1-yl 1-(4-((cyclooct-4-en-1-yloxy)methyl)phenyl)-1-oxo-5,8,11,14,17,20,23,26,29,32,35,38-dodecaoxa-2-azahentetracontan-41-oate (23a)

A solution of 20a (100 mg, 0.280 mmol) in dichloromethane (2 mL) was added dropwise to a solution of 21 (175 mg, 0.283 mmol) and triethylamine (290 μL, 2.08 mmol) in dichloromethane (2 mL) stirred in an ice-bath. The reaction mixture was stirred at room temperature for 16 h. The crude intermediate 22a obtained after evaporation was dissolved in dichloromethane (5 mL) and cooled in an ice bath. Bis(2,5-dioxopyrrolidin-1-yl)carbonate (170 mg, 0.664 mmol) and pyridine (28 μL, 0.35 mmol) were added and the reaction mixture was stirred at room temperature for 3 h. The mixture was filtered and evaporated and the product was purified by column chromatography on silica using a gradient of methanol in dichloromethane (5-10%) affording 23a as a viscous oil (119 mg, 39%).

$^1$H NMR (600 MHz, $CDCl_3$): δ=7.79 (d, J=8.2 Hz, 2H), 7.36 (d, J=8.2 Hz, 2H), 7.00 (s, 1H), 5.59 (m, 1H), 5.33 (m, 1H), 4.49 (d, J=12.5 Hz, 1H), 4.42 (d, J=12.5 Hz, 1H), 3.85 (t, J=6.5 Hz, 2H), 3.8-3.5 (m, 48H), 3.09 (m, 1H), 2.90 (t, J=6.5 Hz, 2H), 2.85 (s, 4H), 2.43-1.40 (m, 10H); $^{13}$C NMR (150 MHz, $CDCl_3$): δ=167.0 (q), 165.4 (q), 164.8 (q), 140.8 (q), 133.5 (t), 131.7 (q), 130.4 (t), 125.3 (t), 83.4 (t), 68.7 (s), 68.4 (s), 68.0 (s), 67.6 (s), 68.4 (s), 63.9 (s), 38.9 (s), 37.9 (s), 36.1 (s), 32.6 (s), 31.1 (s), 30.3 (s), 29.8 (s), 23.7 (s); HRMS (ESI, m/z): Calcd for $C_{47}H_{76}N_2O_{18}H^+$ ([M−H]$^+$): 957.5171. Found: 957.5174.

(E-minor)-2,5-Dioxopyrrolidin-1-yl 4-((cyclooct-4-enyloxy)methyl)benzoate (20b)

(E)-Cyclooct-4-enol (10b, minor isomer) was synthesized according to the aforementioned literature procedure. A 60% sodium hydride dispersion (2.1 g, 53 mmol) was added to an ice-bath-cooled solution of 10b (2.53 g, 20.1 mmol) in 50 mL tetrahydrofuran After stirring for 4 h at room temperature, the mixture was cooled again and 4-bromomethylbenzoic acid (4.53 g, 21.1 mmol) was added in portions over a 5 min. period. 25 ml of tetrahydrofuran were added and the suspension was stirred for 4 days at room temperature. Ice was added, followed by 12.0 g of citric acid. The mixture was extracted twice with 150 ml, tert-butyl methyl ether. The organic layers were washed with 25 mL water, dried and evaporated. The residue was purified by chromatography with 80 g silica gel and heptane containing a gradually increasing amount of ethyl acetate as the eluent. The product fractions (no full separation between product and starting alcohol) were combined and recrystallized from ca. 30 mL heptane (cooling to −15° C.), yielding 19b (0.86 g, 17%) as a white solid. It was dissolved in 40 mL dichloromethane. N-hydroxysuccinimide (0.48 g, 4.17 mmol) was added and the mixture was cooled in ice. N,N'-dicyclohexylcarbodiimide (0.80 g, 3.88 mmol) was added and the mixture was stirred for 30 min in ice, then 18 h at room temperature. Filtration, washing with dichloromethane, rotary evaporation and chromatography on 25 g silicagel using heptane-ethyl acetate as the eluent gave the product. The evaporated product fractions were mixed with 75 mL tert-butyl methyl ether and the mixture was warmed to 60° C. to give a solution. The solution was concentrated to 20 mL. Gradual addition of 50 mL heptane resulted in precipitation of the product. It was collected by filtration and washed with heptane to afford 1.05 g of 20b (15%).

1H NMR (300 MHz, CDCl$_3$): δ=8.10 (d, J=8.5 Hz, 2H), 7.46 (d, J=8.5 Hz, 2H), 5.73 (m, 1H), 5.52 (m, 1H), 4.60 (d, J=13.4 Hz, 1H), 4.45 (d, J=13.4 Hz, 1H), 3.65 (m, 1H), 2.92 (s, 4H), 2.43-1.10 (m, 10H); $^{13}$C NMR (75 MHz, CDCl$_3$): δ=169.0 (q), 161.5 (q), 146.7 (q), 135.1 (t), 132.1 (t), 130.4 (t), 127.0 (t), 123.7 (q), 85.3 (t), 68.0 (s), 40.5 (s), 37.7 (s), 34.2 (s), 32.7 (s), 31.4 (s), 25.4 (s); HRMS (ESI, m/z): Calcd for C$_{20}$H$_{23}$NO$_5$Na$^+$ ([M−Na]$^+$): 380.1474. Found: 380.1472.

(E-minor)-2,5-Dioxopyrrolidin-1-yl 1-(4-((cyclooct-4-en-1-yloxy)methyl)phenyl)-1-oxo-5,8,11,14,17,20,23,26,29,32,35,38-dodecaoxa-2-azahentetracontan-41-oate (23b)

This compound was made in a similar way as 23a, starting from 20b. 23b was obtained as a viscous oil in 93% yield.
$^1$H NMR (300 MHz, CDCl$_3$): δ=7.80 (d, J=8.2 Hz, 2H), 7.43 (d, J=8.2 Hz, 2H), 6.83 (s, 1H), 5.67 (m, 1H), 5.55 (m, 1H), 4.57 (d, J=12.5 Hz, 1H), 4.48 (d, J=12.5 Hz, 1H), 3.85 (t, J=6.5 Hz, 2H), 3.8-3.5 (m, 49H), 2.90 (t, J=6.5 Hz, 2H), 2.84 (s, 4H), 2.43-0.90 (m, 10H); $^{13}$C NMR (75 MHz, CDCl$_3$): δ=169.2.0 (q), 167.6.4 (q), 167.0 (q), 143.4 (q), 136.2 (t), 133.8 (q), 131.6 (t), 127.4 (t), 127.1 (t), 74.7 (t), 71.1 (s), 70.9 (s), 70.6 (s), 70.2 (s), 70.1 (s), 66.1 (s), 40.5 (s), 40.1 (s), 34.9 (s), 33.3 (s), 32.5 (s), 30.2 (s), 28.0 (s), 25.9 (s); HRMS (ESI, m/z): Calcd for C$_{47}$H$_{76}$N$_2$O$_{18}$H$^+$ ([M−H]$^+$): 957.5171. Found: 957.5179.

Example 4

Figure 10:
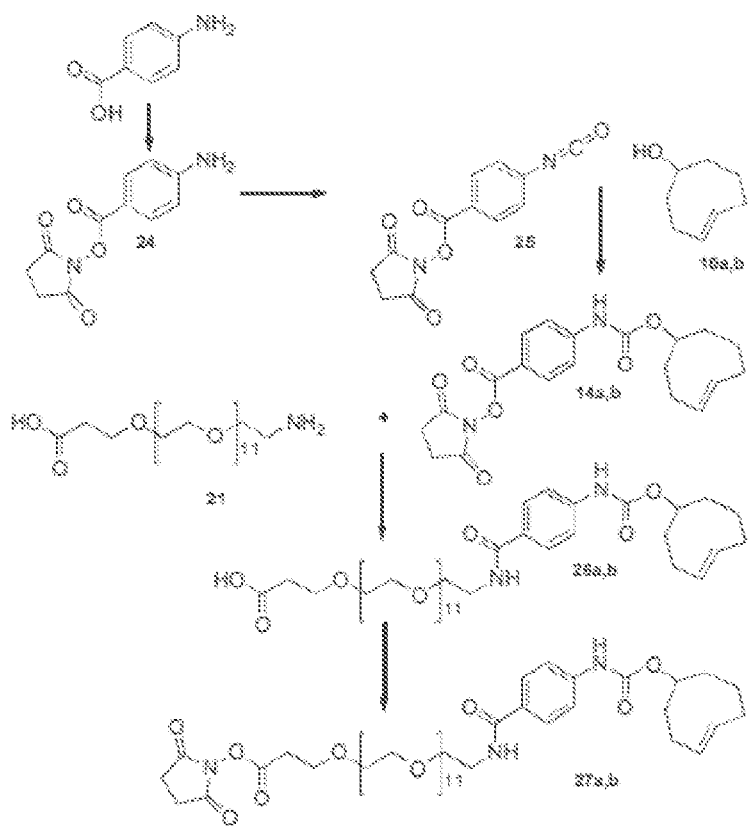
Figure 11:
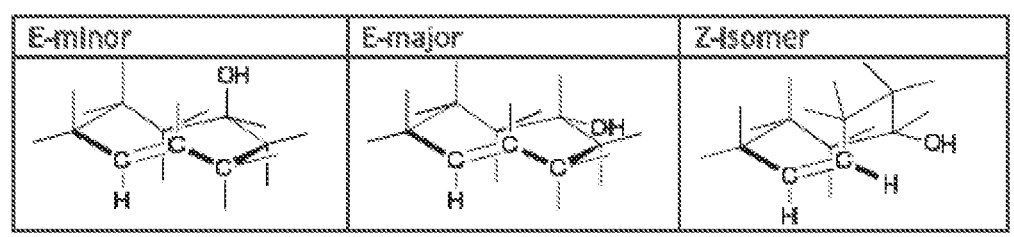
FIG. 11 shows a comparison, showing the stereochemistry, of E-minor and E-major isomers discussed below, and the Z isomer, of cyclooctenol.

This example is illustrated in FIG. 10, which presents a reaction scheme for the synthesis of (E)-2,5-dioxopyrrolidin-1-yl 1-(4-(((cyclooct-4-en-1-yloxy)carbonyl)amino)phenyl)-1-oxo-5,8,11,14,17,20,23,26,29,32,35,38-dodecaoxa-2-azahentetracontan-41-oate.

The compounds denoted (number)a represent E-major and the compounds denoted (number)b represent E-minor.

(E-major)-2,5-dioxopyrrolidin-1-yl 4-(((cyclooct-4-en-1-yloxy)carbonyl)amino)benzoate 14a N,N'-dicyclohexylcarbodiimide (9.50 g, 0.046 mol) was added in portions to a mixture of 4-aminobenzoic acid (5.84 g, 0.043 mol), N-hydroxysuccinimide (5.0 g, 0.044 mol) and 60 mL isopropanol, cooled in ice. After stirring for 16 hours at room temperature the suspension was filtered and the solid obtained stirred for another hour with 60 ml of isopropanol. The crude solid 24 obtained after filtration and drying under vacuum was mixed with 100 ml of dichloromethane and cooled in ice. After addition of 20% phosgene solution in toluene (26 mL, 49.4 mmol) and stirring for 30 minutes a solution was obtained. The solid obtained after evaporation was washed twice with 100 ml of toluene and dried under high vacuum. 4.03 g of 25 (36%) was obtained as a white solid. The solid was added in portions to a solution of 10a (1.40 g, 11.1 mmol) in 35 ml of dichloromethane. The suspension was stirred overnight, and then warmed for 2 h at 40° C. 1.77 g of 14a (41%) was obtained as a solid after elution with dichloromethane over silica followed by recrystallization from toluene. The product contained about 12% of the Z-isomer which could not be removed by chromatography or crystallization.
1H NMR (300 MHz, CDCl$_3$): δ=8.06 (d, J=8.8 Hz, 2H), 7.51 (d, J=8.8 Hz, 2H), 6.82 (m, 1H), 5.57 (m, 2H), 3.48 (m, 1H), 2.91 (s, 4H), 2.40 (m, 3H), 2.23-1.50 (m, 7H); $^{13}$C NMR (75 MHz, CDCl$_3$): δ=169.7 (q), 161.6 (q), 152.7 (q), 135.2 (t), 133.4 (t), 132.5 (t), 119.4.0 (q), 117.9 (t), 82.3 (t), 41.3 (s), 38.9 (s), 34.6 (s), 32.8 (s), 31.3 (s), 26.0 (s); HRMS (ESI, m/z): Calcd for C$_{20}$H$_{22}$N$_2$O$_6$Na$^+$ ([M−Na]$^+$): 409.1376. Found: 409.1372.

(E-major)-2,5-dioxopyrrolidin-1-yl 1-(4-(((cyclooct-4-en-1-yloxy)carbonyl)amino)phenyl)-1-oxo-5,8,11,14,17,20,23,26,29,32,35,38-dodecaoxa-2-azahentetracontan-41-oate 27a A solution of 14a (100 mg, 0.26 mmol) in dichloromethane (2 mL) was added dropwise to a solution of 21 (160 mg, 0.26 mmol) and triethylamine (400 μL, 2.9 mmol) in dichloromethane (2 mL) stirred in an ice-bath. The reaction mixture was stirred at room temperature for 16 h. The crude intermediate 26a obtained after evaporation was dissolved in dichloromethane (5 mL) and cooled in an ice bath. Bis(2,5-dioxopyrrolidin-1-yl)carbonate (89 mg, 0.35 mmol) and pyridine (28 μL, 0.35 mmol) were added and the reaction mixture was stirred at room temperature for 16 h. The mixture was filtered, extracted three times with 3 ml of water and once with 3 ml of brine. After drying over magnesium sulphate and evaporation 1.23 g of 27a (47%) was obtained as a viscous oil. $^1$H NMR (300 MHz, CDCl$_3$): δ=7.77 (d, J=8.7 Hz, 2H), 7.46 (d, J=8.7 Hz, 2H), 7.16 (s, 1H), 6.93 (s, 1H), 5.56 (m, 2H), 4.46 (m, 1H), 3.84 (t, J=6.5 Hz, 2H), 3.8-3.5 (m, 48H), 2.90 (t, J=6.5 Hz, 2H), 2.84 (s, 4H), 2.43-1.50 (m, 10H); $^{13}$C NMR (75 MHz, CDCl$_3$): δ=169.2 (q), 167.2 (q), 167.1 (q), 153.2 (q), 141.6 (q), 135.2 (t), 133.4 (t), 129.3 (q), 128.6 (t), 118.1 (t), 81.7 (s), 70.9 (s), 70.6 (s), 70.2 (s), 66.1 (s), 41.4 (s), 40.1 (s), 38.9 (s), 34.6 (s), 32.9 (s), 32.5 (s), 31.4 (s), 28.4 (s), 25.9 (s); HRMS (ESI, m/z): Calculated for C$_{47}$H$_{75}$N$_3$O$_{19}$H$^+$ ([M−H]$^+$): 986.5073. Found: 986.5085.

(E-minor)-2,5-dioxopyrrolidin-1-yl 4-(((cyclooct-4-en-1-yloxy)carbonyl)amino)benzoate 14b This compound was obtained in 32% yield in a similar way 14a was prepared, but starting from 10b. Because 10b was obtained pure, this product did not contain the Z-isomer.
1H NMR (300 MHz, CDCl$_3$): δ=8.04 (d, J=8.9 Hz, 2H), 7.55 (d, J=8.9 Hz, 2H), 7.11 (s, 1H), 5.61 (m, 2H), 5.05 (m, 1H), 2.92 (s, 4H), 2.36 (m, 4H), 2.23-1.20 (m, 6H); $^{13}$C NMR (75 MHz, CDCl$_3$): δ=169.8 (q), 161.6 (q), 152.7 (q), 144.6 (q), 135.7 (t), 132.5 (t), 132.1 (t), 119.4.0 (q), 118.0 (t), 72.1 (t), 41.3 (s), 34.6 (s), 32.9 (s), 30.3 (s), 28.5 (s), 26.0 (s); HRMS (ESI, m/z): Calcd for C$_{20}$H$_{22}$N$_2$O$_6$Na$^+$ ([M−Na]$^+$): 409.1376. Found: 409.1367.

(E-minor)-2,5-dioxopyrrolidin-1-yl 1-(4-(((cyclooct-4-en-1-yloxy)carbonyl)amino)phenyl)-1-oxo-5,8,11,14,17,20,23,26,29,32,35,38-dodecaoxa-2-azahentetracontan-41-oate 27b This compound was obtained in 89% yield in a similar way 27a was prepared, but starting from 14b.
$^1$H NMR (300 MHz, CDCl$_3$): δ=7.79 (d, J=8.7 Hz, 2H), 7.54 (d, J=8.7 Hz, 2H), 7.44 (s, 1H), 6.90 (m, 1H), 5.60 (m, 2H), 5.03 (m, 1H), 3.83 (t, J=6.5 Hz, 2H), 3.8-3.5 (m, 48H), 2.89 (t, J=6.5 Hz, 2H), 2.84 (s, 4H), 2.50-1.20 (m, 10H); $^{13}$C NMR (75 MHz, CDCl$_3$): δ=169.2.0 (q), 167.2 (q), 167.0 (q), 153.2 (q), 141.6 (q), 135.7 (t), 132.1 (t), 129.3 (q), 128.5 (t), 118.3 (t), 71.0 (s), 70.9 (s), 70.6 (s), 70.1 (s), 66.0 (s), 41.4 (s), 40.1 (s), 34.6 (s), 32.9 (s), 32.5 (s), 30.3 (s), 28.4 (s), 25.9 (s); HRMS (ESI, m/z): Calcd for $C_{47}H_{75}N_3O_{19}H^+$ ([M–H]$^+$): 986.5073. Found: 986.5058.

Example 5

Tetrazine Radiolabeling

Figure 12:
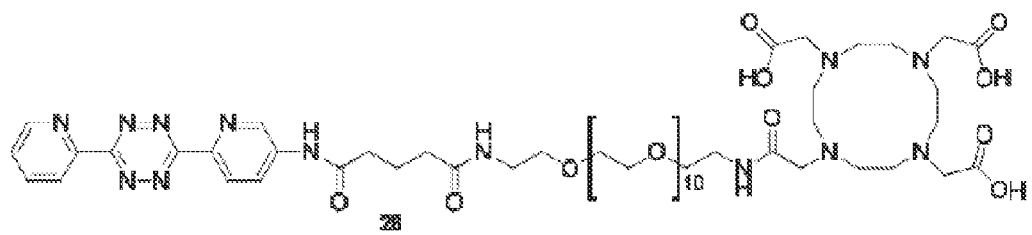
FIG. 12 shows the structure of tetrazine-DOTA probe 28

The DOTA-conjugated tetrazine (28; FIG. 12, described in Rossin et al. Angew Chem Int Ed 2010, 49, 3375) was dissolved (1 mg/mL) in 0.2M ammonium acetate pH 7.0 and stored at –80° C. before use. An aliquot of 28 was combined with a suitable amount of [$^{111}$In]indium chloride or [$^{177}$Lu] luthetium chloride and incubated for 10 min at 37° C. under gentle agitation. Then, 5 μL 10 mm DTPA was added and the solution was incubated for an additional 5 min. Carrier-added labeling reactions were carried out by adding 0.9 molar eq. InCl$_3$ or LuCl$_3$ with respect to the tetrazine. Typically, a quantitative labeling yield and a radiochemical purity greater than 98% were obtained with this method.

mAb Conjugation with Trans Cyclooctene (TCO) NHS Esters 14, 20, 23, 27

Herein, as well as in the subsequent steps, all compound numbers refer to both the a and the b isomers.

Typically, 1 mg CC49 (5 mg/mL solution in PBS) was modified with 0.6 molar (for kinetic measurements) or 10 molar eq. (for in vivo studies) of TCO-NHS constructs in a total volume of 250 μL PBS. The pH was adjusted to 9 with 1 M sodium carbonate buffer. The reactions were carried out under agitation for 30 min at RT in the dark. Subsequently, the TCO-modified mAbs were extensively washed with PBS using Amicon Ultra-15 centrifugal devices. The numbers of TCO groups per antibody were determined with a tetrazine titration, outlined below.

Tetrazine-DOTA 28 was radiolabeled with carrier-added $^{177}$Lu. mAb (25 μg) modified with ca. 0.6 molar eq. TCO was reacted with 3 molar eq. of $^{177}$Lu-28 (0.5 nM). mAb (25 μg) modified with ca. 10 molar eq. TCO was reacted with 15 molar eq. of $^{177}$Lu-28 (2.5 nM). The reactions were carried out in 50 μL PBS pH 7.4 at 37° C. for 10 min. The reaction mixtures were analyzed by SDS-PAGE and phosphor imager and the reaction yields were determined from the radioactivity in the bands corresponding to the mAb. The counts were quantified with AIDA Image Analyzer software (Raytest). The TCO-mAb conjugation yields were found to be in the range of 80-90%.

mAb Radiolabeling

To an adequate amount of sodium [$^{125}$I]iodide (5-15 MBq) in 50 μL PBS were added 1 μL of a 1 mg/mL solution of Bolton-Hunter reagent (N-succinimidyl-3-[4-hydroxyphenyl]propionate (SHPP)) in DMSO and 25 μL of a 4 mg/mL solution of chloramine-T (N-chloro 4-methylbenzenesulfonamide, sodium salt) in PBS. The resulting solution was mixed for 10-20 sec, 5 μL DMF and 100 μL toluene were added to the vial and $^{125}$I-SHPP was extracted in the organic phase, which was then transferred into a glass vial. The toluene was blown down under a gentle stream of N$_2$ after which the CC49-TCO solution (0.1-0.5 mg in 50-250 μL PBS) was added, the pH was adjusted to 9 with 1M carbonate buffer and the reaction mixture was incubated at RT for 30 min under gentle shaking After incubation, the labeling yield was determined by radio-ITLC. The crude reaction mixture was then loaded onto a Zeba spin desalting column, which was pre-equilibrated with saline solution. The reaction vial was rinsed with 20 μL saline solution and the rinse was loaded onto the column as well. After Zeba purification, the radiochemical purity of the $^{125}$I—CC49-TCO solution was determined by radio-ITLC, radio-HPLC and SDS-PAGE; the protein concentration was determined with a BCA assay.

Typically, greater than 70% $^{125}$I-SHPP mAb conjugation and a >98% radiochemical purity for the purified $^{125}$I—CC49-TCO species were obtained with this procedure.

Reaction Rates

Tetrazine-DOTA 28 was radiolabeled with carrier-added $^{177}$Lu at a specific activity of 3 MBq/μg. $^{177}$Lu-28 (33 nM) was reacted with increasing concentrations of CC49 modified with 1 eq. of TCO (0.33, 1, and 1.67 μM) in 200 μL PBS, pH 7.4 at 37° C. for 5 min. At selected times (15, 30, 45, 60, 90, 120, 180, and 300 sec) a 20 μL sample was withdrawn and quenched with tetrazine 6 (FIG. 5; described in Rossin et al. Angew Chem Int Ed 2010, 49, 3375) (1.5 μL, 5 mg/mL in DMF). Aliquots of each mixture were analyzed by SDS-PAGE and phosphor imager and the cycloaddition yields were determined from the radioactivity in the bands corresponding to the mAb. The counts were quantified with AIDA Image Analyzer software (Raytest).

TABLE 1

Second order kinetic constants of the reactions between CC49-TCO constructs and $^{177}$Lu-28. O = ether linked; C = carbamate linked

|  | No Spacer [M$^{-1}$s$^{-1}$] |  | PEG$_{10}$ Spacer [M$^{-1}$s$^{-1}$] |  |
|---|---|---|---|---|
| TCO O major | (20a) | 19600 ± 1400 | (23a) | 16500 ± 1400 |
| TCO O minor | (20b) | 136700 ± 2300 | (23b) | 156400 ± 3100 |
| TCO C major | (14a) | 11350 ± 550 | (27a) | 11030 ± 250 |
| TCO C minor | (14b) | 66550 ± 8800 | (27b) | 111600 ± 1800 |

Example 6

Trans-Cyclooctene Stability In Vivo

Tumor-free mice (n=3 per group) were injected intravenously with CC49-PEG$_{10}$-TCO-O major (CC49-23a; 8.4 TCO per CC49; 300 μg/100 μL per mouse), CC49-PEG$_{10}$-TCO-C minor (CC49-27b; 3.3 TCO per CC49, μg/100 μL per mouse), and CC49-TCO-O major without spacer (CC49-20a; 8.0 TCO per CC49, 300 μg/100 μL per mouse). At selected time points (from 1 hour up to 4 days post injection) blood samples were withdrawn from the vena saphena and collected in vials containing heparin. The blood samples were weighed and an excess $^{111}$In-tetrazine 28 was added. After 20 min incubation at 37° C., blood aliquots were 10-fold diluted with PBS and analyzed by SDS-PAGE. The cycloaddition yields were determined from the radioactivity in the bands corresponding to the mAb and the counts were quantified with AIDA Image Analyzer software. The amount of mAb present in blood at each time point (% ID/g blood) was evaluated in three separate groups of mice (n=3), which were injected with the corresponding $^{125}$I—CC49-TCO (300 μg/100 μL per mouse, ca. 0.2 MBq). The data, corrected for mAb clearance, were normalized to 100% ID TCO at t=0.

The results of this experiment indicate that, beside the physiological decrease of TCO due to mAb clearance from blood, in both groups of mice that were injected with constructs in which the TCO was conjugated to CC49 via a PEG$_{10}$ spacer there was a further decrease in the amount of circulating reactive TCO groups with time (FIGS. 12 A and B). This was not the case for the mice that were injected with a construct in which the TCO groups were conjugated to the mAb without a spacer (FIG. 12 C). This suggests a higher stability of the non spacer CC49-TCO constructs in vivo with respect to the CC49-PEG$_{10}$-TCO constructs.

Example 7

Biodistribution Experiments

Dual isotope biodistribution experiments were performed by injecting tumor bearing mice (n=3) intravenously with $^{125}$I-labeled CC49-TCO constructs with and without PEG$_{10}$ spacer (100 µg/100 µL per mouse, ca. 0.2 MBq) and, 24 or 72 h later, with $^{111}$In-tetrazine 28 (21 µg/75 µL per mouse, ca. 0.8 MBq). Three hours after tetrazine administration, the animals were anesthetized with isoflurane and sacrificed by cervical dislocation. Blood was withdrawn by heart puncture and organs and tissues of interest were harvested, blotted dry and weighed. The radioactivity of the samples was measured in a γ-counter along with standards to determine the % ID/gram. The energy windows were set to 10-80 keV and 100-510 keV for $^{125}$I and $^{111}$In, respectively. The distribution of the radiolabeled mAbs and of $^{111}$In-tetrazine is shown in Tables 2-5.

TABLE 2

Dual isotope biodistribution data 3 h after injection of $^{177}$Lu-tetrazine 28 (21 µg/75 µL per mouse, ca. 0.5 MBq), 27 h or 99 h after the administration of $^{125}$I-CC49-PEG$_{10}$-TCO-O major (CC49-23a; 100 µg/100 µL per mouse, ca. 0.2 MBq). Data presented as % ID/gram ± SD.

|  | 1 day pretargeting (n = 2) | | 4 days pretargeting (n = 2) | |
| --- | --- | --- | --- | --- |
|  | $^{125}$I-mAb | $^{177}$Lu-tetrazine | $^{125}$I-mAb | $^{177}$Lu-tetrazine |
| Blood | 5.55 ± 1.85 | 1.06 ± 0.34 | 0.23 ± 0.05 | 0.04 ± 0.01 |
| Tumor | 15.81 ± 0.22 | 3.09 ± 0.01 | 10.99 ± 4.24 | 0.86 ± 0.39 |
| Heart | 0.94 ± 0.09 | 0.20 ± 0.02 | 0.07 ± 0.01 | 0.04 ± 0.00 |
| Lung | 1.46 ± 0.31 | 0.32 ± 0.03 | 0.13 ± 0.03 | 0.13 ± 0.05 |
| Liver | 2.82 ± 1.56 | 0.61 ± 0.15 | 0.67 ± 0.16 | 0.31 ± 0.03 |
| Spleen | 1.21 ± 0.47 | 0.30 ± 0.09 | 0.38 ± 0.09 | 0.20 ± 0.00 |
| Kidney | 1.49 ± 0.40 | 1.73 ± 0.31 | 0.15 ± 0.03 | 1.73 ± 0.22 |
| Muscle | 0.32 ± 0.13 | 0.06 ± 0.03 | 0.03 ± 0.00 | 0.02 ± 0.01 |
| Bone | 0.47 ± 0.18 | 0.11 ± 0.02 | 0.06 ± 0.01 | 0.06 ± 0.01 |
| Brain | 0.18 ± 0.09 | 0.03 ± 0.02 | 0.01 ± 0.00 | 0.01 ± 0.00 |

TABLE 3

Single isotope biodistribution data 3 h after injection of $^{111}$In-tetrazine 28 (21 µg/75 µL per mouse, ca. 0.5 MBq), 27 h or 75 h after the administration of CC49-TCO-O major (CC49-20a; 100 µg/100 µL per mouse). Data presented as % ID/gram ± SD.

|  | 1 day pretargeting (n = 3) $^{111}$In-tetrazine | 3 days pretargeting (n = 2) $^{111}$In-tetrazine |
| --- | --- | --- |
| Blood | 2.39 ± 1.77 | 0.79 ± 0.39 |
| Tumor | 2.40 ± 0.16 | 3.11 ± 0.80 |
| Heart | 0.84 ± 0.71 | 0.30 ± 0.03 |
| Lung | 1.13 ± 0.55 | 0.58 ± 0.07 |
| Liver | 2.05 ± 1.03 | 0.88 ± 0.13 |
| Spleen | 0.83 ± 0.46 | 0.43 ± 0.03 |
| Kidney | 2.84 ± 0.35 | 3.16 ± 0.57 |
| Muscle | 0.33 ± 0.22 | 0.21 ± 0.02 |
| Bone | 0.33 ± 0.16 | 0.15 ± 0.00 |
| Brain | 0.10 ± 0.06 | 0.26 ± 0.11 |

TABLE 4

Dual isotope biodistribution data 3 h after injection of $^{111}$In-tetrazine 28 (21 µg/75 µL per mouse, ca. 0.5 MBq), 27 h or 75 h after the administration of $^{125}$I-CC49-TCO-C minor (CC49-14b; 100 µg/100 µL per mouse, ca. 0.2 MBq). Data presented as % ID/gram ± SD.

|  | 1 day pretargeting (n = 4) | | 3 days pretargeting (n = 4) | |
| --- | --- | --- | --- | --- |
|  | $^{125}$I-mAb | $^{111}$In-tetrazine | $^{125}$I-mAb | $^{111}$In-tetrazine |
| Blood | 5.09 ± 0.59 | 1.12 ± 0.09 | 1.82 ± 0.76 | 0.54 ± 0.11 |
| Tumor | 14.52 ± 2.46 | 2.59 ± 0.35 | 19.13 ± 5.99 | 2.76 ± 1.36 |
| Heart | 1.87 ± 0.55 | 0.46 ± 0.12 | 0.71 ± 0.28 | 0.24 ± 0.07 |
| Lung | 3.06 ± 1.08 | 0.79 ± 0.24 | 1.44 ± 0.49 | 0.50 ± 0.11 |
| Liver | 4.99 ± 1.51 | 1.17 ± 0.35 | 2.85 ± 0.50 | 0.84 ± 0.21 |
| Spleen | 2.20 ± 0.87 | 0.53 ± 0.14 | 1.14 ± 0.34 | 0.34 ± 0.09 |
| Kidney | 1.93 ± 0.71 | 3.12 ± 0.33 | 0.74 ± 0.24 | 2.82 ± 0.28 |
| Muscle | 0.73 ± 0.12 | 0.22 ± 0.07 | 0.49 ± 0.15 | 0.16 ± 0.04 |
| Bone | 0.95 ± 0.30 | 0.27 ± 0.08 | 0.45 ± 0.19 | 0.20 ± 0.07 |
| Brain | 0.19 ± 0.05 | 0.05 ± 0.01 | 0.09 ± 0.04 | 0.03 ± 0.01 |

TABLE 5

Dual isotope biodistribution data 3 h after injection of $^{111}$In-tetrazine 28 (21 µg/75 µL per mouse, ca. 0.5 MBq), 27 h or 75 h after the administration of $^{125}$I-CC49-TCO-O minor (CC49-20b; 100 µg/100 µL per mouse, ca. 0.2 MBq). Data presented as % ID/gram ± SD.

|  | 1 day pretargeting (n = 3) | | 3 days pretargeting (n = 3) | |
| --- | --- | --- | --- | --- |
|  | $^{125}$I-mAb | $^{111}$In-tetrazine | $^{125}$I-mAb | $^{111}$In-tetrazine |
| Blood | 6.45 ± 1.46 | 1.61 ± 0.45 | 2.20 ± 0.41 | 0.59 ± 0.10 |
| Tumor | 18.46 ± 4.14 | 3.42 ± 0.40 | 17.56 ± 4.77 | 2.56 ± 0.65 |
| Heart | 1.80 ± 0.30 | 0.50 ± 0.04 | 0.70 ± 0.12 | 0.22 ± 0.03 |
| Lung | 3.19 ± 0.53 | 0.97 ± 0.16 | 1.38 ± 0.28 | 0.46 ± 0.07 |
| Liver | 4.79 ± 2.22 | 1.41 ± 0.45 | 2.17 ± 0.63 | 0.64 ± 0.06 |
| Spleen | 2.07 ± 0.46 | 0.65 ± 0.12 | 0.99 ± 0.33 | 0.35 ± 0.08 |
| Kidney | 1.76 ± 0.38 | 3.39 ± 0.84 | 0.69 ± 0.09 | 2.59 ± 0.24 |
| Muscle | 0.80 ± 0.20 | 0.24 ± 0.06 | 0.40 ± 0.14 | 0.18 ± 0.09 |
| Bone | 0.75 ± 0.17 | 0.40 ± 0.05 | 0.29 ± 0.05 | 0.16 ± 0.02 |
| Brain | 0.25 ± 0.06 | 0.07 ± 0.01 | 0.09 ± 0.02 | 0.03 ± 0.01 |

The biodistribution data confirm the higher stability in vivo of the CC49-TCO constructs lacking the spacer with respect to the first generation CC49-PEG$_{10}$-TCO major 23a. In mice pre-treated with CC49-PEG$_{10}$-TCO major (CC49-23a) 24 h before injection of the tetrazine, the high amount of mAb present in the tumor (15.81±0.22% ID/gram) resulted in 3.09±0.01% ID/gram $^{177}$Lu accumulation due to the reaction between the TCO and the tetrazine (Table 3). Unfortunately, the reaction of $^{177}$Lu-tetrazine with the high amount of mAb-TCO circulating in blood (5.55±1.85% ID/g) resulted also in a low tumor-to-blood ratio (T/B=3.1±1.0). The TB ratio improved significantly when the radio labeled tetrazine was administered 4 days after the mAb (21.3±4.0) because of mAb clearance. However, at this time an approximately four-fold lower $^{177}$Lu-tetrazine accumulation in tumour was also observed (0.86±0.39% ID/gram). This decrease in absolute tetrazine accumulation is not the consequence of mAb-TCO release from the tissue (10.99±4.24% ID/gram $^{125}$I-mAb still present in tumor) but was reasonably due to TCO degradation in vivo during the 4 days between injections.

On the contrary, when the mice were pre-treated with the CC49-TCO constructs lacking the PEG$_{10}$ spacer, no decrease in tumor uptake of $^{111}$In-tetrazine was observed 3 days after mAb injection with respect to 1 day after mAb injection (Tables 4-6). At the same time, the T/B ratios increased from ca 2 to over 4 due to mAb-TCO clearance from blood. The maintained reactivity of the tumor-bound TCO within this period of time signifies its higher stability with respect to the first generation CC49-PEG$_{10}$-TCO.

Example 8

Imaging Experiments

Tumor-bearing mice were injected with $^{111}$In-tetrazine 28 (21 µg/75 µL per mouse, 20-50 MBq) 3 or 4 days after receiving 100 µg of a CC49-TCO construct without PEG$_{10}$ spacer. Approximately 1 h later, the mice were anesthetized and positioned on an animal bed equipped with a nose cone for anesthesia and a sensor for respiratory monitoring. Single photon emission computed tomography (SPECT) was performed 2 h post tetrazine injection with a four-headed multi-pinhole small animal SPECT/CT imaging system (NanoSPECT, Bioscan Inc.). The SPECT acquisition (1 h total) was performed with 1.4 mm diameter pinholes and a 120-140 sec acquisition time per view (24 projections). The energy window for $^{111}$In was set at 245 keV±15% and 171 keV±20%. Two-to-four days after the first scan, the mice were euthanized by anesthesia overdose and a second SPECT/CT scan was acquired overnight. Prior to each SPECT session a CT scan (2 sec per projection, 360 projections) was performed to obtain anatomical information on radioactivity distribution. After the acquisition, the data was reconstructed iteratively with the manufacturer's software (InVivoScope 1.39, patch 1). Regions of interest (ROIs) were drawn manually in triplicate for tumor, liver, kidney and thigh muscle. A phantom filled with a known amount of $^{111}$In was used to calibrate the scanner for tissue radioactivity quantification. The image of three mice injected with CC49-TCO-O minor (CC49-20b), CC49-TCO-O major (CC49-20a) and CC49-TCO-C minor (CC49-14b) on a representative time scale are depicted in FIG. 13 A-C, respectively.

Figure 13:
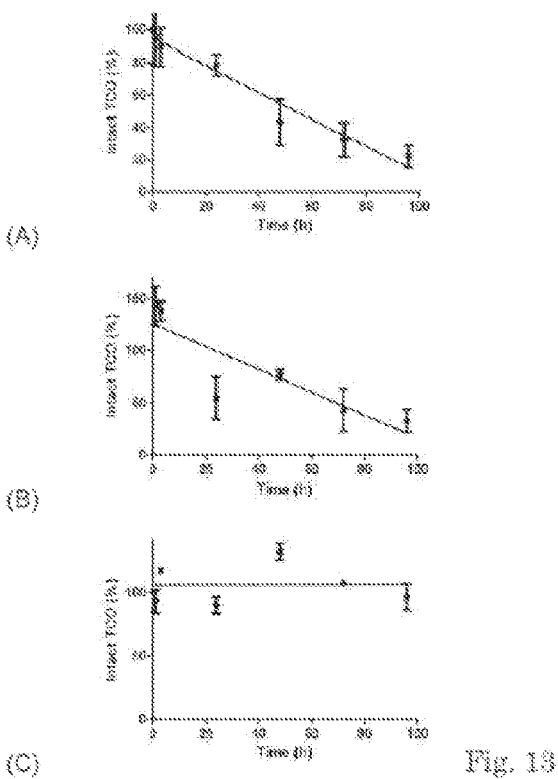
FIG. 13 depicts the in vivo stability in mice of three different cyclooctene dienophiles.
Figure 14:
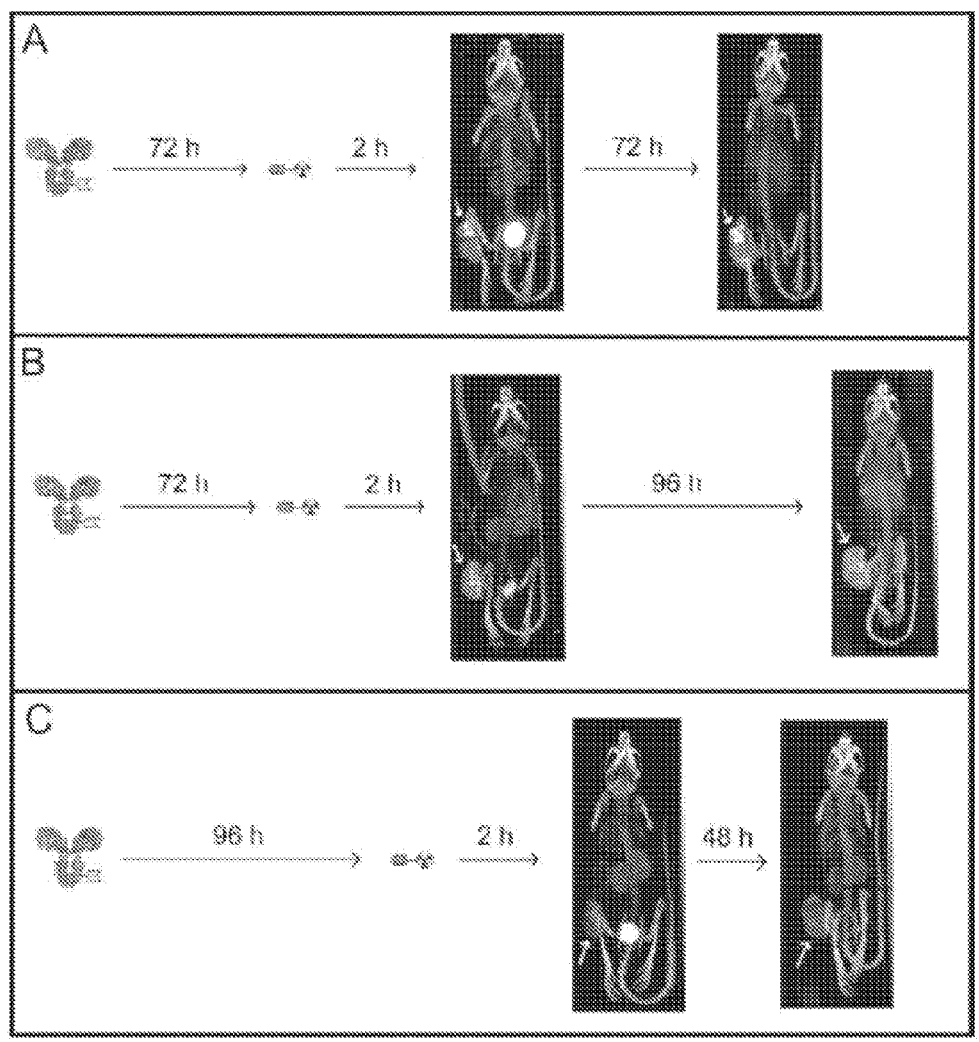
FIG. 14 shows SPECT/CT projections of live mice

FIG. 13: (left) SPECT/CT projections of live mice 2 h after injection of $^{111}$In-tetrazine 28 (21 µg/75 µL per mouse, ca. 40 MBq), 3-4 days after the administration of (A) CC49-TCO-O minor (CC49-20b), (B) CC49-TCO-O major (CC49-20a) or (C) CC49-TCO-C minor (CC49-14b) (100 µg/100 µL per mouse). (Right), post mortem SPECT/CT scans of the same mice 2-4 days after the first imaging session. White arrows indicate tumors.

The longitudinal SPECT/CT studies in mice show high $^{111}$In-tetrazine uptake in tumor 3 days after pre-treatment with CC49-TCO-O (both major and minor forms) and thereby confirm the in vivo stability of these TCO-constructs (FIGS. 13 A and B). At this time (left images), most of the non tumor-bound mAb-TCO had cleared from the circulation and therefore the only visible organs beside the tumors are the kidney and the bladder due to $^{111}$In-tetrazine urinary excretion. Importantly, no radioactivity is visible in blood and blood rich organs such as the liver. The very low background radioactivity is a fundamental improvement respect to the results obtained with the first generation CC49-PEG$_{10}$-TCO (see R. Rossin, P. Renart Verkerk, Sandra M. van den Bosch, R. C. M. Vulders, 1. Verel, J. Lub, M. S. Robillard, Angew Chem Int Ed 2010, 49, 3375) and will translate into a lower dose to bone marrow and other dose limiting organs in patients.

Noteworthy, the tumors of the mice pre-treated with CC49-TCO 0 were still highly radioactive 72-96 h after $^{111}$In-tetrazine injection, suggesting high in vivo stability of the TCO-tetrazine cycloaddition product. At the late time point, some activity is still visible in the mouse kidney and some has accumulated in liver, reasonably due to antigen shedding and to clearance of the mAb still circulating in blood at the time of tetrazine injection. The retention of radioactivity in tumors for an extended period of time is also of paramount importance when aiming at pretargeted RIT in cancer patients. In fact, the longer the therapeutic radionuclide is bound to the target tissue the higher is the dose delivered to the tumors.

Surprisingly, a rather low radioactivity uptake was observed in mice injected with $^{111}$In-tetrazine after the administration of CC49-TCO-C minor, likely due to the 4 days delay between the two treatments (FIG. 13 C). However, also in this case, the signal in the tumor was still present 2 days after the early scan confirming the in vivo stability of the cycloaddition product resulting from the in vivo Diels-Alder reaction.

Example 9

This example relates to the in silico testing of various substituents on various positions of trans cyclooctene. For various substituted cyclooctenes, the HOMO energies are calculated using MOPAC software (Cambridge stware Mopac Pro version 8.03).
The results are given in Table 6 below.

TABLE 6

Carbon atoms are numbered in accordance with the following structure:

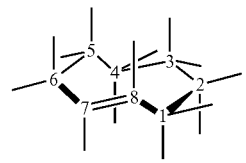

| 1/6 | 2/5 | 3/4 | 7/8 | HOMO (eV) |
|---|---|---|---|---|
| | | | | -9.23 |
| CH2—tBu (a) | | | | -9.24 |
| CH2—tBu (e) | | | | -9.19 |
| | CH2—tBu (a) | | | -9.17 |
| | CH2—tBu (e) | | | -9.20 |
| | | CH2—tBu (a) | | -9.15 |
| | | CH2—tBu (e) | | -9.20 |
| | | | CH2—tBu | -8.93 |
| OH (a) | | | | -9.28 |
| OH (e) | | | | -9.39 |
| | OH (a) | | | -9.28 |
| | OH (e) | | | -9.41 |
| | | OH (a) | | -9.23 |
| | | OH (e) | | -9.40 |
| | | | OH | -8.80 |
| O—Me (a) | | | | -9.25 |
| O—Me (e) | | | | -9.37 |
| | O—Me (a) | | | -9.13 |
| | O—Me (e) | | | -9.24 |
| | | O—Me (a) | | -9.12 |
| | | O—Me (e) | | -9.37 |
| | | | O—Me | -8.96 |
| Me (a) | | | | -9.23 |
| Me (e) | | | | -9.23 |
| | Me (a) | | | -9.22 |
| | Me (e) | | | -9.22 |
| | | Me (a) | | -9.17 |
| | | Me (e) | | -9.22 |
| | | | Me | -8.93 |
| O—tBu (a) | | | | -9.20 |
| O—tBu (e) | | | | -9.31 |
| | O—tBu (a) | | | -8.95 |
| | O—tBu (e) | | | -9.12 |
| | | O—tBu (a) | | -8.99 |

TABLE 6-continued

Carbon atoms are numbered in accordance with the following structure:

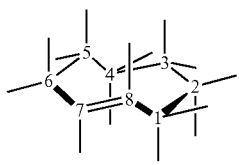

| 1/6 | 2/5 | 3/4 | 7/8 | HOMO (eV) |
|---|---|---|---|---|
| | | O—tBu (e) | | −9.30 |
| | | | O—tBu | −8.95 |
| tBu (a) | | | | −9.21 |
| tBu (e) | | | | −9.22 |
| | tBu (a) | | | −9.17 |
| | tBu (e) | | | −9.22 |
| | | tBu (a) | | −9.15 |
| | | tBu (e) | | −9.19 |
| | | | tBu | −8.88 |
| O—Phe (a) | | | | −8.94 |
| O—Phe (e) | | | | −9.05 |
| | O—Phe (a) | | | −8.88 |
| | O—Phe (e) | | | −8.96 |
| | | O—Phe (a) | | −9.01 |
| | | O—Phe (e) | | −9.23 |
| | | | O—Phe | −8.69 |
| O—Bz (a) | | | | −9.36 |
| O—Bz (e) | | | | −9.37 |
| | O—Bz (a) | | | −9.02 |
| | O—Bz (e) | | | −9.23 |
| | | O—Bz (a) | | −9.07 |
| | | O—Bz (e) | | −9.36 |
| | | | O—Bz | −8.58 |

HOMO energies as determined by Mopac for different substituents. Herein (a) denotes axial; (e) denotes equatorial.

Example 10

Figure 15:
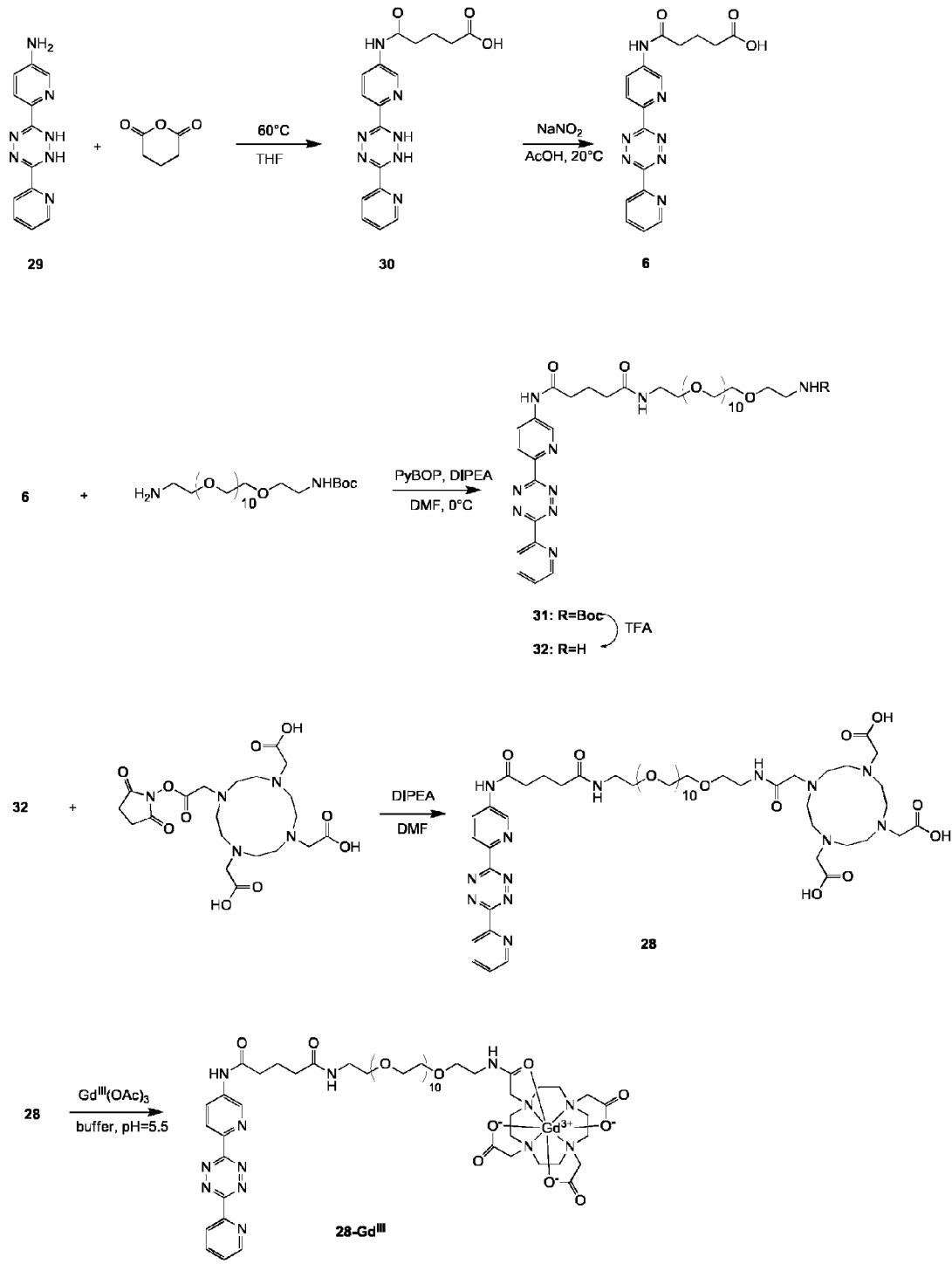
FIG. 15 depicts the alternative synthesis procedure of tetrazine probe 28, and the synthesis of the corresponding Gd-complex, 28-Gd$^{III}$

Alternative Synthesis Procedure for Tetrazine 28, and Synthesis of the Corresponding Gd-Complex, 28-Gd Reference is made to FIG. 15, depicting the synthesis route.

5-Oxo-5-(6-(6-(pyridin-2-yl)-1,4-dihydro-1,2,4,5-tetrazin-3-yl)pyridin-3-ylamino)pentanoic acid (30)

6-(6-(Pyridin-2-yl)-1,4-dihydro-1,2,4,5-tetrazin-3-yl)-pyridin-3-amine (29) was synthesized according to a literature procedure (M. L. Blackman, M. Royzen, M. J. Fox, *J. Am. Chem. Soc.* 2008, 130, 13518-13519). A mixture of 29 (428 mg, 1.69 mmol) and glutaric anhydride (231 mg, 2.03 mmol) in THF (10 mL) was heated at 60° C. for 40 h under an inert atmosphere of argon. After cooling, the orange precipitate was washed with THF (5 mL) and dried to yield 30 as an orange solid (537 mg, 87%).

$^1$H-NMR (400 MHz, DMSO-d6): δ=12.1 (br. s, 1H), 10.37 (s, 1H), 8.92 (s, 1H), 8.87 (s, 1H), 8.82 (d, J=1.8 Hz, 1H), 8.64 (d, J=4.8 Hz, 1H), 8.15 (dd, $J_1$=8.4 Hz, $J_2$=2.4 Hz, 1H), 8.0-7.9 (m, 3H), 7.53 (dt, $J_1$=1.8 Hz, $J_2$=4.8 Hz, 1H), 2.43 (t, J=7.4 Hz, 2H), 2.29 (t, J=7.4 Hz, 2H), 1.83 (q, J=7.4 Hz, 2H); $^{13}$C-NMR (100 MHz, DMSO-d6): δ=174.2, 171.6, 148.6, 147.3, 146.3, 146.1, 141.4, 138.9, 137.4, 137.2, 126.6, 125.3, 121.3, 120.9, 35.3, 32.9, 20.2; MS (ESI, m/z): Calcd for $C_{17}H_{18}N_7O_3^+$ ([M+H]$^+$): 368.15. Found: 368.25.

5-Oxo-5-(6-(6-(pyridin-2-yl)-1,2,4,5-tetrazin-3-yl)pyridin-3-ylamino)pentanoic acid (6)

Compound 30 (166 mg; 0.452 mmol) was suspended in acetic acid (3 mL) and sodium nitrite (93.5 mg; 1.36 mmol) was added. Fast coloration to a purple suspension was observed. After 15 minutes of stirring, the reaction mixture was filtered, washed with water (2×6 mL) and acetone (3 mL), and dried, to yield the product as a purple solid (152 mg, 92%).

$^1$H-NMR (300 MHz, DMSO-d6): δ=12.13 (s, 1H), 10.58 (s, 1H), 9.05 (d, J=2.3 Hz, 1H), 8.94 (d, J=4.2 Hz, 1H), 8.62 (d, J=8.8 Hz, 1H), 8.60 (d, J=8.8 Hz, 1H), 8.43 (dd, $J_1$=2.3 Hz, $J_2$=8.8 Hz, 1H), 8.16 (td, $J_1$=7.8 Hz, $J_2$=1.7 Hz, 1H), 7.73 (ddd, $J_1$=1.1 Hz, $J_2$=4.4 Hz, $J_3$=7.4 Hz), 2.50 (t, J=7.3 Hz, 2H), 2.33 (t, J=7.3 Hz, 2H), 1.86 (q, J=7.3 Hz, 2H); $^{13}$C-NMR (75 MHz, DMSO-d6): δ=174.1 (q), 172.0 (q), 163.0 (q), 162.7 (q), 150.6 (t), 150.2 (q), 143.8 (q), 141.3 (t), 138.4 (q), 137.7 (t), 126.5 (t), 126.1 (t), 124.8 (t), 124.1 (t), 35.4 (s), 32.9 (s), 20.2 (s); HRMS (ESI, m/z): Calcd for $C_{17}H_{16}N_7O_3^+$ ([M+H]$^+$): 366.1314. Found: 366.1313.

Tert-butyl (37,41-dioxo-41-((6-(6-(pyridin-2-yl)-1,2,4,5-tetrazin-3-yl)pyridin-3-yl)amino)-3,6,9,12,15,18,21,24,27,30,33-undecaoxa-36-azahentetracontyl) carbamate (31)

PyBOP (148 mg, 0.284 mmol) was added to a stirred mixture of 6 (94.4 mg, 0.258 mmol), amino-PEG$_{10}$-amino-Boc (150 mg, 0.233 mmol), and N,N-diisopropylethylamine (freshly distilled, 100 mg, 0.774 mmol) in DMF (2 mL) at 0° C. The mixture was allowed to warm to room temperature and stirring was continued for 15 min. The clear, dark red solution was evaporated to dryness and the product was redissolved in chloroform (5 mL), washed with 0.2 M KH$_2$PO$_4$ (pH=4.5, 3×3 mL) and sat. Na$_2$CO$_3$ (2×3 mL), and then precipitated in diethyl ether (20 mL). The precipitate was collected by centrifugation and purified by column chromatography on silica using a gradient of methanol in chloroform (0-10%) giving 31 as a purple waxy solid (148 mg, 64%).

$^1$H-NMR (300 MHz, CDCl$_3$): δ=9.07 (d, J=2.2 Hz, 1H), 8.97 (d, J=4.6 Hz, 1H), 8.73 (d, J=8.8 Hz, 1H), 8.72 (d, J=8.8 Hz, 1H), 8.63 (dd, $J_1$=2.3 Hz, $J_2$=8.8 Hz, 1H), 8.03 (td, $J_1$=7.8 Hz, $J_2$=1.7 Hz, 1H), 7.59 (ddd, $J_1$=1.1 Hz, $J_2$=4.6 Hz, $J_3$=7.4 Hz), 7.01 (s, 1H), 5.14 (s, 1H), 3.9-3.2 (broad s, 48H), 2.60 (t, J=7.1 Hz, 2H), 2.37 (t, J=7.1 Hz, 2H), 2.09 (q, J=7.1 Hz, 2H), 1.43 (s, 9H); $^{13}$C-NMR (75 MHz, CDCl$_3$): δ=173.8 (q), 173.1 (q), 163.8 (q), 163.7 (q), 151.3 (t), 150.5 (q), 144.0 (q), 142.7 (t), 139.2 (q), 137.9 (t), 127.0 (t), 126.9 (t), 125.5 (t), 124.7 (t), 79.5 (q), 70.5 (s), 70.1 (s), 40.7 (s), 39.7 (s), 36.5 (s), 35.5 (s), 28.8 (p), 21.9 (s); HRMS (ESI, m/z): Calcd for $C_{46}H_{74}N_9O_{15}^+$ ([M+H]$^+$): 992.5304. Found: 992.5301.

2,2',2''-(10-(2,40,44-Trioxo-44-((6-(6-(pyridine-2-yl)-1,2,4,5-tetrazin-3-yl)pyridine-3-yl)amino)-6,9,12,15,18,21,24,27,30,33,36-undecaoxa-3,39-diazatetratetracontyl)-1,4,7,10-tetraazacyclododecane-1,4,7-triyl)triacetic acid (28)

Product 31 (72.3 mg, 0.0727 mmol) was dissolved in DCM (1 mL), and TFA (1 mL) was added. The mixture was stirred for 1 h at room temperature. After evaporation, the residue was dissolved in acetonitrile (1.5 mL) and precipitated in diethyl ether (15 mL). The purple precipitate was isolated by filtration to give the TFA-salt of 32 in quantitative yield. This was dissolved in DMF (1.5 mL), and DOTA-NHS (69.6 mg, 0.075 mmol) and N,N-diisopropylethylamine (freshly distilled, 44 mg, 0.341 mmol) were added. The mixture was stirred for 30 min at room temperature. After evaporation of the clear, dark red/purple solution, the crude material was dissolved in water and purified by preparative HPLC. After lyophilisation, 28 (80.5 mg, 87% yield) was obtained.

$^1$H-NMR (600 MHz, DMSO-d6): δ=9.22 (d, J=2.4 Hz, 1H), 9.10 (dd, $J_1$=4.7 Hz, $J_2$=1.1 Hz, 1H), 8.78 (d, J=8.7 Hz, 1H), 8.75 (d, J=7.8 Hz, 1H), 8.59 (dd, $J_1$=2.4 Hz, $J_2$=8.7 Hz, 1H), 8.32 (td, $J_1$=7.8 Hz, $J_2$=1.7 Hz, 1H), 8.08 (ddd, $J_1$=1.1 Hz, $J_2$=4.7 Hz, $J_3$=7.8 Hz), 3.9-3.1 (m, 80H), 2.60 (t, J=7.3 Hz, 2H), 2.34 (t, J=7.3 Hz, 2H), 2.02 (q, J=7.3 Hz, 2H); $^{13}$C-NMR (150 MHz, DMSO-d6): δ=172.8 (q), 172.5 (q), 163.8 (q), 163.5 (q), 151.3 (t), 150.9 (q), 144.5 (q), 142.0 (t), 139.3 (q), 138.5 (t), 127.3 (t), 126.9 (t), 125.6 (t), 124.9 (t), 70.5 (s), 70.3 (s), 69.9 (s), 69.5 (s), 39.2 (s), 36.4 (s), 35.2 (s), 21.7 (s); HRMS (ESI, m/z): Calcd for $C_{57}H_{92}N_{13}O_{20}^+$ ([M+H]$^+$): 1278.6582. Found: 1278.6557.

Gd$^{III}$-Complex of 28, (28-Gd$^{III}$)

Compound 28 (204 mg, 0.160 mmol) was dissolved in aqueous ammonium acetate (0.1 M, pH=5.5, 5 mL), and gadolinium(III) acetate hydrate (96.8 mg, 0.239 mmol) was added. The mixture was stirred at room temperature for 30 min, immediately followed by purification by preparative HPLC. After lyophilisation, the Gd$^{III}$-complex was obtained as a purple solid (188 mg, 82% yield). MS (ESI, m/z): Calcd for $C_{57}H_{89}H_{13}O_{20}Gd^+$ ([M+H]$^+$): 1433.56. Found: 1433.58.

Example 11

Chemical Synthesis of New Model Tetrazine Probes

Figure 16:
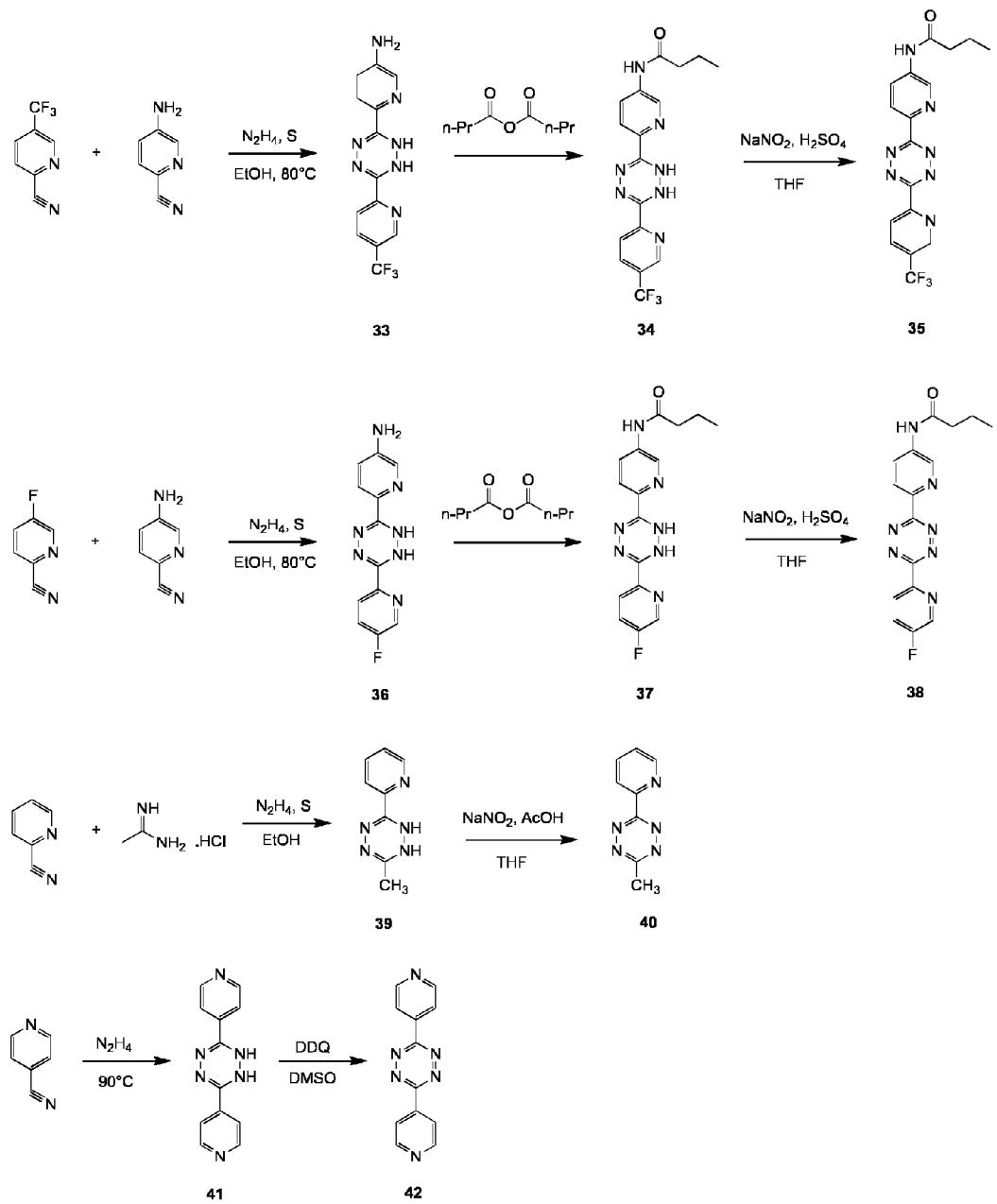
FIG. 16 shows synthesis routes for tetrazine model probes 35, 38, 40, and 42

Several tetrazine model probes comprising alternative tetrazine moieties were synthesized. Reference is made to FIG. 16, depicting the synthesis routes.

3-(5-Butyramido-2-pyridyl)-6-(5-(trifluoromethyl)-2-pyridyl)-1,2,4,5-tetrazine (35)

2-Cyano-5-trifluoromethyl-pyridine (200 mg, 1.16 mmol), 2-cyano-5-amino-pyridine (300 mg, 2.52 mmol) and sulfur (80 mg, 2.52 mmol) were stirred in ethanol (2 mL) under an inert atmosphere of argon. Hydrazine hydrate (0.60 g; 12.0 mmol) was added and the mixture was heated overnight at 80° C. The reaction mixture was allowed to cool and water (2 mL) was added. Centrifugation yielded a solid that was washed with water/ethanol=1/2 and that was dried to give 135 mg of crude product 33. Water was added to the combined supernatants of the centrifugation, resulting in precipitation of a further batch of crude material (188 mg), which was isolated by centrifugation and drying.

This crude amine product (33) and butyric anhydride (285 mg; 1.80 mmol) were stirred and heated at 65° C. in THF (5 mL) overnight. The reaction mixture was concentrated and the residue was stirred in hexane/diethyl ether=3/1. This suspension was filtered over a glass filter and the residue was purified by silica column chromatography applying hexane/acetone mixtures as eluent, yielding 90 mg of crude product 34 (ca. 60% pure).

The crude amidated dihydrotetrazine 34 (62 mg) was suspended in a mixture of THF (1.5 mL) and water (2.0 mL). While stirring, NaNO$_2$ (88 mg; 1.28 mmol) was added, and then a solution of sulfuric acid (130 mg; 1.33 mmol) in water (1 mL) was added dropwise at 0° C. Fast coloration to a red suspension was observed. After 3 minutes of stirring, the reaction mixture was diluted with chloroform and water leaving a purple precipitate which was isolated by filtration over a glass filter. The organic layer in the filtrate was concentrated and diluted with diethyl ether to induce precipitation of a second crop of purple solid. The combined solids were triturated with a mixture of chloroform and diethyl ether and isolated by filtration to give the pure tetrazine 35 (ca. 25 mg, 8% yield overall, as calculated from 2-cyano-5-trifluoromethyl-pyridine).

$^1$H NMR (CDCl$_3$/CD$_3$OD): δ=9.2 (s, 1H), 8.9 (d, 1H), 8.75 (multiple signals, 3H), 8.3 (d, 1H), 2.45 (t, 2H), 1.8 (m, 2H), 1.05 (t, 3H) ppm. $^{19}$F NMR (CDCl$_3$/CD$_3$OD): δ=−62.9 ppm. LC-MS/PDA: one peak in chromatogram, m/z=390.2 (M+H$^+$) and 800.8 (2M+Na$^+$), $λ_{max}$=329 and 526 nm.

3-(5-Fluoro-2-pyridyl)-6-(5-butanamido-2-pyridyl)-1,2,4,5-tetrazine (38)

2-Cyano-5-fluoro-pyridine (100 mg, 0.82 mmol), 2-cyano-5-amino-pyridine (200 mg, 1.68 mmol) and sulfur (55 mg, 1.72 mmol) were stirred in ethanol (1.5 mL) under an inert atmosphere of argon. Hydrazine hydrate (0.35 g; 7.0 mmol) was added and the mixture was heated overnight at 90° C. The reaction mixture was allowed to cool down and ethanol (5 mL) was added. Filtration over a glass filter yielded a solid that was washed with hexane and then dried to give 90 mg of crude product 36.

Subsequently, this crude amine product 36 and butyric anhydride (93 mg; 0.59 mmol) were stirred and heated at 65° C. in THF (1.5 mL). After overnight reaction under argon, the reaction mixture was cooled down, diluted with some hexane (ca. 3 mL) and filtered over a glass filter. The residue was purified by silica column chromatography applying hexane/acetone mixtures as eluent, yielding pure amidated product 37 (ca. 28 mg, 10% yield overall, as calculated from 2-cyano-5-fluoro-pyridine).

$^1$H NMR (CDCl$_3$/CD$_3$OD): δ=9.25 (bs, 1H, NH), 8.7 (s, 1H), 8.5 (s, 1H, NH), 8.4 (multiple signals, 2H), 8.2 (m, 1H), 8.1 (m, 1H), 7.95 (m, 1H), 7.5 (m, 1H), 2.4 (t, 2H), 1.75 (m, 2H), 1.05 (t, 3H) ppm. $^{13}$C NMR (CDCl$_3$/CD$_3$OD): δ=172.8, 161.6, 159.0, 146.6, 146.1, 143.5 (d), 141.6, 139.3, 136.8, 136.6, 136.4, 127.0, 124.0, 123.8, 122.6, 121.5, 38.9, 18.8, 13.5 ppm (due to C—F coupling, signals of some carbons are doublets). LC-MS/PDA: one peak in chromatogram, m/z=342.1 (M+H$^+$), $λ_{max}$=288 nm.

The amidated dihydrotetrazine 37 (28 mg; 0.082 mmol) was suspended in a mixture of THF (2 mL) and water (2 mL). While stirring, NaNO$_2$ (85 mg; 1.23 mmol), and a solution of sulfuric acid (120 mg; 1.23 mmol) in water (2 mL) was added dropwise at 0° C. Fast coloration to a purple suspension was observed. After 3 minutes of stirring, chloroform and water were added. The purple chloroform layer was washed twice with water and then concentrated. The solid residue was stirred in a little chloroform to which then hexane was added. The almost colorless supernatant was decanted, and the solid was dried to yield 21 mg of purple powder 38 (yield: 75%).

$^1$H NMR (CDCl$_3$/CD$_3$OD): δ=8.8 (multiple signals, 5H), 7.75 (m, 1H), 2.45 (t, 2H), 1.8 (m, 2H), 1.05 (t, 3H) ppm. $^{13}$C NMR (CDCl$_3$/CD$_3$OD): δ=173.4, 162.9, 162.6, 162.4, 159.8, 146.0, 143.2, 141.3, 139.7 and 139.4, 138.8, 126.9, 125.8 (d), 125.2, 124.4, 124.2, 39.0, 18.7, 13.5 ppm (due to C—F coupling, signals of some carbons are doublets). $^{19}$F NMR (CDCl$_3$/CD$_3$OD): δ=−120.4 ppm. LC-MS/PDA: one peak in chromatogram, m/z=340.2 (M+H$^+$), $λ_{max}$=324 and 529 nm.

3-(2-Pyridyl)-6-methyl-1,2,4,5-tetrazine (40)

2-Cyanopyridine (500 mg, 4.8 mmol), acetamidine hydroxhloride (2.00 g, 21.2 mmol) and sulfur (155 mg, 4.8 mmol) were stirred in ethanol (5 mL) under an inert atmosphere of argon. Hydrazine hydrate (2.76 g; 55.2 mmol) was added and the mixture was stirred overnight at 20° C. The turbid mixture was filtered and the filtrate was evaporated to dryness, to yield 2.9 g of the orange colored crude product 39.

Subsequently, this crude product (800 mg) was suspended in a mixture of THF (3 mL) and acetic acid (4 mL). A solution of $NaNO_2$ (2.0 g; 29.0 mmol) in water (3 mL) was added at 0° C. Instantaneous coloration to a red/purple suspension was observed. After 5 minutes of stirring at 0° C., chloroform and water were added. The purple chloroform layer was washed twice with water and then concentrated. The solid residue was stirred in a 1:1 mixture of chloroform and hexane, and then filtered. The filtrate was concentrated and the crude product was purified by silica column chromatography applying chloroform/acetone mixtures as eluent, yielding pure product 40 (48 mg, 21% yield overall, as calculated from 2-cyanopyridine).

$^1$H NMR ($CDCl_3$): δ=8.96 (d, 2H), 8.65 (d, 2H), 7.99 (t, 2H), 7.56 (dd, 3H), 3.17 (s, 3H) ppm. $^{13}$C NMR ($CDCl_3$): δ=168.1. 163.6, 150.9, 150.3, 137.4, 126.3, 123.9, 21.4 ppm. LC-MS/PDA: one peak in chromatogram, m/z=174.3 (M+H$^+$), $\lambda_{max}$=274 and 524 nm.

3,6-Bis(4-pyridyl)-1,2,4,5-tetrazine (42)

4-Cyanopyridine (858 mg; 8.24 mmol) and hydrazine monohydrate (1.24 g; 24.7 mmol) were heated at 90° C. for 16 hr under an inert atmosphere of argon. The mixture was allowed to cool to room temperature and then diluted with water (3 mL). The orange precipitate (41) was filtered and washed with water (3 mL), and subsequently dissolved in DMSO (10 mL). DDQ (372 mg; 1.64 mmol) was added to this solution. Instantaneous coloration to a dark red solution was observed. After 60 minutes, saturated sodium hydrogencarbonate (20 mL) was added and the product was extracted with chloroform (three times 30 mL). The combined organic layers were dried over $Na_2SO_4$ and evaporated to dryness to yield the title compound as a pink solid (52 mg; 5% overall yield, as calculated from 4-cyanopyridine).

$^1$H-NMR ($CDCl_3$): δ 8.97 (d, 4H), 8.52 (d, 4H) ppm. LC-MS/PDA: one peak in chromatogram, m/z=237.2 (M+H$^+$), $\lambda_{max}$=271 and 523 nm.

Example 12

Chemical Synthesis of Additional Trans-Cyclooctene Constructs

Figure 17:
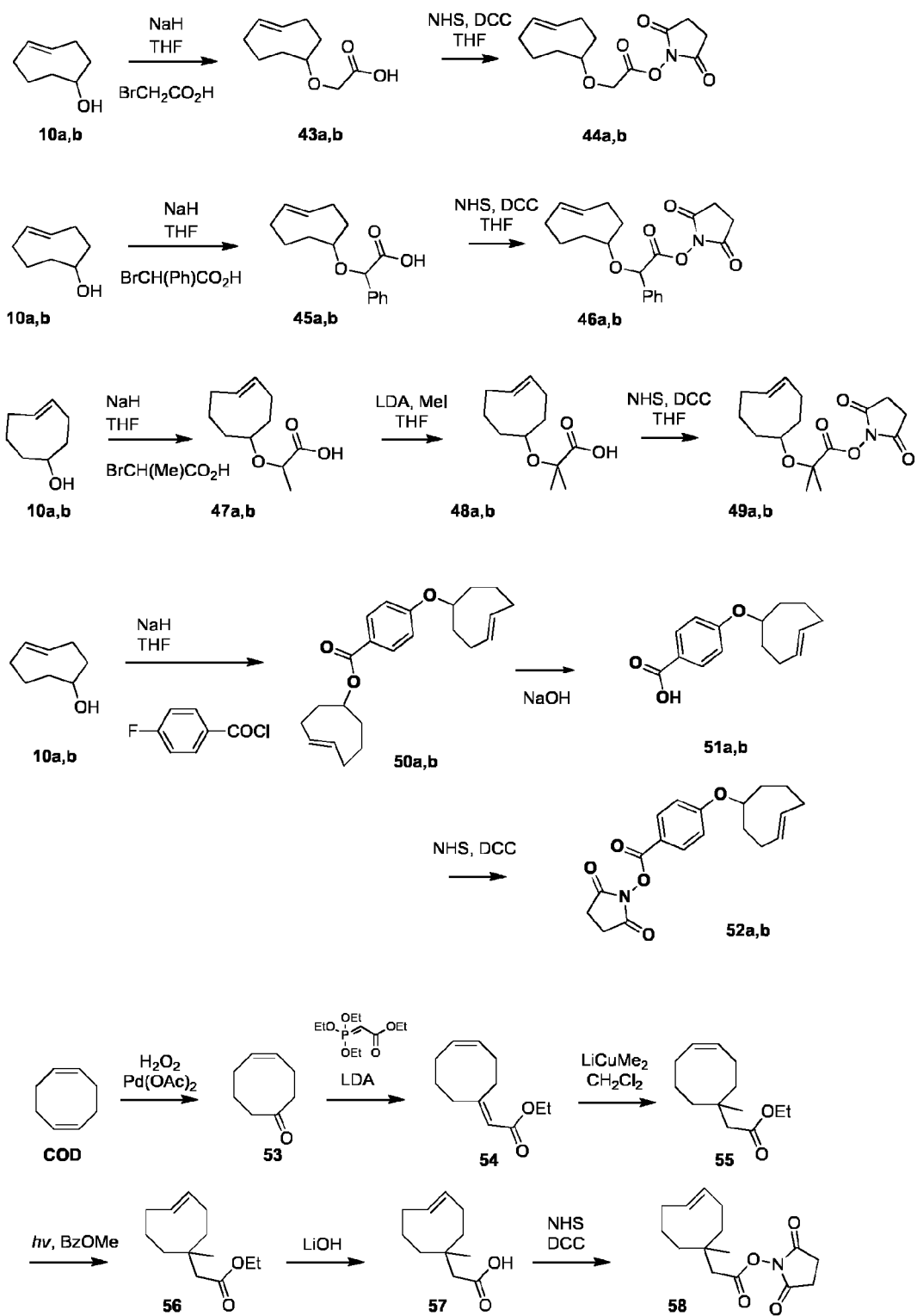
FIG. 17 shows synthesis routes of novel TCOs

Reference is made to FIG. 17 detailing the synthesis routes.

(E-Major)-2,5-dioxopyrrolidin-1-yl 2-(cyclooct-4-en-1-yloxy)acetate (44a)

To an ice-cooled solution of 10a (1.73 g, 13.73 mmol, containing ca. 10% of the cis isomer) in THF (40 mL) was added sodium hydride in oil (60%, 2.60 g, 65.0 mmol). The mixture was stirred for 15 min at RT, then heated to 50° C. for 1 h. The mixture was cooled in ice, and bromoacetic acid (2.50 g, 17.9 mmol) was added. The suspension was stirred for 1 h in ice, then at ca. 25° C. for 64 h, more THF being added in order to maintain a stirrable suspension (total volume ca. 100 mL). After heating at 50° C. for 1 h, the mixture was cooled and water was slowly added. Most of the THF was removed by rotary evaporation and more water was added (total volume 50 mL). The aqueous mixture was extracted with MTBE (2×75 mL), and the organic layers were washed with 25 mL water. The combined aqueous layers were acidified with 16 g citric acid, and the product was extracted with 2×75 mL MTBE. Drying and rotary evaporation left a residue which was purified by column chromatography (40 g $SiO_2$). The product fractions were combined and the residue was recrystallized from heptane containing a trace of MTBE. This afforded 810 mg of product 43a (810 mg, 4.40 mmol, 32%, containing a small amount of the cis isomer). $^1$H-NMR ($CDCl_3$): δ 1.4-2.45 (m, 10H), 3.1-3.2 (m, 1H), 3.9-4.1 (AB, 2H), 5.3-5.65 (m, 2H).

Product 43a was dissolved in 30 mL dichloromethane. N-hydroxysuccinimide (715 mg, 6.22 mmol) was added and the mixture was cooled in ice. DCC (1.42 g, 6.89 mmol) was added and the mixture was stirred in ice for 30 min, then at RT for 4 h. Filtration, rotary evaporation and chromatography on 40 g silicagel using a heptane/EtOAc gradient afforded 44a. The product fractions were combined and recrystallized from heptane containing a small amount of MTBE. The product crystallized after scratching. After filtration there was obtained 180 mg of the product (0.64 mmol, 15%, containing ca. 20% of the cis isomer).

$^1$H-NMR ($CDCl_3$): δ 1.4-2.45 (m, 10H), 2.8 (s, 4H), 3.1-3.2 (m, 1H), 4.3 (s, 2H), 5.3-5.65 (m, 2H).

(E-Minor)-2,5-dioxopyrrolidin-1-yl 2-(cyclooct-4-en-1-yloxy)acetate (44b)

To an ice-cooled solution of 10b (0.78 g, 6.19 mmol) in THF (30 mL) was added sodium hydride in oil (60%, 0.94 g, 23.5 mmol). The mixture was stirred for 15 min at RT, then heated to 50° C. for 1 h. The mixture was cooled in ice, and bromoacetic acid (1.41 g, 10.14 mmol) was added. The suspension was stirred at ca. 25° C. for 20 h (a sample indicated that no coupling had taken place), then for 6 h at 55° C., 3 days at 25° C., and another 6 h at 55° C. Most of the THF was removed by rotary evaporation and 50 mL MTBE, followed by ice and 25 mL water. The layers were separated and the aqueous layer was extracted with 30 mL MTBE. The successive organic layers were washed with 25 mL water. The combined aqueous layers were cooled in ice, 50 mL MTBE was added, followed by 5.1 g citric acid. The layers were separated and the aqueous layer was extracted with 50 mL MTBE. Drying and rotary evaporation left a residue (43b) which was used as such in the next step. $^1$H-NMR ($CDCl_3$): δ 1.2-2.45 (m, 10H), 3.65-3.75 (m, 1H), 4.1 (s, 2H), 5.45-5.65 (m, 2H).

Product 43b was dissolved in 30 mL dichloromethane. N-hydroxysuccinimide (1.60 g, 13.91 mmol) was added and the mixture was cooled in ice. DCC (3.11 g, 15.10 mmol) was added and the mixture was stirred in ice for 30 min, then at RT for 3 h. Filtration, rotary evaporation and chromatography on 40 g silicagel using a toluene and then dichloromethane as the eluents afforded 44b, mixed with the NHS ester of bromoacetic acid. The mixture was dissolved in 25 mL MTBE, and 25 mL heptane was added to the solution. After stirring for 2 h, the mixture was filtered (the solid being the NHS ester of bromoacetic acid). The filtrate was rotary evaporated, the residue was dissolved in warm MTBE, some heptane was added, and the solution was cooled to RT. This precipitated the product. Filtration afforded 30 mg of product 44b (0.11 mmol, 2%).

¹H-NMR (CDCl₃): δ 1.1-2.45 (m, 10H), 2.85 (s, 4H), 3.65-3.75 (m, 1H), 4.4 (s, 2H), 5.4-5.7 (m, 2H).

(E-Major)-2,5-dioxopyrrolidin-1-yl 2-(cyclooct-4-en-1-yloxy)-2-phenyl acetate (46a)

To a solution of 10a (3.0 g, 23.8 mmol, containing <10% of the cis isomer) in THF (40 mL) was added 60% NaH in oil (3.0 g, 75.0 mmol). The mixture was stirred for 10 min at RT, then heated to 50° C. for 1.5 h. After cooling in ice, DL-2-bromophenylacetic acid (3.87 g, 18.0 mmol) was added in portions. THF (20 mL) was added to the thick paste and the suspension was stirred at 25° C. for 18 h. Most of the THF was removed by rotary evaporation at 55° C. and 50 mL MTBE was added. The mixture was cooled in cold water and some ice was added, followed by 50 mL water. The layers were separated and the aqueous layer was extracted with 50 mL MTBE. The successive organic layers were washed with 25 mL water. The combined aqueous layers were cooled in ice, 50 mL MTBE was added, followed by 10 g citric acid. The layers were separated and the aqueous layer was extracted with 50 mL MTBE. Drying and rotary evaporation left 5.05 g of product 45a which was used as such in the next step.
¹H-NMR (CDCl₃): δ 1.2-2.45 (m, 10H), 3.05-3.15 (m, 1H), 4.8 (2s, 1H), 5.15-5.3 (m, 1H), 5.45-5.65 (m, 1H), 7.3-7.5 (m, 5H).
Product 45a was dissolved in 50 mL dichloromethane. N-Hydroxysuccinimide (2.51 g, 21.8 mmol) was added and the mixture was cooled in ice. DCC (5.03 g, 24.4 mmol) was added and the mixture was stirred in ice for 15 min, then at RT for 3 h. Filtration, rotary evaporation and chromatography on 55 g silicagel using a toluene/dichloromethane gradient afforded 2.8 g of 46a (7.83 mmol, 33% based on 10a, containing ca. 5% of the cis isomer).
¹H-NMR (CDCl₃): δ 1.4-2.45 (m, 10H), 2.7 (s, 4H), 3.25-3.35 (m, 1H), 3.35-3.45 (m, 1H), 5.2 (s, 2H), 5.35-5.65 (m, 2H), 7.35-7.55 (m, 5H).

(E-Minor)-2,5-dioxopyrrolidin-1-yl 2-(cyclooct-4-en-1-yloxy)-2-phenylacetate (46b)

To a solution of 10b (1.0 g, 7.9 mmol) in THF (60 mL) at 0° C. was added 60% NaH in oil (1.26 g, 31.5 mmol) and the mixture was heated to 50° C. for 1.5 h. After cooling to 0° C. DL-2-bromophenylacetic acid (2.22 g, 10.3 mmol) was added as a solution in THF (5 mL) and the viscous suspension was stirred vigorously at RT for 16 h. After heating to 40° C. for another 24 h the mixture was poured into a solution of citric acid (9.2 g) in water (100 mL). The aqueous mixture was extracted with MTBE (3×50 mL), dried with Na₂SO₄ and the solvent was evaporated to obtain a yellow oil. The purification by column chromatography (SiO₂, CH₂Cl₂/MeOH 2%) afforded a mixture of the product, unreacted TCO and a by-product. Further purification was achieved by dissolution in MTBE and water, which was basified with 33% NaOH solution. The aqueous layer was washed with MTBE, acidified with citric acid and then extracted with MTBE (3×). The combined organic layers were dried with Na₂SO₄ and after evaporation of the solvent compound 45b (463 mg, 1.8 mmol, 23% yield) was obtained as a yellow oil. ¹H-NMR (CDCl₃): δ 1.2-2.45 (m, 10H), 3.7-3.8 (m, 1H), 4.9 and 4.95 (2s, 1H), 5.4-5.7 (m, 2H), 7.3-7.55 (m, 5H).
To a solution of 45b (463 mg, 1.8 mmol) and N-hydroxysuccinimide (250 mg, 2.2 mmol) in THF (9 mL) at 0° C. was added a solution of DCC (372 mg, 1.8 mmol) in THF (2 mL). The reaction mixture was stirred at RT for 16 h after which the precipitate was removed by filtration. The filtrate was concentrated in vacuo and purified by column chromatography (SiO₂, heptane/EtOAc gradient 25%-40%) to afford 46b (451 mg, 1.3 mmol, 71% yield) as a colourless syrup. ¹H-NMR (CDCl₃): δ 1.1-2.6 (m, 10H), 2.8 (s, 4H), 3.8-3.9 (m, 1H), 5.2 and 5.3 (2s, 2H), 5.4-5.75 (m, 2H), 7.3-7.6 (m, 5H).

(E-Major)-2,5-dioxopyrrolidin-1-yl 2-(cyclooct-4-en-1-yloxy)-2-methylpropanoate (49a)

To a solution of 10a (3.0 g, 23.8 mmol) in THF (120 mL), cooled in an ice-bath, was added 60% sodium hydride in oil (3.8 g, 95 mmol). The ice-bath was removed and the mixture was stirred at RT for 30 min and then at 50° C. for 1 h. After cooling in ice, DL-2-bromopropionic acid (3.3 mL, 35.6 mmol) was added slowly. The mixture became very viscous during the addition and it was diluted with THF (50 mL). After the addition was completed the ice-bath was removed and the reaction mixture was stirred at RT for 16 h. The progression of the reaction was followed by NMR which showed 40% conversion after 16 h. The mixture was then stirred for another 24 h at 35° C. to achieve 84% conversion. The reaction mixture was concentrated in vacuo, diluted with MTBE and then quenched with water (200 mL). The layers were separated and the aqueous layer was acidified with a solution of citric acid (22.5 g) in water (60 mL). The aqueous layer was extracted with MTBE (3×200 mL). The combined organic layers were dried over Na₂SO₄ and the solvent was evaporated to afford a mixture (5.19 g) containing 47a. The material was used in the next step without further purification.
¹H-NMR (CDCl₃): δ 1.1-2.45 (m), 1.4 (d) (13H), 3.1-3.2 (m, 1H), 3.9-4.0 (q, 1H), 5.3-5.65 (m, 2H).
To a solution of diisopropylamine (13 mL, 92 mmol) in THF (200 mL) at −70° C. was slowly added 2.5M n-butyllithium in hexanes (32 mL, 80 mmol). The mixture was then warmed slowly to −20° C. and cooled again to −70° C. Compound 47a (5.19 g) was added as a solution in THF and the mixture was warmed to −20° C. At this temperature iodomethane (10.7 mL, 172 mmol) was added and the mixture was allowed to warm to 5° C. A sample was taken and according to NMR analysis the reaction was complete. The reaction mixture was poured into a solution of citric acid (40 g) in water (200 mL) and extracted with MTBE (3×150 mL). The combined organic layers were washed with aqueous citric acid and with brine. After drying with Na₂SO₄ and evaporation of the solvent a yellow oil (9.4 g) was obtained. The purification by column chromatography (SiO₂, CH₂Cl₂/MeOH gradient 1%-4%) afforded pure 48a (1.15 g, 5.4 mmol, 23% yield over 2 steps) as a yellow syrup. ¹H-NMR (CDCl₃): δ 1.1-2.45 (m) and 1.4 (2s) (16H), 3.2-3.3 (m, 1H), 5.3-5.7 (m, 2H).
To a solution of 48a (1.15 g, 5.4 mmol) and N-hydroxysuccinimide (622 mg, 5.4 mmol) in THF (27 mL) at 0° C. was added a solution of DCC (1.12 g, 5.4 mmol) in THF (5 mL). After the addition the mixture was warmed to RT and stirred at that temperature for 16 h. The mixture was diluted with MTBE and the precipitate was filtered off. After evaporation of the solvent the residue was purified by column chromatography (SiO₂, heptane/EtOAc gradient 20%-40%). The crystallization from heptane/EtOAc afforded 49a (707 mg, 2.3 mmol, 42% yield) as colorless crystals. ¹H-NMR (CDCl₃): δ 1.5-2.4 (m), 1.55 (s), 1.60 (s) (16H), 2.85 (s, 4H), 3.2-3.3 (m, 1H), 5.4-5.65 (m, 2H).

(E-Minor)-2,5-dioxopyrrolidin-1-yl 2-(cyclooct-4-en-1-yloxy)-2-methylpropanoate (49b)

To a solution of 10b (1.5 g, 11.9 mmol) in THF (60 mL), cooled in an ice-bath, was added 60% sodium hydride in oil (1.9 g, 48 mmol). The ice-bath was removed and the mixture was stirred at 50° C. for 1.5 h. After cooling in ice, DL-2-bromopropionic acid (1.7 mL, 17.8 mmol) was added slowly. The mixture became very viscous during addition and was diluted with THF (35 mL). After the addition was completed the ice-bath was removed and the reaction mixture was stirred at RT for 16 h. The mixture was then heated to 43° C. for another 24 h. The reaction mixture was concentrated in vacuo, diluted with MTBE and then quenched with water (200 mL). The layers were separated and the aqueous layer was acidified with a solution of citric acid in water. The aqueous layer was extracted with MTBE (3×100 mL). The combined organic layers were dried with Na₂SO₄ and the solvent was evaporated to afford a mixture (2.26 g) containing 47b. The material was used in the next step without further purification.
¹H-NMR (CDCl₃): δ 1.2-2.5 (m) and 1.5 (2d) (13H), 3.65-3.75 (m, 1H), 3.95-4.15 (2q, 1H), 5.4-5.65 (m, 2H).
To a solution of diisopropylamine (5.6 mL, 39.6 mmol) in THF (100 mL) at –70° C. was slowly added 2.5M n-butyllithium in hexanes (13.5 mL, 33.8 mmol). The mixture was then warmed slowly to 0° C. and cooled again to –70° C. Compound 47b (2.26 g) was added as a solution in THF and the mixture was warmed to –20° C. At this temperature iodomethane (4.6 mL, 73.9 mmol) was added and the mixture was allowed to warm to 15° C. A sample was taken and according to NMR analysis the reaction was complete. The reaction mixture was poured into a solution of citric acid (20 g) in water (140 mL) and extracted with MTBE (3×100 mL). The combined organic layers were washed with aqueous citric acid and with brine. After drying over Na₂SO₄ and evaporation of the solvent a yellow syrup (4.6 g) was obtained. Repeated purification by column chromatography (SiO₂, CH₂Cl₂/MeOH gradient 1%-4%) afforded pure 48b (181 mg, 0.85 mmol, 7% yield over 2 steps) as a white crystalline solid. ¹H-NMR (CDCl₃): δ 1.1-2.45 (m) and 1.45 (2s) (16H), 3.9-4.0 (m, 1H), 5.45-5.65 (m, 2H).
To a solution of 48b (181 mg, 0.85 mmol) and N-hydroxysuccinimide (98 mg, 0.85 mmol) in THF (5 mL) at 0° C. was added a solution of DCC (175 mg, 0.85 mmol) in THF. After the addition, the mixture was warmed to RT and stirred at that temperature for 5 h. The mixture was diluted with MTBE and the precipitate filtered off. After evaporation of the solvent the residue was purified by column chromatography (SiO₂, heptane/EtOAc gradient 25%) to afford 49b (257 mg, 0.83 mmol, 98% yield) as a white solid. ¹H-NMR (CDCl₃): δ 0.8-2.6 (m), 1.55 (s), 1.60 (s) (16H), 2.85 (s, 4H), 3.8-3.9 (m, 1H), 5.4-5.7 (m, 2H).

(E-Major)-2,5-dioxopyrrolidin-1-yl 4-(cyclooct-4-en-1-yloxy)benzoate (52a)

To an ice-cooled solution of 10a (3.45 g, 27.38 mmol) in THF (50 mL) there was added sodium hydride in oil (60%, 2.5 g, 62.5 mmol). The mixture was stirred for 15 min in ice, then heated to 50° C. for 1 h. The mixture was cooled in ice, and 4-fluorobenzoyl chloride (1.72 g, 10.84 mmol), dissolved in 5 mL THF, was added over a 5 min period. The mixture was stirred for 2 days at 25° C. (NMR of a sample indicated the presence of much product, but also the TCO-ester of 4-fluorobenzoic acid), then for 3 h at 50° C. The mixture was cooled with water, and 10 mL water was slowly added, followed by 2 g sodium hydroxide and 5 mL water. Most of the solvents were removed by rotary evaporation, THF and 2 g sodium hydroxide were added and the mixture was warmed for 4 h at 50° C. Most of the solvents were removed by rotary evaporation and methanol was added to the residual paste. The mixture was warmed for 2 h at 50° C., followed by rotary evaporation at 55° C. The remaining suspension was diluted with 50 mL water. MTBE (100 mL) was added, the layers were separated and the organic layer was washed with 25 mL water. The organic layer contains a.o. trans cyclooctenol. The combined ice-cooled aqueous layers were treated with 20 g citric acid and the product was extracted with 2×75 mL MTBE. Drying and rotary evaporation left a solid residue, consisting of a mixture of the product and 4-fluorobenzoic acid. The solid was warmed with 40 mL methanol. Water (15-20 mL) was slowly added to the warm solution until it became cloudy. Filtration and cooling of the filtrate precipitated the product. Filtration, washing with 1/1 methanol/water, and drying under vacuum afforded 0.827 g of the desired product 51a (3.36 mmol, 30% based on 4-fluorobenzoyl chloride). ¹H-NMR (CDCl₃): δ 1.5-2.5 (m, 10H), 4.0-4.1 (m, 1H), 5.45-5.75 (m, 2H), 6.8 (d, 2H), 8.05 (d, 2H).
An ice-cooled mixture of the major trans acid 51a (1.14 g, 4.63 mmol) and N-hydroxysuccinimide (725 mg, 6.30 mmol) in 50 mL dichloromethane was treated with DCC (1.46 g, 7.08 mmol). The mixture was stirred in ice for 1 h, then at RT for 3 h. Filtration, rotary evaporation and chromatography on 40 g silicagel using a heptane/EtOAc gradient afforded a fraction of 52a, contaminated with cis isomer. The next product fractions were combined, and warmed to 60° C. with a mixture of heptane and ethyl acetate. The suspension was allowed to cool to RT, then filtered. This gave 0.973 g of the product 52a (2.83 mmol, 61%). ¹H-NMR (CDCl₃): δ 1.6-2.5 (m, 10H), 2.85 (s, 4H), 4.0-4.1 (m, 1H), 5.45-5.75 (m, 2H), 6.8 (d, 2H), 8.05 (d, 2H).

(E-Minor)-2,5-dioxopyrrolidin-1-yl 4-(cyclooct-4-en-1-yloxy)benzoate (52b)

To an ice-cooled solution of 10b (2.82 g, 22.38 mmol) in THF (40 mL) there was added sodium hydride in oil (60%, 2.0 g, 50 mmol). The mixture was stirred for 15 min in ice, 30 min at RT, then heated to 50° C. for 1 h. The mixture was cooled in ice, and 4-fluorobenzoyl chloride (1.72 g, 10.84 mmol), dissolved in 8 mL THF, was added over a 15 min period. The mixture was stirred for 18 h at RT (NMR of a sample indicated the presence of much trans-cyclooctenol), then for 6 h at 50° C., 3 days at 25° C., and another 1 h at 50° C. A solution of 2.0 g sodium hydroxide in 5 mL water was added slowly, followed by 5 mL water. Most of the THF was removed by rotary evaporation and 40 mL methanol was added to the resulting paste. The mixture was warmed for 3 h at 50° C., 20 mL THF was added and heating was continued for 4 h. The mixture was stirred overnight at 25° C. (NMR indicated the presence of still a small amount of ester), then heated for 4 h at 50° C., followed by rotary evaporation. The remaining suspension was diluted with 50 mL water. MTBE (100 mL) was added, the layers were separated and the organic layer was washed with 25 mL water. The organic layer contains a.o. trans cyclooctenol. The combined ice-cooled aqueous layers were treated with 15 g citric acid and the product was extracted with 2×75 mL MTBE. Drying and rotary evaporation left a solid residue, consisting of a mixture of the product and 4-fluorobenzoic acid. The solid was warmed with 40 mL methanol. Water (25 mL) was slowly added to the warm solution, which was subsequently allowed to cool to RT and then stirred overnight. Filtration, washing with 1/1 methanol/water, and drying under vacuum afforded 0.76 g of the desired product 51b (3.09 mmol, 28% based on 4-fluorobenzoyl chloride). $^1$H-NMR (CDCl$_3$): δ 1.3-2.6 (m, 10H), 4.55-4.65 (m, 1H), 5.55-5.85 (m, 2H), 6.9 (d, 2H), 8.05 (d, 2H).

An ice-cooled mixture of the minor trans acid 51b (0.66 g, 2.68 mmol) and N-hydroxysuccinimide (460 mg, 4.0 mmol) in 50 mL dichloromethane was treated with DCC (0.95 g, 4.61 mmol). The mixture was stirred in ice for 1 h, then at RT for 16 h. Filtration, rotary evaporation and chromatography on 30 g silicagel using dichloromethane as the eluent. The product was dissolved in 5 mL ethyl acetate. Heptane was added and the solution was partially rotary evaporated at 60° C. until a precipitate appeared. Heptane was added and the mixture was stirred for 5 min at 60° C., then allowed to cool to RT. Filtration gave 0.437 g of the product 52b (1.27 mmol, 47%).

$^1$H-NMR (CDCl$_3$): δ 1.4-2.6 (m, 10H), 2.9 (s, 4H), 4.55-4.65 (m, 1H), 5.55-5.8 (m, 2H), 6.9 (d, 2H), 8.05 (d, 2H).

(E-Major,minor)-2,5-Dioxopyrrolidin-1-yl 2-(1-methylcyclooct-4-en-1-yl)acetate (58)

A solution of 35% hydrogen peroxide (25 mL, 300 mmol) was added to a mixture of palladium acetate (45% Engelhard, 1.0 g, 2 mmol), benzoquinone (432 mg, 4 mmol) and 1,5-cyclooctadiene (27 mL, 200 mmol). The mixture was stirred for 5 days at 30° C. until NMR analysis showed 95% conversion of the starting material. The mixture was poured into Et$_2$O (1 L) and water was added (1 L). The mixture was slowly basified with 33% NaOH solution while cooling with ice. The layers were separated and the aqueous layer was extracted with Et$_2$O (2×). The combined organic layers were twice washed with 1N NaOH and dried over Na$_2$SO$_4$. A careful evaporation of the solvent afforded crude 53 (16.1 g, 130 mmol, 65% yield) as a yellow oil.

A 1.6M solution of n-butyllithium in hexanes (45 mL, 72 mmol) was added to a solution of diisopropylamine (14 mL, 100 mmol) in THF (250 mL), cooled to −80° C. The mixture was gradually warmed to 0° C. and then cooled to −80° C. A solution of triethylphosphonoacetate (15 mL, 75 mmol) in THF (100 mL) was added and the mixture was stirred for 45 min. at −70° C. Then a solution of 53 (6.21 g, 50 mmol) in THF (50 mL) was added and the mixture was slowly warmed to RT. After 16 h the mixture was further heated to reflux for 8 h until NMR analysis showed a complete conversion. The mixture was poured into water (250 mL) and extracted with MTBE (3×). The combined organic layers were washed with brine and dried over Na$_2$SO$_4$. After rotary evaporation of the solvent and purification by column chromatography (SiO$_2$, heptane/EtOAc 5%) 54 was obtained as a colorless oil (4.74 g, 24 mmol, 49% yield).

A 1.6M solution of methyllithium (59 mL, 94 mmol) was added to a suspension of copper(I)iodide (9.53 g, 50 mmol) in Et$_2$O (21 mL) cooled in an ice-bath. The grey solution was concentrated in vacuo at 0° C. and stripped twice with CH$_2$Cl$_2$. The residue was suspended in cold CH$_2$Cl$_2$ (100 mL) and cooled to −80° C. before TMSCl (4.0 mL, 46.5 mmol) was added slowly. Then a solution of 54 (4.74 g, 24 mmol) in CH$_2$Cl$_2$ (60 mL) was added drop-wise and the mixture was allowed to warm to RT over 2 h. The mixture was stirred for an additional 16 h at RT before being quenched into saturated aqueous NH$_4$Cl (150 mL). The mixture was stirred at RT and ammonia (50 mL) was added. The mixture was filtered, the filtrate being extracted with CH$_2$Cl$_2$ (3×75 mL). The combined organic layers were washed with water and dried over Na$_2$SO$_4$. Rotary evaporation of the solvent and purification by column chromatography (SiO$_2$, heptane/EtOAc 3%) afforded 55 (4.47 g, 21 mmol, 89% yield) as a colorless oil. $^1$H-NMR (CDCl$_3$): δ 0.8-1.9 (m), 1.05 (s) and 1.25 (t) (16H), 2.15-2.3 (m, 2H), 4.0-4.2 (q, 2H), 5.4-5.55 (m, 1H), 5.65-5.75 (m, 1H).

A flask fitted with a Mercury-lamp and connected to a pump and a column filled with 10% silver(I)nitrate impregnated silicagel (36 g, having some normal grade silicagel on the bottom), was filled with a mixture of heptane/Et$_2$O 3:1 v/v (approx. 500 mL). After addition of a solution of 55 (4.47 g, 21.3 mmol) and methyl benzoate (2.7 mL, 21.3 mmol) in a small amount of Et$_2$O, the Mercury-lamp was switched on. After 20 h of irradiation with a continuous flow of the irradiated solution through the column, no starting material was observed in an NMR analysis of the reactor content and the column was washed with 30% MTBE in heptane. The column content was treated with ammonia and extracted with CH$_2$Cl$_2$ (3×). The combined organic layers were dried over Na$_2$SO$_4$ and after evaporation of the solvent and purification by column chromatography (SiO$_2$, heptane/EtOAc gradient 3%>4%) compound 56 (1.41 g, 6.7 mmol, 31% yield) was obtained as a colorless oil. The major and minor isomers were inseparable and therefore the isomers were used further as a mixture.

$^1$H-NMR (CDCl$_3$): δ 0.8-1.9 (m), 1.0 (s) and 1.25 (t) (16H), 2.1-2.4 (m, 2H), 4.0-4.2 (q, 2H), 5.5-5.65 (m, 2H).

A solution of lithium hydroxide monohydrate (84 mg, 2.0 mmol) in water (1 mL) and EtOH (1 mL) was added to 56 (210 mg, 1.0 mmol). For better dissolution of the compound THF (1 mL) and MeOH (2 mL) were added. After 16 h of stirring at RT the conversion was not yet complete. Extra lithium hydroxide (85 mg) was added and the mixture was heated to 45° C. for 4 h, 16 h at 30° C. and 4 h at 50° C. until the conversion was complete. The mixture was concentrated in vacuo and neutralized with a citric acid solution. After extraction with MTBE (3×) and drying over Na$_2$SO$_4$, the rotary evaporation of the solvent afforded 57 (150 mg, 0.82 mmol, 82% yield) as a yellow oil.

$^1$H-NMR (CDCl$_3$): δ 1.0 (2s, 3H), 1.3-2.0 (m, 10H), 2.1-2.45 (m, 2H), 5.5-5.65 (m, 2H).

To an ice cooled solution of 57 (150 mg, 0.82 mmol) and N-hydroxysuccinimide (113 mg, 0.98 mmol) in THF (5 mL) was added a solution of DCC (170 mg, 0.82 mmol) in THF (1 ml). The mixture was stirred for 16 h at RT and was then diluted with MTBE. The precipitate was removed by filtration and after evaporation of the solvent and purification by column chromatography (SiO$_2$, heptane/EtOAc gradient 10%>30%) compound 58 (197 mg, 0.71 mmol, 86% yield) was obtained as a colorless oil.

$^1$H-NMR (CDCl$_3$): δ 1.05 and 1.1 (2s, 3H), 1.35-2.35 (m, 10H), 2.4 (s, 1H), 2.5-2.75 (AB, 1H), 2.85 (s, 4H), 5.5-5.65 (m, 2H).

Example 13

Reaction Kinetics of New TCOs

The newly synthesized TCO constructs were evaluated with respect to their reactivity towards tetrazine 28. The procedures are described in Example 5.

TABLE 7

Second order kinetic constants of the reactions between CC49-TCO constructs and $^{177}$Lu-28.

| TCO | $[M^{-1}s^{-1}]$ |
|---|---|
| 44a | 20640 ± 485 |
| 44b | 134800 ± 997 |
| 46a | 28630 ± 1590 |
| 46b | 163200 ± 2871 |
| 49a | 25080 ± 3865 |
| 49b | 148500 ± 12040 |
| 52a | 20930 ± 3735 |
| 52b | 333300 ± 625 |
| 58 | 323500 ± 43320 |

For all TCOs there is a profound and consistent reactivity difference between the major (equatorial) and the minor (axial) isomers, the latter being far more reactive than the former. Furthermore, the high reactivity of TCO 58, supports that substituents in the axial position without a linker to an antibody still afford increased reactivity of the transcyclooctene ring.

Example 14

Stability and Reactivity of Novel Model Tetrazine Probes

Several tetrazine model probes comprising alternative tetrazine moieties were assessed with respect to their reactivity and stability in water.

Hydrolyic Stability Tests of Tetrazines

10 μL of a solution of the specific tetrazine in DMSO (25 mM) was diluted with PBS buffer (3 mL), and this solution was filtered. Using UV spectroscopy, the decrease of the absorption band at 525 nm was monitored, and from this data the rate of hydrolysis and half-life time was determined.

Reactivity of Tetrazines Towards trans-cyclooct-4-ene-1-ol (minor isomer, 10b)

A competition experiment was performed to determine the reactivity ratio of a specific tetrazine and 3-(5-acetamido-2-pyridyl)-6-(2-pyridyl)-1,2,4,5-tetrazine (that was chosen as the reference tetrazine), in the inverse-electron demand Diels-Alder reaction with trans-cyclooct-4-ene-1-ol (minor isomer, 10b).

To acetonitrile (0.100 mL) was added 5 μL of a solution of the specific tetrazine in DMSO (25 mM) and 5 μL of a solution of the reference tetrazine in DMSO (25 mM). This mixture was diluted with water (0.9 mL), and the absolute amounts of both tetrazines were determined by LC-MS/PDA analysis. Subsequently, a solution of trans-cyclooct-4-ene-1-ol (minor isomer, 10b) in DMSO (25 μL 2.5 mM) was added, and the mixture was stirred for 5 min. Again, the absolute amounts of both tetrazines were determined by LC-MS/PDA analysis, and conversions for both tetrazines was calculated. From these conversions, the reactivity ratio of both tetrazines was determined.

TABLE 8 reactivity and stability of model tetrazine probes

| Tetrazine | $k_2/k_{2\,ref}$ | $t_{1/2}$ (h) | solvent |
|---|---|---|---|
| 35 | 1.84 | 35 | ACN/PBS |
| 38 | 0.95 | 117 | PBS |
| 40 | 0.25 | 230 | PBS |
| 42 | 0.83 | 2.4 | PBS |

From Table 8 it becomes clear that the substituents on the tetrazine have a profound effect on stability and reactivity and as such can be used in the design of probes tailored to a particular application.

Example 15

In Vitro Reactivity Difference Major vs Minor TCO, 20a vs 20b, with Tetrazine Probe 28

Figure 18:
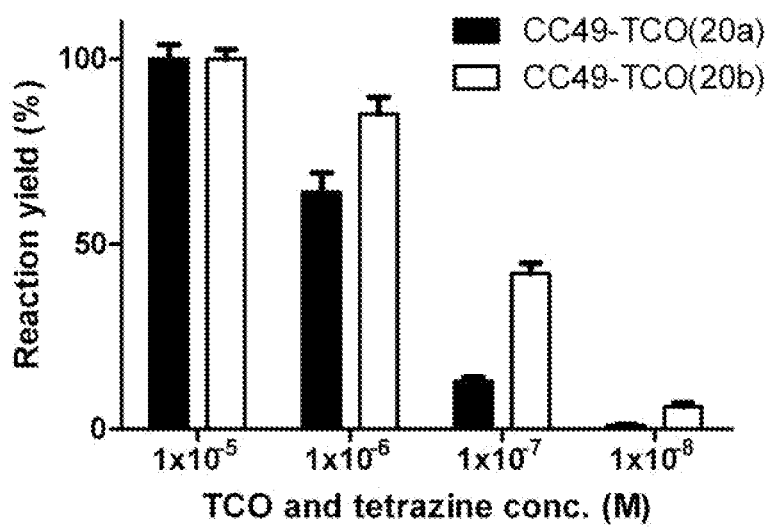
FIG. 18 provides normalized reaction yields between TCO (20a or 20b) and carrier added $^{177}$Lu-tetrazine 28 (1 eq.) in PBS at low concentration.

This experiment was carried out to demonstrate that higher TCO reactivity translates into higher reaction yields with radio labeled tetrazine at low concentration of both reagents. To this aim we used a TCO major 20a ($k_2$=19600±1400 $M^{-1}s^{-1}$) and a TCO minor 20b ($k_2$=136700±2300 $M^{-1}s^{-1}$) conjugated to CC49 (6.1 and 6.6 TCOs per molecule for major and minor, respectively). The two mAb solutions were diluted in PBS to obtain TCO concentrations ranging from $1\times10^{-5}$M to $1\times10^{-8}$M and were reacted with carrier-added $^{177}$Lu-tetrazine (1 eq. with respect to mAb) for 1 min at 37° C. Aliquots of the reaction mixtures (20 μl) where then quenched with an excess of tetrazine 6, added with non-reducing sample buffer and analyzed by SDS-PAGE. The cycloaddition yields were determined from the radioactivity in the bands corresponding to the mAb and the counts were quantified with the AIDA Image Analyzer software. The experiments were repeated in triplicate. As expected for a bimolecular reaction, a decrease in the concentration of the two reactive species in solution translates into lower reaction yields after 1 min incubation (FIG. 18). However, when using the axial TCO 20b the reaction yields are significantly higher than those obtained with the equatorial TCO 20a at micromolar concentrations and lower, due to the faster reaction kinetics with the tertazine.

Example 16

In Vivo Stability of TCO 20b

Figure 19:
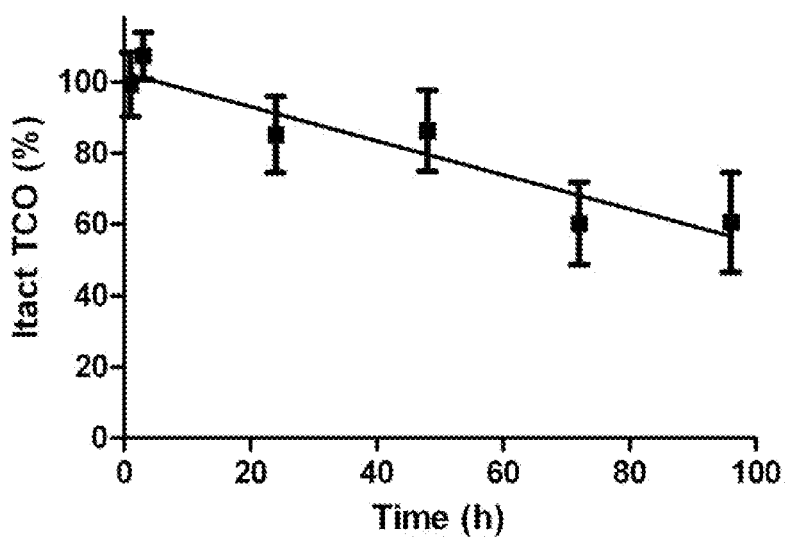
FIG. 19 presents in vivo stability of CC49-bound TCO 20b corrected for blood clearance. The data points represent the mean and the error bars represent one standard deviation (n=3).

This experiment was carried out to expand the series of in vivo TCO stability measurements described in Example 6. In that series, TCOs major and minor bound to CC49 with a PEG spacer (23a and 27b) were found to be unstable in vivo, while a TCO major without PEG spacer (20a) was found to be stable in vivo for at least 4 days (FIG. 13). In the new experiment, following the same procedure, we tested the in vivo stability of a CC49-bound TCO minor without PEG spacer (20b, 6.9 equivalents bound). The in vivo stability data, corrected for mAb clearance, are shown in FIG. 19. The CC49-bound TCO 20b was found to only slowly degrade in vivo, further supporting the finding that TCOs with a short linker to the antibody are more stable in vivo than TCOs conjugated through a longer linker.

Example 17

Blood Kinetics and Biodistribution of CC49 Antibody Functionalized with Range of TCO 20b Moieties A series of studies was carried out to evaluate the influence of the number of TCO (20b) groups per CC49 molecule on blood circulation and tumor targeting. It is expected that modifying the antibody with too many TCO moieties will lead to a decrease in blood circulation half-life and will affect the tumor uptake of the CC49-TCO construct.

Figure 20:
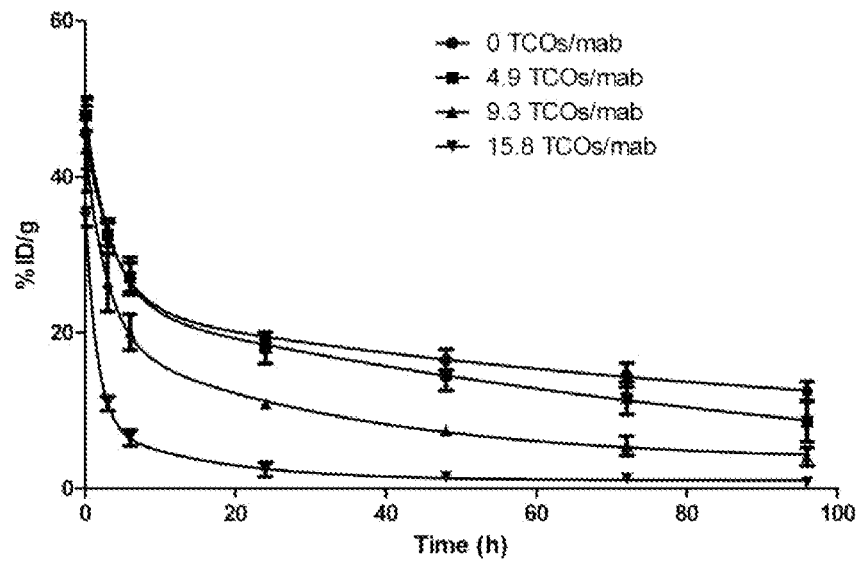
FIG. 20 shows blood curves of CC49-TCO (20b) constructs. Data points represent the mean and error bars represent one standard deviation (n=3).
Figure 21:
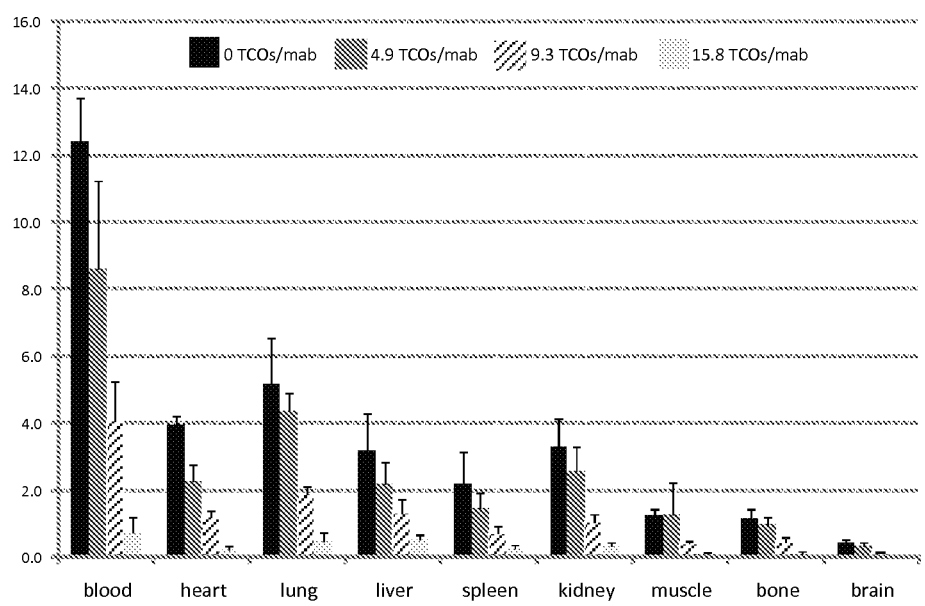
FIG. 21 presents the biodistribution of CC49-TCO (20b) constructs in tumor-free mice. Bars represent the mean and error bars represent one standard deviation (n=3).

Blood Kinetics of CC49-TCO Constructs (See FIGS. 20 and 21)

Nude female Balb/C mice (20-25 g body weight, Charles River Laboratories, n=3) were injected with $^{125}$I—CC49 carrying 0, 4.9, 9.3 or 15.8 TCO (20b) groups per mAb (100 μg/100 μL per mouse, ca. 0.5 MBq). At selected time points (5 min, 3, 6 hours, 1, 2, 3 days) blood samples were withdrawn from the vena saphena, weighed and diluted with 1 mL PBS. Four days after mAb injection the animals were anesthesized and sacrificed by cervical dislocation, blood was collected by heart puncture and organs and tissues of interest were harvested, blotted dry, weighed and added with 1 mL PBS. The radioactivity in all samples was measured in a gamma-counter (Wizard II, Perkin Elmer) along with standards to determine the percent injected dose per gram tissue (% ID/g). The half-life of CC49-TCO constructs in blood was calculated with GraphPad Prism (version 5.01), by fitting the blood curve to a two-phase decay.

TABLE 9

Kinetic blood parameters of CC49-TCO (20b).

| TCO # | $T_{1/2,\alpha}$ (%) | $T_{1/2,\beta}$ | $R^2$ |
|---|---|---|---|
| 0 | 2.6 h (58) | 64.4 h | 0.970 |
| 4.9 | 2.4 h (50) | 74.5 h | 0.983 |
| 9.3 | 2.0 h (61) | 23.5 h | 0.972 |
| 15.8 | 1.1 h (79) | 10.5 h | 0.996 |

Tumor Targeting of CC49-TCO (20b) Constructs

Tumor-bearing mice (see Methods; 100 mm³ tumor size) were injected with $^{125}$I—CC49 functionalized with 0, 8.5, 12.7 or 18.7 TCO 20b groups per mAb (100 μg/100 μL per mouse, 0.2-0.4 MBq, n=4). The mice that received $^{125}$I—CC49 were sacrificed 4 days post mAb injection. The mice that received $^{125}$I—CC49-TCO 20b were injected with $^{111}$In-DOTA-tetrazine 28 at 72 h post-mAb injection (25 eq. with respect to mAb, ca. 0.8 MBq) and were sacrificed 3 h after tetrazine injection. At the time of sacrifice, blood was collected by heart puncture and organs and tissues of interest were harvested, blotted dry, weighed and added with 1 mL PBS. The radioactivity in all samples was measured in a gamma-counter (Wizard 3, Perkin Elmer) with a dual-isotope protocol (energy windows set to 10-80 keV and 100-510 keV for $^{125}$I and $^{111}$In, respectively) along with standards to determine the percent injected dose per gram tissue (% ID/g).

TABLE 10

Biodistribution of $^{125}$I-CC49-TCO 20b constructs in tumor bearing mice 3 days post mAb injection (except *). Data presented as mean % ID/g ± SD (n = 4)

| Organ | CC49* | CC49-TCO (8.5) | CC49-TCO (12.7) | CC49-TCO (18.2)** |
|---|---|---|---|---|
| Blood | 6.80 ± 3.84 | 1.53 ± 0.55 | 0.89 ± 0.79 | 0.13 ± 0.08 |
| Tumor | 73.82 ± 21.37 | 19.63 ± 4.92 | 10.58 ± 5.62 | 2.58 ± 0.61 |
| Heart | 1.83 ± 0.55 | 0.53 ± 0.18 | 0.28 ± 0.14 | 0.07 ± 0.02 |
| Lung | 4.18 ± 1.53 | 1.06 ± 0.28 | 0.70 ± 0.29 | 0.21 ± 0.05 |
| Liver | 3.61 ± 1.05 | 3.44 ± 0.47 | 1.18 ± 0.18 | 0.64 ± 0.15 |
| Spleen | 1.95 ± 0.78 | 1.07 ± 0.19 | 0.59 ± 0.14 | 0.34 ± 0.04 |
| Kidney | 2.22 ± 0.99 | 0.66 ± 0.21 | 0.45 ± 0.25 | 0.13 ± 0.03 |
| Muscle | 1.11 ± 0.26 | 0.35 ± 0.23 | 0.09 ± 0.03 | 0.03 ± 0.01 |
| Bone | 0.90 ± 0.30 | 0.25 ± 0.07 | 0.16 ± 0.07 | 0.06 ± 0.02 |
| Brain | 0.30 ± 0.22 | 0.05 ± 0.02 | 0.03 ± 0.02 | 0.01 ± 0.01 |

*Mice sacrificed 4 days after mAb injection
**Low immunoreactivity

TABLE 11

Biodistribution of $^{111}$In-tetrazine 28 (3 h post-injection) in mice pretreated with CC49-TCO 20b constructs. Data presented as mean % ID/g ± SD (n = 4)

| Organ | CC49-TCO(8.5) | CC49-TCO(12.7) | CC49-TCO(18.2) |
|---|---|---|---|
| Blood | 0.45 ± 0.14 | 0.37 ± 0.28 | 0.12 ± 0.03 |
| Tumor | 3.72 ± 1.45 | 3.36 ± 1.69 | 1.21 ± 0.22 |
| Heart | 0.16 ± 0.03 | 0.13 ± 0.05 | 0.09 ± 0.03 |
| Lung | 0.42 ± 0.06 | 0.34 ± 0.10 | 0.29 ± 0.01 |
| Liver | 0.44 ± 0.12 | 0.29 ± 0.12 | 0.26 ± 0.05 |
| Spleen | 0.25 ± 0.05 | 0.20 ± 0.06 | 0.20 ± 0.02 |
| Kidney | 1.64 ± 0.28 | 1.25 ± 0.24 | 2.15 ± 0.17 |
| Muscle | 0.11 ± 0.05 | 0.05 ± 0.00 | 0.29 ± 0.43 |
| Bone | 0.10 ± 0.03 | 0.08 ± 0.02 | 0.10 ± 0.02 |
| Brain | 0.02 ± 0.01 | 0.01 ± 0.01 | 0.04 ± 0.05 |

From the data in Tables 9-11, it becomes clear that the TCO modification ratio should not exceed 9.

Example 18

Blood Kinetics and In Vivo Stability of CC49-TCO 44b

Blood Kinetics

Tumor-free mice (n=3 per group) were injected with $^{125}$I-labeled CC49 of CC49 modified with 7.5 TCO 44b groups (100 μg/mouse, 0.2-0.4 MBq). At selected time points (1, 3, 6, 24, 48, and 72 hours) blood samples were withdrawn from the vena saphena and collected in vials containing heparin. Four days after mAb injection, the mice were anesthetized and sacrifice by cervical dislocation. Blood was withdrawn by heart puncture and organs and tissues of interest were harvested, blotted dry, weighed, added with 1 ml PBS and counted in a gamma counter (Wizard 3, Perkin Elmer) along with standards to determine the percent injected dose (% ID) per organ.

Figure 22:
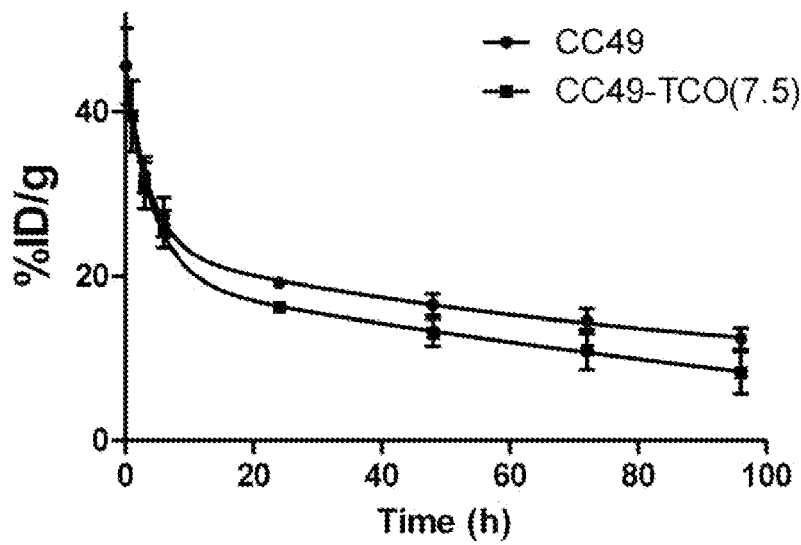
FIG. 22 shows blood kinetics of $^{125}$I—CC49 and $^{125}$I—CC49-TCO 44b (7.5) in tumor-free mice (n=3). Data are presented as percent injected dose per gram (% ID/g) with one standard deviation (error bar)
Figure 23:
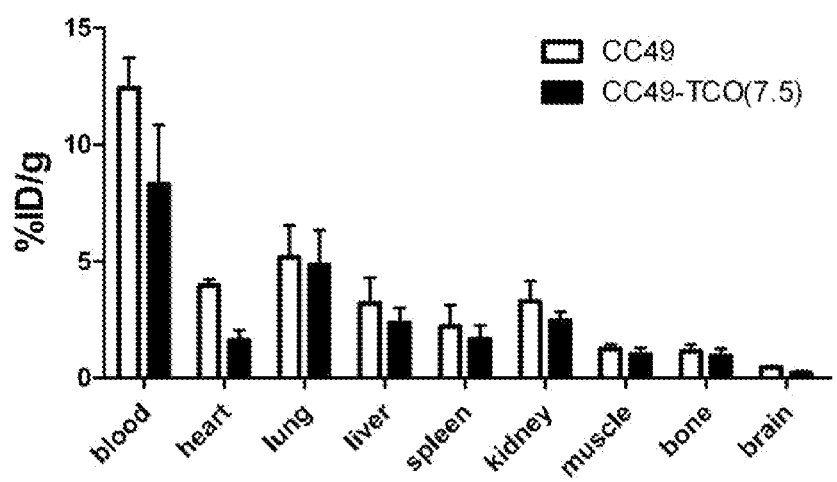
FIG. 23 presents the biodistribution of $^{125}$I—CC49 (empty bars) and $^{125}$I—CC49-TCO 44b (7.5) (solid bars) in tumor-free mice (n=3) 4 days post-mAb injection. The bars percent injected dose per gram (% ID/g) with one standard deviation (error bar).

In this study, TCO-modified CC49 exhibited a slightly faster clearance compared to unmodified CC49 (FIG. 22). The half-life in blood calculated from the area under the curve ($T_{1/2}$=ln 2×AUC/$C_0$) was 22.2 hours and 26.3 hours for CC49-TCO and CC49, respectively. We attribute this to the functionalization of Lys residues on the mAb. As a result of the shorter blood circulation, lower amounts of $^{125}$I—CC49-TCO were also observed in most organs, which were not perfused before counting, at the end of the experiment (FIG. 23).

In Vivo Stability

A separate group of tumor-free mice (n=3) was injected with $^{125}$I-labeled CC49-TCO 44b (220 μg/mouse, 0.4 MBq). At selected time points (1, 3, 6, 24, 48, and 72 hours) blood samples (ca. 50 μl) were withdrawn from the vena saphena and collected in vials containing heparin. Four days after mAb injection, the mice were anesthetized and sacrifice by cervical dislocation. Blood was withdrawn by heart puncture and stomachs and thyroids were removed, blotted dry and counted in a gamma-counter along with standards to determine the percent injected dose (% ID) per organ. The low $^{125}$I uptake in these organs (0.17±0.03% ID in stomach and 0.88±0.33% ID in thyroid) confirms that the radiolabeled mAb retained the label in vivo during the 4 days evaluation.

Figure 24:
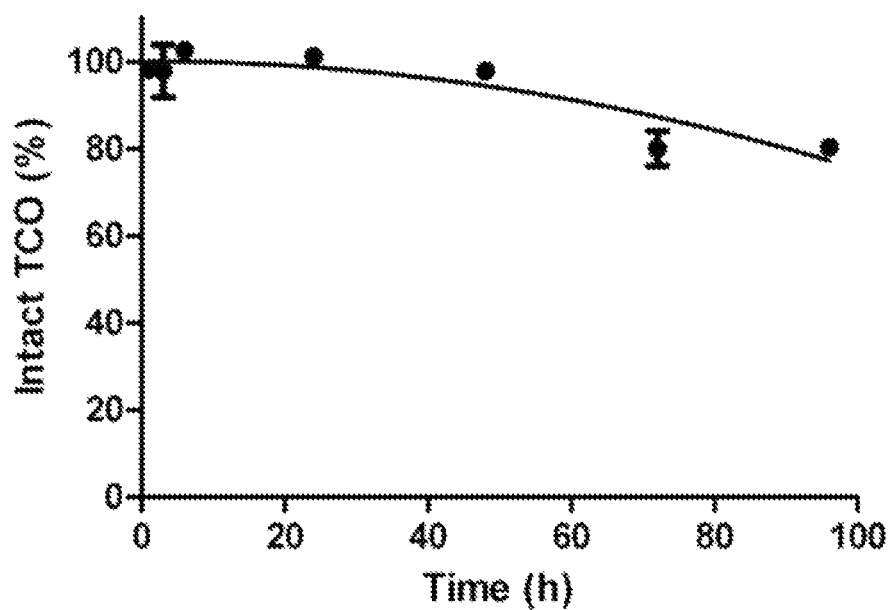
FIG. 24 shows the in vivo stability of TCO 44b conjugated to CC49. The data points are the mean of three measurements with one standard deviation (error bar) fitted to a second order polynomial (Prism GraphPad v. 5.01).

The blood samples were weighed, diluted with PBS to 100 μl and added with an excess of carried added $^{177}$Lu-tetrazine 28 radiolabeled at 0.1 MBq/μg specific activity. The mixtures were incubated for 20 min at 37° C. and centrifuged for 5 min at 400×g to separate blood cells. Then 30 μl supernatant was applied to a Zeba Desalt spin-column (0.5 ml, 40 kDa MW cut-off, Pierce). After centrifugation, the high MW Diels-Alder reaction product was eluted from the cartridge while the excess tetrazine was retained. The radioactivity contained in the eluates was measured in a gamma-counter with a dual-isotope protocol (10-80 keV window for $^{125}$I and 155-380 keV window for $^{177}$Lu). A serum sample containing $^{177}$Lu-tetrazine alone was used to correct for $^{177}$Lu leakage from the cartridge. The $^{125}$I counts were corrected for radioactive decay and then the $^{177}$Lu/$^{125}$I ratio was calculated. A decrease in the $^{177}$Lu/$^{125}$I ratio signifies a lower reaction yield between the excess $^{177}$Lu-tetrazine and $^{125}$I—CC49-TCO present in the mouse blood samples and, therefore, deactivation of the TCO groups in vivo. FIG. 24 shows the change of $^{177}$Lu/$^{125}$I ratio with time as % intact TCO (normalized to 100% at t=0). Noteworthy, the TCO 44b groups appear completely stable in vivo up to 48 hours post-mAb injection (97.8±1.6% intact TCO) while some degradation was observed at later time points (80.4±1.8% intact TCO 4 days post-mAb injection).

Example 19

Biodistribution of $^{177}$Lu-Tetrazine 28 in Tumor Bearing Mice Pretargeted with CC49-TCO 44b Tumor-bearing mice (see Methods; 100 mm$^3$ tumor size; n=4) were injected with $^{125}$I-CC49 functionalized with 7.5 TCO 44b groups (100 μg/mouse, ca. 0.2 MBq). Thirty and 48 hours post-mAb injection the mice received one dose of clearing agent (galactose-MSA-tetrazine, 160 μg/dose) followed 2 h later by $^{177}$Lu-tetrazine 28 (10 eq. with respect to the mAb, ca. 0.5 MBq). Three hours post-tetrazine injection the mice were anesthetized and sacrificed by cervical dislocation, blood was withdrawn by heart puncture, organs and tissues of interest were harvested and blotted dry. All collected samples were weighed and added with 1 mL PBS. The sample radioactivity was measured in a gamma-counter with a dual-isotope protocol (10-80 keV window for $^{125}$I and 155-380 keV window for $^{177}$Lu) along with standards to determine the percent injected dose per gram tissue (% ID/g).

The biodistribution data show high tumor uptake of $^{125}$I—CC49-TCO 44b. The tumor uptake was higher than that obtained with other TCO constructs (vide infra), reasonably due to the long blood circulation of CC49 functionalized with 7.5 TCO-44b groups. On the contrary, the mAb retention in all other organs was low due to the administration of two doses of a clearing agent that captured the circulating CC49-TCO and directed it to the liver, where it was rapidly metabolized. As a result of the higher mAb uptake in tumor, also the $^{177}$Lu-tetrazine uptake was significantly higher than that obtained in previous experiments (vide infra). Also, due to the removal of non-tumor bound CC49-TCO in the chase step before tetrazine administration, $^{177}$Lu uptake in all other organs was negligible. Only kidney exhibited a rather high retention of $^{177}$Lu as a consequence of tetrazine urinary excretion. This resulted in high target-to-non target ratios in all considered organs beside kidney. Noteworthy, 34±4% and 10±1% of the TCOs present in tumor and blood respectively had reacted with tetrazine.

TABLE 12

Dual isotope biodistribution data 3 h after injection of $^{177}$Lu-tetrazine 28 (8.5 μg/80 μL per mouse, ca. 0.5 MBq), 50 h after the administration of $^{125}$I-CC49-TCO-44b (100 μg/100 μL per mouse, ca. 0.2 MBq). Data presented as % ID/gram ± SD or tumor/organ ratio ± SD (n = 4).

| | % ID/organ | | Tumor/organ | |
|---|---|---|---|---|
| | $^{125}$I-CC49-TCO | $^{177}$Lu-tetrazine | $^{125}$I-CC49-TCO | $^{177}$Lu-tetrazine |
| Tumor | 32.88 ± 4.35 | 9.25 ± 2.16 | | |
| Blood | 0.31 ± 0.13 | 0.03 ± 0.00 | 129 ± 74 | 304 ± 80 |
| Heart | 0.62 ± 0.22 | 0.05 ± 0.01 | 60 ± 26 | 187 ± 20 |

TABLE 12-continued

Dual isotope biodistribution data 3 h after injection of $^{177}$Lu-tetrazine 28 (8.5 μg/80 μL per mouse, ca. 0.5 MBq), 50 h after the administration of $^{125}$I-CC49-TCO-44b (100 μg/100 μL per mouse, ca. 0.2 MBq). Data presented as % ID/gram ± SD or tumor/organ ratio ± SD (n = 4).

| | % ID/organ | | Tumor/organ | |
|---|---|---|---|---|
| | $^{125}$I-CC49-TCO | $^{177}$Lu-tetrazine | $^{125}$I-CC49-TCO | $^{177}$Lu-tetrazine |
| Lung | 0.99 ± 0.24 | 0.24 ± 0.02 | 35 ± 8 | 39 ± 8 |
| Liver | 2.35 ± 0.82 | 0.19 ± 0.02 | 16 ± 6 | 50 ± 10 |
| Spleen | 0.67 ± 0.07 | 0.09 ± 0.01 | 49 ± 5 | 108 ± 22 |
| Kidney | 0.47 ± 0.10 | 1.50 ± 0.24 | 72 ± 14 | 6 ± 2 |
| Muscle | 0.22 ± 0.08 | 0.03 ± 0.00 | 162 ± 62 | 328 ± 96 |
| Bone | 0.29 ± 0.08 | 0.08 ± 0.04 | 119 ± 33 | 142 ± 59 |
| Brain | 0.02 ± 0.00 | 0.01 ± 0.00 | 2304 ± 668± | 1674 ± 243 |

SOME EMBODIMENTS RELATE TO

1. A kit for targeted medical imaging and/or therapeutics, comprising at least one Pre-targeting Probe and at least one Effector Probe, wherein the Pre-targeting Probe comprises a Primary Targeting Moiety and a first Bio-orthogonal Reactive Group, and wherein the Effector Probe comprises an Effector Moiety, such as a label or a pharmaceutically active compound, and a second Bio-orthogonal Reactive Group, wherein either of the first and second Bio-orthogonal Reactive Groups is a dienophile and the other of the first and second Bio-orthogonal Reactive Groups is a diene, wherein the dienophile is an 8-member ring dienophile satisfying formula (1):

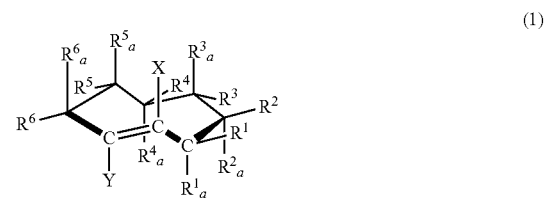

(1)

wherein the position of R is equatorial and the position of $R_a$ is axial, wherein each of X, Y, R, and $R_a$ independently denotes H, or, in at most six instances, a substituent selected from the group consisting of alkyl, aryl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, N$_3$, SO$_2$H, SO$_3$H, SO$_4$H, PO$_4$H, OH, SH, NO$_2$, NO, CN, OCN, SCN, NCO, NCS, CF$_3$, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl; with one of R or $R_a$ comprised in a Linker Moiety, optionally via a spacer, to the Pre-targeting Probe or the Effector Probe; wherein two R or $R_a$ moieties together may form a ring; and wherein at least one and maximally four of $R_a$ is not hydrogen.

2. A kit according to embodiment 1, wherein the dienophile of formula 1 satisfies one or more of the following requirements:
  a) X is methyl
  b) Y is methyl;
  c) one or more substituents $R^2_a$, $R^3_a$, $R^4_a$, $R^5_a$ are O-alkyl;
  d) one or more substituents $R^2_a$, $R^3_a$, $R^4_a$, $R^5_a$ are O-aryl;
  e) one or more substituents $R^2_a$, $R^3_a$, $R^4_a$, $R^5_a$ are aryl;

3. A kit according to embodiment 1 or 2, wherein X is methyl or hydrogen, Y is methyl or hydrogen, and $R^3_a$ or $R^4_a$ is O-alkyl or O-aryl.

4. A kit according to any one of the preceding embodiments, wherein the Linker Moiety is attached to an O-alkyl or O-aryl moiety on $R^3_a$.

5. A kit according to any one of the preceding embodiments, wherein the diene is selected from the group consisting of compounds of the formulae (2), (3), (4), and (5) as defined below:

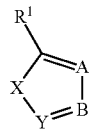
(2)

wherein $R^1$ is selected from the group consisting of H, alkyl, aryl, $CF_3$, $CF_2$—R', OR', SR', C(=O)R', C(=S)R', C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", NR'C(=O)NR'"R"', NR'C(=S)N'R"R"' with R', R", and R'" each independently being H, aryl or alkyl; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)OR', C(=O)SR', C(=S)OR', C(=S)SR', C(=O)NR'R" with R' and R" each independently being H, aryl or alkyl;

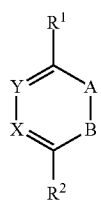
(3)

wherein $R^1$ and $R^2$ each independently are selected from the group consisting of H, alkyl, aryl, $CF_3$, $CF_2$—R', NO$_2$, OR', SR', C(=O)R', C(=S)R', OC(=O)R'", SC(=O)R'", OC(=S)R'", SC(=S)R'", S(=O)R', S(=O)$_2$R'", S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R"R"' with R' and R" each independently being H, aryl or alkyl, and R'" independently being aryl or alkyl; A is selected from the group consisting of N-alkyl, N-aryl, C=O, and CN-alkyl; B is O or S; X is selected from the group consisting of N, CH, C-alkyl, C-aryl, CC(=O)R', CC(=S)R', CS(=O)R', CS(=O)$_2$R'", CC(=O)O—R', CC(=O)S—R', CC(=S)O—R', CC(=S)S—R', CC(=O)NR'R", CC(=S)NR'R", R' and R" each independently being H, aryl or alkyl and R'" independently being aryl or alkyl; Y is selected from the group consisting of CH, C-alkyl, C-aryl, N, and $N^+O^-$;

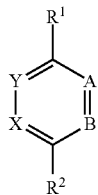
(4)

wherein $R^1$ and $R^2$ each independently are selected from the group consisting of H, alkyl, aryl, $CF_3$, $CF_2$—R', NO$_2$, OR', SR', C(=O)R', C(=S)R', OC(=O)R'", SC(=O)R'", OC(=S)R'", SC(=S)R'", S(=O)R', S(=O)$_2$R'", S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R"R"' with R' and R" each independently being H, aryl or alkyl, and R' independently being aryl or alkyl; A is selected from the group consisting of N, C-alkyl, C-aryl, and $N^+O^-$; B is N; X is selected from the group consisting of N, CH, C-alkyl, C-aryl, CC(=O)R', CC(=S)R', CS(=O)R', CS(=O)$_2$R'", CC(=O)O—R', CC(=O)S—R', CC(=S)O—R', CC(=S)S—R', CC(=O)NR'R", CC(=S)NR'R", R' and R" each independently being H, aryl or alkyl and R'" independently being aryl or alkyl; Y is selected from the group consisting of CH, C-alkyl, C-aryl, N, and $N^+O^-$;

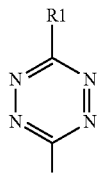
(5)

wherein $R^1$ and $R^2$ each independently denote a substituent selected from the group consisting of H, 2-pyridyl, 3, pyridyl, 4-pyridyl, 2,6-pyrimidyl, 2,5-pyrimidyl, 3,5-pyrimidyl, 2,4-pyrimidyl, or phenyl, optionally substituted with one or more electron-withdrawing groups such as NO$_2$, F, Cl, $CF_3$, CN, COOH, COOR, CONH$_2$, CONHR, CONR$_2$, CHO, COR, SO$_2$R, SO$_2$OR, NO, Ar, wherein R is $C_1$-$C_6$ alkyl and Ar stands for an aromatic group, particularly phenyl, pyridyl, or naphthyl; and wherein the diene comprises at least one linkage, optionally via a spacer, to the Pre-targeting Probe or the Effector Probe.

6. A kit according to any one of the preceding embodiments, wherein the Pre-targeting Probe comprises, as a primary targeting moiety, an antibody.

7. A kit according to any one of the preceding embodiments, wherein the Effector Probe comprises, as an effector moiety, a detectable label, preferably a contrast agent for use in imaging systems, selected from the group consisting of MRI-imageable agents, spin labels, optical labels, ultrasound-responsive agents, X-ray-responsive agents, radionuclides, FRET-type dyes, (bio)luminescent or fluorescent molecules or tags, biotin, paramagnetic imaging reagents and superparamagnetic imaging reagents.

8. A kit according to any one of the preceding embodiments, wherein the Effector Probe comprises, as an Effector moiety, a pharmaceutically active compound.

9. A kit according to embodiment 8, wherein the pharmaceutically active compound is an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac.

10. A pretargeting agent comprising a primary targeting moiety and a bio-orthogonal reactive group, wherein the bio-orthogonal reactive group is a reaction partner for a [4+2] retro Diels-Alder reaction between a diene according to any one of the formulae (2)-(5) as defined in embodiment 5, and a dienophile according to formula (1) as defined in any one of the embodiments 1 to 4.

11. An imaging probe comprising a detectable label, preferably an isotope selected from the group consisting of $^{3}$H, $^{11}$C, $^{13}$N, $^{15}$O, $^{18}$F, $^{19}$F, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, and $^{203}$Pb and a bio-orthogonal reactive group, wherein the bio-orthogonal reactive group is a reaction partner for a [4+2] retro Diels-Alder reaction between a diene according to any one of the formulae (2)-(5) as defined in embodiment 5, and a dienophile according to formula (1) as defined in any one of the embodiments 1 to 4.

12. A therapeutic probe comprising a pharmaceutically active compound, preferably an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac, and a bio-orthogonal reactive group, wherein the bio-orthogonal reactive group is a reaction partner for a [4+2] retro Diels-Alder reaction between a diene according to any one of the formulae (2)-(5) as defined in embodiment 5, and a dienophile according to formula (1) as defined in any one of the embodiments 1 to 4.

13. A pretargeting method comprising administering a pretargeting agent according to embodiment 10 to a subject and allowing the agent to circulate in the subject's system for a period of time effective to achieve binding of the primary targeting moiety to a primary target, followed by clearing non-bound agent from the body.

14. An imaging method comprising conducting a pretargeting method according to embodiment 13, followed by the administration of an imaging probe according to embodiment 11, wherein the bio-orthogonal reactive groups in the pretargeting agent and in the imaging probe together form the reactive partners for said [4+2] retro Diels-Alder reaction.

15. A method of targeted medical treatment in a subject, comprising conducting a pretargeting method according to embodiment 13, followed by the administration of a therapeutic probe according to embodiment 12, wherein the bio-orthogonal reactive groups in the pretargeting agent and in the therapeutic probe together form the reactive partners for said [4+2] retro Diels-Alder reaction.

16. An agent according to embodiment 10 for use in a method according to any one of the embodiments 13 to 15.

17. A compound satisfying formula (1) as defined in any one of the embodiments 1 to 4, for use in a pre-targeting method in an animal or a human being.

18. The use of a trans cyclooctene having one or more axial substituents, preferably a compound satisfying formula (1) as defined in any one of the embodiments 1 to 4, as a dienophile reactant in a pre-targeting method based on the retro Diels-Alder reaction.

19. A kit for targeted medical imaging and/or therapeutics, comprising at least one Pre-targeting Probe and at least one Effector Probe, wherein the Pre-targeting Probe comprises a Primary Targeting Moiety and a first Bio-orthogonal Reactive Group, and wherein the Effector Probe comprises an Effector Moiety, such as a label or a pharmaceutically active compound, and a second Bio-orthogonal Reactive Group, wherein either of the first and second Bio-orthogonal Reactive Groups is a dienophile and the other of the first and second Bio-orthogonal Reactive Groups is a diene, wherein the dienophile is an 8-member ring dienophile satisfying formula (1):

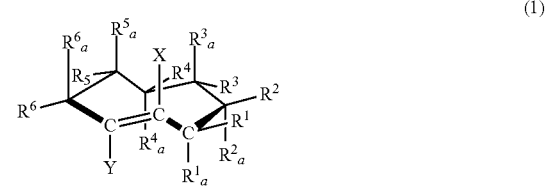

wherein the position of R is equatorial and the position of $R_a$ is axial, wherein each of X, Y, R, and $R_a$ independently denotes H, or, in at most six instances, a substituent selected from the group consisting of alkyl, O-alkyl, O-aryl, S-alkyl, Si-alkyl, F, Cl, Br, I, $SO_2$, $SO_3$, $SO_4$, $NO_2$, NR'R" with R' and R" each independently being H or alkyl, C(=O)O alkyl, C(=O)O aryl, CONR'R" with R' and R" each independently being H, aryl or alkyl, OCO alkyl, OCO aryl, NR'CO alkyl with R' being H or alkyl, NR'CO aryl with R' being or alkyl, NR'C(=O)O alkyl with R' being H or alkyl, NR'C(=O)O aryl with R' being H or alkyl, OCONR' alkyl with R' being H or alkyl, OCONR' aryl with R' being H or alkyl, NR'CONR" alkyl with R' and R" each independently being H or alkyl, NR'CONR" aryl with R' and R" each independently being H or alkyl, NR'CSNR" alkyl with R' and R" each independently being H or alkyl, and NR'CSNR" aryl with R' and R" each independently being H or alkyl; with one of $R_a$ comprised in a Linker Moiety, optionally via a spacer, to the Pre-targeting Probe or the Effector Probe; wherein two R or $R_a$ moieties together may form a ring; and wherein at least one and maximally four of $R_a$ is not hydrogen.

20. A kit according to embodiment 19, wherein the dienophile of formula 1 satisfies one or more of the following requirements:
   a) X is methyl
   b) Y is methyl;
   c) one or more substituents $R^2_a$, $R^3_a$, $R^4_a$, $R^5_a$ are O-alkyl;
   d) one or more substituents $R^2_a$, $R^3_a$, $R^4_a$, $R^5_a$ are O-aryl;
21. A kit according to embodiment 19 or 20, wherein X is methyl or hydrogen, Y is methyl or hydrogen, and $R^3_a$ or $R^4_a$ is O-alkyl or O-aryl.
22. A kit according to any one of embodiments 19 to 21, wherein the Linker Moiety is attached to an O-alkyl or O-aryl moiety on $R^3_a$.
23. A kit according to any one of embodiments 19 to 22, wherein the diene is selected from the group consisting of compounds of the formulae (2), (3), (4), and (5) as defined below:

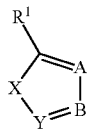

(2)

wherein $R^1$ is selected from the group consisting of alkyl, aryl, O-alkyl, C(=O)O-alkyl, O—, and $NH_2$; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)O alkyl;

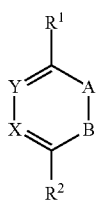

(3)

wherein $R^1$ and $R^2$ each independently are selected from the group consisting of H, alkyl, aryl, OH, C(=O)O-alkyl, CF3, C(=O)NH-alkyl, and NO2; A is selected from the group consisting of N-alkyl, N-aryl, C=O, and CN-alkyl; B is O; X is selected from the group consisting of CH, C-alkyl, C-aryl, CC(=O)O-alkyl and N; Y is selected from the group consisting of CH, C-alkyl, C-aryl, N, and $N^+O^-$.

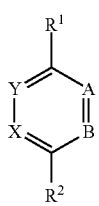

(4)

wherein $R^1$ and $R^2$ each independently are selected from the group consisting of H, alkyl, aryl, OH, C(=O)O-alkyl, CF3, C(=O)NH-alkyl, and NO2; A is selected from the group consisting of N, C-alkyl, C-aryl, and $N^+O^-$; B is N; X is selected from the group consisting of CH, C-alkyl, C-aryl, CC(=O)O-alkyl and N; Y is selected from the group consisting of CH, C-alkyl, C-aryl, N, and $N^+O^-$;

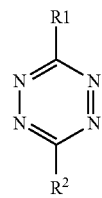

(5)

wherein $R^1$ and $R^2$ each independently denote a substituent selected from the group consisting of 2-pyridyl, phenyl, or phenyl substituted with one or more electron-withdrawing groups such as NO2, CN, COOH, COOR, $CONH_2$, CONHR, $CONR_2$, CHO, COR, $SO_2R$, $SO_2OR$, NO, Ar, wherein R is $C_1$-$C_6$ alkyl and Ar stands for an aromatic group, particularly phenyl, pyridyl, or naphthyl.
24. A kit according to any one of embodiments 19 to 23, wherein the Pre-targeting Probe comprises, as a primary targeting moiety, an antibody.
25. A kit according to any one of embodiments 19 to 24, wherein the Effector Probe comprises, as an effector moiety, a detectable label, preferably a contrast agent for use in imaging systems, selected from the group consisting of MRI-imageable agents, spin labels, optical labels, ultrasound-responsive agents, X-ray-responsive agents, radionuclides, FRET-type dyes, (bio)luminescent or fluorescent molecules or tags, biotin, paramagnetic imaging reagents and superparamagnetic imaging reagents.
26. A kit according to any one of embodiments 19 to 25, wherein the Effector Probe comprises, as an Effector moiety, a pharmaceutically active compound.
27. A kit according to embodiment 26, wherein the pharmaceutically active compound is an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac.
28. A pretargeting agent comprising a primary targeting moiety and a bio-orthogonal reactive group, wherein the bio-orthogonal reactive group is a reaction partner for a [4+2] retro Diels-Alder reaction between a diene according to any one of the formulae (2)-(5) as defined in embodiment 23, and a dienophile according to formula (1) as defined in any one of the embodiments 1 to 4.
29. An imaging probe comprising a detectable label, preferably an isotope selected from the group consisting of $^3$H, $^{11}$C, $^{13}$N, $^{15}$O, $^{18}$F, $^{19}$F, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, and $^{203}$Pb and a bio-orthogonal reactive group, wherein the bio-orthogonal reactive group is a reaction partner for a [4+2] retro Diels-Alder reaction between a diene according to any one of the formulae (2)-(5) as defined in embodiment 23, and a dienophile according to formula (1) as defined in any one of the embodiments 19 to 22.

30. A therapeutic probe comprising a pharmaceutically active compound, preferably an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac, and a bio-orthogonal reactive group, wherein the bio-orthogonal reactive group is a reaction partner for a [4+2] retro Diels-Alder reaction between a diene according to any one of the formulae (2)-(5) as defined in embodiment 23, and a dienophile according to formula (1) as defined in any one of the embodiments 19 to 22.

31. A pretargeting method comprising administering a pretargeting agent according to embodiment 28 to a subject and allowing the agent to circulate in the subject's system for a period of time effective to achieve binding of the primary targeting moiety to a primary target, followed by clearing non-bound agent from the body.

32. An imaging method comprising conducting a pretargeting method according to embodiment 31, followed by the administration of an imaging probe according to embodiment 29, wherein the bio-orthogonal reactive groups in the pretargeting agent and in the imaging probe together form the reactive partners for said [4+2] retro Diels-Alder reaction.

33. A method of targeted medical treatment in a subject, comprising conducting a pretargeting method according to embodiment 31, followed by the administration of a therapeutic probe according to embodiment 30, wherein the bio-orthogonal reactive groups in the pretargeting agent and in the therapeutic probe together form the reactive partners for said [4+2] retro Diels-Alder reaction.

34. An agent according to embodiment 28 for use in a method according to any one of the embodiments 31 to 33.

35. A compound satisfying formula (1) as defined in any one of the embodiments 19 to 22, for use in a pre-targeting method in an animal or a human being.

36. The use of a trans cyclooctene having one or more axial substituents, preferably a compound satisfying formula (1) as defined in any one of the embodiments 19 to 22, as a dienophile reactant in a pre-targeting method based on the retro Diels-Alder reaction.

SOME FURTHER EMBODIMENTS RELATE TO

Embodiment 1

A kit for targeted medical imaging and/or therapeutics, comprising at least one Pre-targeting Probe and at least one Effector Probe, wherein the Pre-targeting Probe comprises a Primary Targeting Moiety and a first Bio-orthogonal Reactive Group, and wherein the Effector Probe comprises an Effector Moiety, such as a label or a pharmaceutically active compound, and a second Bio-orthogonal Reactive Group, wherein either of the first and second Bio-orthogonal Reactive Groups is a dienophile and the other of the first and second Bio-orthogonal Reactive Groups is a diene, wherein the dienophile is an 8-member ring dienophile satisfying formula (1):

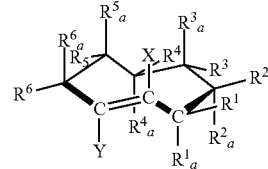

wherein the position of R is equatorial and the position of $R_a$ is axial, wherein each of X, Y, R, and $R_a$ independently denotes H, or, in at most six instances, a substituent selected from the group consisting of alkyl, O-alkyl, O-aryl, S-alkyl, Si-alkyl, F, Cl, Br, I, $SO_2$, $SO_3$, $SO_4$, $NO_2$, NR'R" with R' and R" each independently being H or alkyl, C(=O)O alkyl, C(=O)O aryl, CONR'R" with R' and R" each independently being H, aryl or alkyl, OCO alkyl, OCO aryl, NR'CO alkyl with R' being H or alkyl, NR'CO aryl with R' being or alkyl, NR'C(=O)O alkyl with R' being H or alkyl, NR'C(=O)O aryl with R' being H or alkyl, OCONR' alkyl with R' being H or alkyl, OCONR' aryl with R' being H or alkyl, NR'CONR" alkyl with R' and R" each independently being H or alkyl, NR'CONR" aryl with R' and R" each independently being H or alkyl, NR'CSNR" alkyl with R' and R" each independently being H or alkyl, and NR'CSNR" aryl with R' and R" each independently being H or alkyl; with one of R or $R_a$ comprised in a Linker Moiety, optionally via a spacer, to the Pre-targeting Probe or the Effector Probe; wherein two R or $R_a$ moieties together may form a ring; and wherein at least one and maximally four of $R_a$ is not hydrogen.

Embodiment 2

A kit according to embodiment 1, wherein the dienophile of formula 1 satisfies one or more of the following requirements:

a) X is methyl
b) Y is methyl;
c) one or more substituents $R^2_a$, $R^3_a$, $R^4_a$, $R^5_a$ are O-alkyl;
d) one or more substituents $R^2_a$, $R^3_a$, $R^4_a$, $R^5_a$ are O-aryl;

Embodiment 3

A kit according to embodiment 1 or 2, wherein X is methyl or hydrogen, Y is methyl or hydrogen, and $R^3_a$ or $R^4_a$ is O-alkyl or O-aryl.

Embodiment 4

A kit according to any one of the preceding embodiments, wherein the Linker Moiety is attached to an O-alkyl or O-aryl moiety on $R^3_a$.

Embodiment 5

A kit according to any one of the preceding embodiments, wherein the diene is selected from the group consisting of compounds of the formulae (2), (3), (4), and (5) as defined below:

(2)

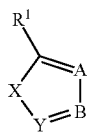

wherein $R^1$ is selected from the group consisting of alkyl, aryl, O-alkyl, C(=O)O-alkyl, O—, and $NH_2$; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)O alkyl;

(3)

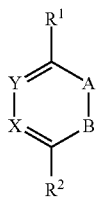

wherein $R^1$ and $R^2$ each independently are selected from the group consisting of H, alkyl, aryl, OH, C(=O)O-alkyl, $CF_3$, C(=O)NH-alkyl, and $NO_2$; A is selected from the group consisting of N-alkyl, N-aryl, C=O, and CN-alkyl; B is O; X is selected from the group consisting of CH, C-alkyl, C-aryl, CC(=O)O-alkyl and N; Y is selected from the group consisting of CH, C-alkyl, C-aryl, N, and $N^+O^-$.

(4)

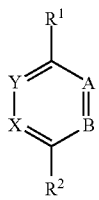

wherein $R^1$ and $R^2$ each independently are selected from the group consisting of H, alkyl, aryl, OH, C(=O)O-alkyl, $CF_3$, C(=O)NH-alkyl, and $NO_2$; A is selected from the group consisting of N, C-alkyl, C-aryl, and $N^+O^-$; B is N; X is selected from the group consisting of CH, C-alkyl, C-aryl, CC(=O)O-alkyl and N; Y is selected from the group consisting of CH, C-alkyl, C-aryl, N, and $N^+O^-$;

(5)

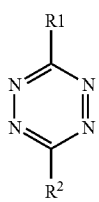

wherein $R^1$ and $R^2$ each independently denote a substituent selected from the group consisting of 2-pyridyl, phenyl, or phenyl substituted with one or more electron-withdrawing groups such as NO2, CN, COOH, COOR, $CONH_2$, CONHR, $CONR_2$, CHO, COR, $SO_2R$, $SO_2OR$, NO, Ar, wherein R is $C_1$-$C_6$ alkyl and Ar stands for an aromatic group, particularly phenyl, pyridyl, or naphthyl.

Embodiment 6

A kit according to any one of the preceding embodiments, wherein the Pre-targeting Probe comprises, as a primary targeting moiety, an antibody.

Embodiment 7

A kit according to any one of the preceding embodiments, wherein the Effector Probe comprises, as an effector moiety, a detectable label, preferably a contrast agent for use in imaging systems, selected from the group consisting of MRI-imageable agents, spin labels, optical labels, ultrasound-responsive agents, X-ray-responsive agents, radionuclides, FRET-type dyes, (bio)luminescent or fluorescent molecules or tags, biotin, paramagnetic imaging reagents and superparamagnetic imaging reagents.

Embodiment 8

A kit according to any one of the preceding embodiments, wherein the Effector Probe comprises, as an Effector moiety, a pharmaceutically active compound.

Embodiment 9

A kit according to embodiment 8, wherein the pharmaceutically active compound is an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac.

Embodiment 10

A pretargeting agent comprising a primary targeting moiety and a bio-orthogonal reactive group, wherein the bio-orthogonal reactive group is a reaction partner for a [4+2] retro Diels-Alder reaction between a diene according to any one of the formulae (2)-(5) as defined in embodiment 5, and a dienophile according to formula (1) as defined in any one of the embodiments 1 to 4.

Embodiment 11

An imaging probe comprising a detectable label, preferably an isotope selected from the group consisting of $^3$H, $^{11}$C, $^{13}$N, $^{15}$O, $^{18}$F, $^{19}$F, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, and $^{203}$Pb and a bio-orthogonal reactive group, wherein the bio-orthogonal reactive group is a reaction partner for a [4+2] retro Diels-Alder reaction between a diene according to any one of the formulae (2)-(5) as defined in embodiment 5, and a dienophile according to formula (1) as defined in any one of the embodiments 1 to 4.

Embodiment 12

A therapeutic probe comprising a pharmaceutically active compound, preferably an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac, and a bio-orthogonal reactive group, wherein the bio-orthogonal reactive group is a reaction partner for a [4+2] retro Diels-Alder reaction between a diene according to any one of the formulae (2)-(5) as defined in embodiment 5, and a dienophile according to formula (1) as defined in any one of the embodiments 1 to 4.

Embodiment 13

A pretargeting method comprising administering a pretargeting agent according to embodiment 10 to a subject and allowing the agent to circulate in the subject's system for a period of time effective to achieve binding of the primary targeting moiety to a primary target, followed by clearing non-bound agent from the body.

Embodiment 14

An imaging method comprising conducting a pretargeting method according to embodiment 13, followed by the administration of an imaging probe according to embodiment 11, wherein the bio-orthogonal reactive groups in the pretargeting agent and in the imaging probe together form the reactive partners for said [4+2] retro Diels-Alder reaction.

Embodiment 15

A method of targeted medical treatment in a subject, comprising conducting a pretargeting method according to embodiment 13, followed by the administration of a therapeutic probe according to embodiment 12, wherein the bio-orthogonal reactive groups in the pretargeting agent and in the therapeutic probe together form the reactive partners for said [4+2] retro Diels-Alder reaction.

Embodiment 16

An agent according to embodiment 10 for use in a method according to any one of the embodiments 13 to 15.

Embodiment 17

A compound satisfying formula (1) as defined in any one of the embodiments 1 to 4, for use in a pre-targeting method in an animal or a human being.

Embodiment 18

The use of a trans cyclooctene having one or more axial substituents, preferably a compound satisfying formula (1) as defined in any one of the embodiments 1 to 4, as a dienophile reactant in a pre-targeting method based on the retro Diels-Alder reaction.

The invention claimed is:
1. A kit for targeted medical imaging and/or therapeutics, comprising at least one Pre-targeting Probe and at least one Effector Probe, which undergo [4+2] cycloaddition in vivo, wherein the Pre-targeting Probe comprises a Primary Targeting Moiety and a first Bio-orthogonal Reactive Group, and wherein the Effector Probe comprises an Effector Moiety and a second Bio-orthogonal Reactive Group, wherein either of the first or second Bio-orthogonal Reactive Groups is a dienophile, and the other of the first and second Bio-orthogonal Reactive Groups is a diene, wherein the dienophile is an 8-member ring dienophile comprising trans-cyclooctene satisfying formula (1):

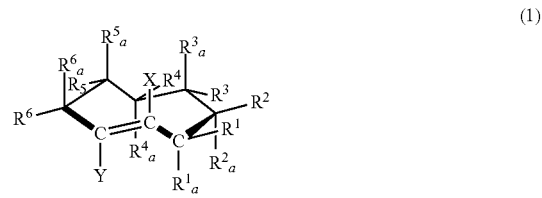

wherein the position of R is equatorial and the position of $R_a$ is axial, wherein each of X, Y, R, and $R_a$ independently denotes H, or, in at most six instances, a group selected from alkyl, aryl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si-O-alkyl, OCO-alkyl, OCO-aryl, SCO-alkyl, SCO-aryl, OCS-alkyl, OCS-aryl, SCS-alkyl, SCS-aryl, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl; with one of R or $R_a$ comprised in a Linker Moiety to the Pre-targeting Probe or the Effector Probe; wherein two R or $R_a$ moieties together may form a ring; wherein at least one and maximally four of $R_a$ is not hydrogen,
wherein the Primary Targeting Moiety is selected from the group of antibodies; antibody fragments selected from Fab2, Fab, scFV and diabodies; polymers which are tumor targeting by virtue of the enhanced permeability and retention (EPR)-effect; proteins; peptides; carbohydrates; monosaccharides; polysaccharides; viruses; whole cells; phage; drugs; chemotherapeutic agents, receptor agonists and antagonists, cytokines, hormones, steroids, and; nucleic acids;
wherein the Effector Moiety is a detectable label selected from the group consisting of MRI-imageable agents being a superparamagnetic particle or a paramagnetic ion selected from Gd, Fe, Mn, Cr, Co, Ni, Cu, Pr, Nd, Yb, Tb, Dy, Ho, Er, Sm, Eu, Ti, Pa, La, Sc, V, Mo, Ru, Ce, Dy, Tl; spin labels; optical labels; an ultrasound-responsive agent being a microbubble, the shell of which is selected from a phospholipid, a (biodegradable) polymer, and human serum albumin; X-ray-responsive agents selected from iodine, barium, barium sulfate, gastrografin, a vesicle filled with iodine compounds and/or barium sulfate, a liposome filled with iodine compounds and/or barium sulfate, and a polymer capsule filled with iodine compounds and/or barium sulfate; radionuclides selected from $^{3}$H, $^{11}$C, $^{13}$N, $^{15}$O, $^{18}$F, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, and $^{203}$Pb; FRET-type dyes; (bio)luminescent or fluorescent molecules or tags; biotin; small size organic PET and SPECT labels selected from $^{18}$F, $^{11}$C and $^{123}$I;

and/or wherein the Effector Moiety is a therapeutic moiety, a drug or a radioactive isotope for radiation therapy selected from $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac.

2. A kit according to claim 1, wherein the dienophile of formula 1 satisfies one or more of the following requirements:

a) X is H or methyl
b) Y is H or methyl;
c) one or more substituents $R^{2}_{a}$, $R^{3}_{a}$, $R^{4}_{a}$, $R^{5}_{a}$ are O-alkyl;
d) one or more substituents $R^{2}_{a}$, $R^{3}_{a}$, $R^{4}_{a}$, $R^{5}_{a}$ are O-aryl;
e) one or more substituents $R^{2}_{a}$, $R^{3}_{a}$, $R^{4}_{a}$, $R^{5}_{a}$ are alkyl; and
f) one or more substituents $R^{2}_{a}$, $R^{3}_{a}$, $R^{4}_{a}$, $R^{5}_{a}$ are aryl.

3. A kit according to claim 1, wherein the diene is selected from the group consisting of compounds of the formulae (2), (3), (4), and (5) as defined below:

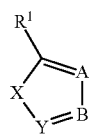
(2)

wherein $R^{1}$ is selected from the group consisting of H, alkyl, aryl, CF$_3$, CF$_2$—R', OR', SR', C(=O)R', C(=S)R', C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", NR'C(=O)NR"R'", NR'C(=S)N'R"R'" with R', R", and R'" each independently being H, aryl or alkyl; A and B each independently are selected from the group consisting of alkyl-substituted carbon, aryl substituted carbon, nitrogen, N$^+$O$^-$, N$^+$R with R being alkyl, with the proviso that A and B are not both carbon; X is selected from the group consisting of O, N-alkyl, and C=O, and Y is CR with R being selected from the group consisting of H, alkyl, aryl, C(=O)OR', C(=O)SR', C(=S)OR', C(=S)SR', C(=O)NR'R" with R' and R" each independently being H, aryl or alkyl;

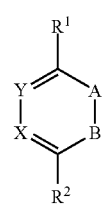
(3)

wherein $R^{1}$ and $R^{2}$ each independently are selected from the group consisting of H, alkyl, aryl, CF$_3$, CF$_2$—R', NO$_2$, OR', SR', C(=O)R', C(=S)R', OC(=O)R'", SC(=O)R'", OC(=S)R'", SC(=S)R'", S(=O)R', S(=O)$_2$R'", S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R"R'" with R' and R" each independently being H, aryl or alkyl, and R'" independently being aryl or alkyl; A is selected from the group consisting of N-alkyl, N-aryl, C=O, and CN-alkyl; B is O or S; X is selected from the group consisting of N, CH, C-alkyl, C-aryl, CC(=O)R', CC(=S)R', CS(=O)R', CS(=O)$_2$R'", CC(=O)O—R', CC(=O)S—R', CC(=S)O—R', CC(=S)S—R', CC(=O)NR'R", CC(=S)NR'R", R' and R" each independently being H, aryl or alkyl and R'" independently being aryl or alkyl; Y is selected from the group consisting of CH, C-alkyl, C-aryl, N, and N$^+$O$^-$;

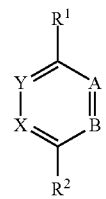
(4)

wherein $R^{1}$ and $R^{2}$ each independently are selected from the group consisting of H, alkyl, aryl, CF$_3$, CF$_2$—R', NO$_2$, OR', SR', C(=O)R', C(=S)R', OC(=O)R'", SC(=O)R'", OC(=S)R'", SC(=S)R'", S(=O)R', S(=O)$_2$R'", S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R"R'" with R' and R" each independently being H, aryl or alkyl, and R'" independently being aryl or alkyl; A is selected from the group consisting of N, C-alkyl, C-aryl, and N$^+$O$^-$; B is N; X is selected from the group consisting of N, CH, C-alkyl, C-aryl, CC(=O)R', CC(=S)R', CS(=O)R', CS(=O)$_2$R'", CC(=O)O—R', CC(=O)S—R', CC(=S)O—R', CC(=S)S—R', CC(=O)NR'R", CC(=S)NR'R", R' and R" each independently being H, aryl or alkyl and R'" independently being aryl or alkyl; Y is selected from the group consisting of CH, C-alkyl, C-aryl, N, and N$^+$O$^-$;

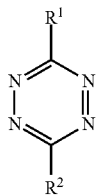

(5)

wherein R¹ and R² each independently denote a substituent selected from the group consisting of H, 2-pyridyl, 3, pyridyl, 4-pyridyl, 2,6-pyrimidyl, 2,5-pyrimidyl, 3,5-pyrimidyl, 2,4-pyrimidyl, or phenyl, optionally substituted with one or more electron-withdrawing groups such as $NO_2$, F, Cl, CF3, CN, COOH, COOR, $CONH_2$, CONHR, $CONR_2$, CHO, COR, $SO_2R$, $SO_2OR$, NO, Ar, wherein R is $C_1$-$C_6$ alkyl and Ar stands for an aromatic group, particularly phenyl, pyridyl, or naphthyl, wherein R¹ and R², including those on X or Y, in each of formula (2) to (5) can further be provided with a suitable linker or spacer moiety to connect the Primary Targeting Moiety and/or Effector Moiety to the diene.

4. A pretargeting agent comprising a primary targeting moiety as defined in claim 1 and a bio-orthogonal reactive group, wherein the bio-orthogonal reactive group is a dienophile according to formula (1) as defined in claim 1.

5. An imaging probe comprising a detectable label as defined in claim 1 and a bio-orthogonal reactive group, wherein the bio-orthogonal reactive group is a dienophile according to formula (1) as defined in claim 1.

6. A therapeutic probe comprising a pharmaceutically active compound as defined in claim 1 and a bio-orthogonal reactive group, wherein the bio-orthogonal reactive group is a dienophile according to formula (1) as defined in claim 1.

7. A compound satisfying formula (1) as defined in claim 1, for use in a pre-targeting method in an animal or a human being.

8. A kit for targeted medical imaging and/or therapeutics, comprising at least one Pre-targeting Probe and at least one Effector Probe, which undergo [4+2] cycloaddition in vivo, wherein the Pre-targeting Probe comprises a Primary Targeting Moiety and a first Bio-orthogonal Reactive Group, and wherein the Effector Probe comprises an Effector Moiety and a second Bio-orthogonal Reactive Group, wherein either of the first or second Bio-orthogonal Reactive Groups is a dienophile, and the other of the first and second Bio-orthogonal Reactive Groups is a diene, wherein the dienophile is an 8-member ring dienophile comprising trans-cyclooctene satisfying formula (1):

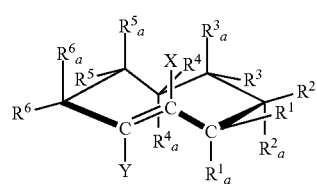

(1)

wherein the position of R is equatorial and the position of $R_a$ is axial, wherein each of X, Y, R, and $R_a$ independently denotes H, or, in at most six instances, a group selected from F, Cl, Br, I, $N_3$, $SO_2H$, $SO_3H$, $SO_4H$, $PO_4H$, OH, SH, $NO_2$, NO, CN, OCN, SCN, NCO, NCS, and $CF_3$; with one of R or $R_a$ comprised in a Linker Moiety to the Pre-targeting Probe or the Effector Probe; wherein two R or $R_a$ moieties together may form a ring; wherein at least one and maximally four of $R_a$ is not hydrogen, wherein the Primary Targeting Moiety is selected from the group of antibodies; antibody fragments selected from Fab2, Fab, scFV and diabodies; polymers which are tumor targeting by virtue of the enhanced permeability and retention (EPR)-effect; proteins; peptides; carbohydrates; monosaccharides; polysaccharides; viruses; whole cells; phage; drugs; chemotherapeutic agents, receptor agonists and antagonists, cytokines, hormones, steroids, and; nucleic acids;

wherein the Effector Moiety is a detectable label selected from the group consisting of MRI-imageable agents being a superparamagnetic particle or a paramagnetic ion selected from Gd, Fe, Mn, Cr, Co, Ni, Cu, Pr, Nd, Yb, Tb, Dy, Ho, Er, Sm, Eu, Ti, Pa, La, Sc, V, Mo, Ru, Ce, Dy, Tl; spin labels; optical labels; an ultrasound-responsive agent being a microbubble, the shell of which is selected from a phospholipid, a (biodegradable) polymer, and human serum albumin; X-ray-responsive agents selected from iodine, barium, barium sulfate, gastrografin, a vesicle filled with iodine compounds and/or barium sulfate, a liposome filled with iodine compounds and/or barium sulfate, and a polymer capsule filled with iodine compounds and/or barium sulfate; radionuclides selected from $^{3}H$, $^{11}C$, $^{13}N$, $^{15}O$, $^{18}F$, $^{51}Cr$, $^{52}Fe$, $^{52}Mn$, $^{55}Co$, $^{60}Cu$, $^{61}Cu$, $^{62}Zn$, $^{62}Cu$, $^{63}Zn$, $^{64}Cu$, $^{66}Ga$, $^{67}Ga$, $^{68}Ga$, $^{70}As$, $^{71}As$, $^{72}As$, $^{74}As$, $^{75}Se$, $^{75}Br$, $^{76}Br$, $^{77}Br$, $^{80}Br$, $^{82}Br$, $^{82}Rb$, $^{86}Y$, $^{88}Y$, $^{89}Sr$, $^{89}Zr$, $^{97}Ru$, $^{99}Tc$, $^{110}In$, $^{111}In$, $^{113}In$, $^{114}In$, $^{117}Sn$, $^{120}I$, $^{122}Xe$, $^{123}I$, $^{124}I$, $^{125}I$, $^{166}Ho$, $^{167}Tm$, $^{169}Yb$, $^{193}Pt$, $^{195}Pt$, $^{201}Ti$, and $^{203}Pb$; FRET-type dyes; (bio)luminescent or fluorescent molecules or tags; biotin; small size organic PET and SPECT labels selected from $^{18}F$, $^{11}C$ and $^{123}I$;

and/or wherein the Effector Moiety is a therapeutic moiety, a drug or a radioactive isotope for radiation therapy selected from $^{24}Na$, $^{32}P$, $^{33}P$, $^{47}Sc$, $^{59}Fe$, $^{67}Cu$, $^{76}As$, $^{77}As$, $^{80}Br$, $^{82}Br$, $^{89}Sr$, $^{90}Nb$, $^{90}Y$, $^{103}Ru$, $^{105}Rh$, $^{109}Pd$, $^{111}Ag$, $^{121}Sn$, $^{127}Te$, $^{131}I$, $^{140}La$, $^{141}Ce$, $^{142}Pr$, $^{143}Pr$, $^{144}Pr$, $^{149}Pm$, $^{149}Tb$, $^{151}Pm$, $^{153}Sm$, $^{159}Gd$, $^{161}Tb$, $^{165}Dy$, $^{166}Dy$, $^{166}Ho$, $^{169}Er$, $^{172}Tm$, $^{175}Yb$, $^{177}Lu$, $^{186}Re$, $^{188}Re$, $^{198}Au$, $^{199}Au$, $^{211}AT$, $^{211}Bi$, $^{212}Bi$, $^{212}Pb$, $^{213}Bi$, $^{214}Bi$, $^{223}Ra$, and $^{225}AC$.

9. A kit according to claim 1, wherein the dienophile of formula 1 satisfies the following requirement:

X, Y, R¹, R¹$_a$, R⁶ and R⁶$_a$ are hydrogen; R², R²$_a$, R³, R³$_a$, R⁴, R⁴$_a$, R⁵, R⁵$_a$ are hydrogen or alkyl, aryl, O-aryl, O-alkyl, $N_3$, $SO_3H$, OH, CN, NR'R" with R' and R" each independently being H or alkyl, aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, CR'NR" with R' and R" each independently being H , alkyl or aryl; with one of R or $R_a$ comprised in a Linker Moiety to the Pre-targeting Probe or the Effector Probe; wherein two R or $R_a$ moieties together may form a ring; wherein at least one $R_a$ is not hydrogen, and wherein maximally three of R and $R_a$ is not a hydrogen ring; wherein at least one $R_a$ is not hydrogen, and wherein maximally three of R and $R_a$ is not a hydrogen.

10. A kit according to claim 1, wherein the diene is selected from the group consisting of compounds of the formulae (4) as defined below:

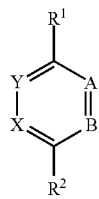

(4)

wherein $R^1$ and $R^2$ each independently are selected from the group consisting of H, alkyl, aryl, $CF_3$, $CF_2$-R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR'R'', NR'C(=S)N'R'R'' with R' and R'' each independently being H, aryl or alkyl, and R''' independently being aryl or alkyl; A, B; X and Y are N; and wherein $R^1$ and $R^2$ can further be provided with a suitable linker or spacer moiety to connect the Primary Targeting Moiety or Effector Moiety to the diene.

11. A kit according to claim 1, wherein the diene is selected from the group consisting of compounds of the formulae (5) as defined below:

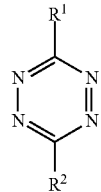

(5)

wherein $R^1$ and $R^2$ each independently denote a substituent selected from the group consisting of H, 2-pyridyl, 3-pyridyl, 4-pyridyl, 2,6-pyrimidyl, 2,5-pyrimidyl, 3,5-pyrimidyl, 2,4-pyrimidyl , or phenyl, optionally substituted with one or more electron-withdrawing groups suchas $NO_2$, F, Cl, $CF_3$, CN, COOH, COOR, CONH2, CONHR, CONR$_2$, CHO, COR, SO2$_R$, SO$_2$OR, NO, Ar, wherein R is $C_1$-$C_6$ alkyl and Ar stands for an aromatic group, particularly phenyl, pyridyl, or naphthyl; and wherein $R^1$ and $R^2$ can further be provided with a suitable linker or spacer moiety to connect the Primary Targeting Moiety or Effector Moiety to the diene.

* * * * *